(12) United States Patent
Daley-Beckford et al.

(10) Patent No.: US 9,278,081 B2
(45) Date of Patent: Mar. 8, 2016

(54) **EXTRACTS FROM *EUCALYPTUS CAMALDULENSIS* FOR THE TREATMENT OF HYPERGLYCEMIA AND HYPERTENSION**

(71) Applicant: The University of the West Indies, Kingston 7 (JM)

(72) Inventors: Denise Daley-Beckford, St. Catherine (JM); Trevor Herbert Yee, Kingston (JM); Ruby Lisa Alexander-Lindo, Kingston (JM); Paul Bancroft Reese, Kingston (JM)

(73) Assignee: University of The West Indies, Kingston (JM)

( * ) Notice: Subject to any disclaimer, the term of this patent is extended or adjusted under 35 U.S.C. 154(b) by 0 days.

(21) Appl. No.: 14/046,759

(22) Filed: Oct. 4, 2013

(65) Prior Publication Data

US 2014/0100279 A1    Apr. 10, 2014

Related U.S. Application Data

(60) Provisional application No. 61/722,614, filed on Nov. 5, 2012, provisional application No. 61/709,893, filed on Oct. 4, 2012.

(51) Int. Cl.
| | |
|---|---|
| *A61K 31/20* | (2006.01) |
| *A61K 31/201* | (2006.01) |
| *A61K 31/01* | (2006.01) |
| *A61K 36/61* | (2006.01) |

(52) U.S. Cl.
CPC .............. *A61K 31/201* (2013.01); *A61K 31/01* (2013.01); *A61K 31/20* (2013.01); *A61K 36/61* (2013.01)

(58) Field of Classification Search
USPC ................................................ 514/560, 762
See application file for complete search history.

(56) References Cited

U.S. PATENT DOCUMENTS 7,799,782 B2 *   9/2010   Munson et al. ............ 514/234.5
8,048,426 B2 *   11/2011   Hsieh et al. ............ 424/195.17

OTHER PUBLICATIONS

Moraes et al., Pharmacol. Ther., 2006, 110:371-85.*
Kliewer, Steven et al. "Fatty acids and eicosanoids regulate gene expression through direct interactions with peroxisome proliferator-activated receptors α and γ." Proc. Natl. Acad. Sci. USA. Apr. 1997, vol. 94, pp. 4318-4323. 6 pages.
Aminot-Gilchrist, D. V. And Anderson, H. D. I., "Insulin resistance-associated cardiovascular disease: potential benefits of conjugated linoleic acid," Am. J. Clin. Nutr., vol. 79, Supplemental, pp. 1159S-1163S (2004).
Choi, J. S. et al., "Effect of conjugated linoleic acid isomers on insulin resistance and mRNA levels of genes regulating energy metabolism in high-fat-fed rats," Nutrition, vol. 20, No. 11-12, pp. 1008-1017 (Nov.-Dec. 2004).
Daley-Beckford, D. K. et al., "Fatty acids isolated from *Eucalyptus camaldulensis* showing a dose dependent hypoglycaemic effect," West Indian Medical Journal, vol. 59, Suppl. 4, p. 25 (2010).
Daley-Beckford, D. K. et al., "Hypoglycaemic Compounds Isolated from *Eucalyptus camaldulensis* Showing a Similar Effect with Metformin," West Indian Medical Journal, vol. 59, Suppl. 1, p. 47 (2010).
Daley-Beckford, D. K. et al., "The Isolation, Purification and Elucidation of the Hypoglycaemic Principle of *Eucalyptus camaldulensis* in Normoglycaemic Sprague-Dawley Rats," West Indian Medical Journal, vol. 58, Suppl. 1, p. 39 (2009).
Daley-Beckford, D. K. et al., "The isolation of the hypoglycaemic principles of *Eucalyptus camaldulensis*, showing a similar effect as metformin," West Indian Medical Journal, vol. 58, Suppl. 4, p. 44 (2009).
De Bona, K. S. et al., "Syzgium cumini Extract Decreases Adenosine Deaminase, 5'Nucleotidase Activities and Oxidative Damage in Platelets of Diabetic Patients," Cellular Physiology and Biochemistry, vol. 26, pp. 729-738 (2010).
Eyjolfson, V. et al., "Conjugated Linoleic Acid Improves Insulin Sensitivity in Young, Sedentary Humans," Medicine & Science in Sports & Exercise, pp. 814-820 (2004).
Gray, a. M. And Flatt, P. R., "Antihyperglycemic Actions of Eucalyptus globulus (Eucalyptus) are Associated with Pancreatic and Extra-Pancreatic Effects in Mice," The Journal of Nutrition, vol. 128, pp. 2319-2323 (1998).
Hashimoto, M. et al., "Synthesis of Palmitoyl Derivatives of Insulin and Their Biological Activities," Pharmaceutical Research, vol. 6, No. 2, pp. 171-176 (1989).
Henriksen, E. J. et al., "Isomer-specific actions of conjugated linoleic acid on muscle glucose transport in the obese Zucker rat," Am. J. Physiol. Endocrinol. Metab., vol. 285, pp. E98-E105 (2003).
Inoue, N. et al., "Conjugated linoleic acid prevents the development of essential hypertension in spontaneously hypertensive rats," Biochemical and Biophysical Research Communications, vol. 323, No. 2, pp. 679-684 (Oct. 15, 2004).
Ismail, Shahbaa Muslem, "The Effect of Aqueous Extract of the Leaves of Eucalyptus Globules on the Blood Glucose Level in Fasted Rats," Iranian Journal of Pharmacology and Therapeutics (IJPT), vol. 6, pp. 239-240 (2007).
Khanal, R. C., "Potential Health Benefits of Conjugated Linoleic Acid (CLA): A Review," Asian-Aust. J. Anim. Sci., vol. 17, No. 9, pp. 1315-1328 (2004).
Kumar, A. et al., "Neutral components in the leaves and seeds of Syzygium cumini," African Journal of Pharmacy and Pharmacology, vol. 3, No. 11, pp. 560-561 (Nov. 2009).
Norris, L. E. et al., "Comparison of dietary conjugated linoleic acid with safflower oil on body composition in obese postmenopausal women with type 2 diabetes mellitus," Am. J. Clin. Nutr., vol. 90, pp. 468-476 (2009).

(Continued)

*Primary Examiner* — Rei-Tsang Shiao
(74) *Attorney, Agent, or Firm* — Wilmer Cutler Pickering Hale and Dorr LLP

(57) ABSTRACT

The present invention relates to the discovery that compounds isolated from the leaves of the plant *Eucalyptus camaldulensis* can be used to treat or prevent hyperglycemia and/or hypertension.

20 Claims, 29 Drawing Sheets

(56) References Cited

OTHER PUBLICATIONS

Onuki, Y. et al., "In vivo effects of highly purified docosahexaenoic acid on rectal insulin absorption," International Journal of Pharmaceutics, vol. 198, pp. 147-156 (2000).

Phillips, M. et al., "Increased breath biomarkers of oxidative stress in diabetes mellitus," Clinica Chimica Acta, vol. 344, pp. 189-194 (2004).

Rocca, A. S. et al., "Monounsaturated fatty acid diets improve glycemic tolerance through increased secretion of glucagon-like peptide-1," Endocrinology, vol. 142, No. 3, pp. 1148-1155 (Mar. 2001).

Ross, R. A. et al., "Differential effects of hypothalamic long-chain fatty acid infusions on suppression of hepatic glucose production," Am. J. Physiol. Endocrinol. Metab., vol. 299, pp. E633-E639 (2010).

Ryder, J. W. et al., "Isomer-Specific Antidiabetic Properties of Conjugated Linoleic Acid," Diabetes, vol. 50, pp. 1149-1157 (May 2001).

Sharma, A. K. et al., "Syzygium cumini Ameliorates Insulin Resistance and $\beta$-Cell Dysfunction via Modulation of PPAR$\gamma$, Dyslipidemia, Oxidative Stress, and TNF-$\alpha$ in Type 2 Diabetic Rats," J. Pharmacol. Sci., vol. 119, pp. 205-213 (2012).

Soriguer, F. et al., "Oleic acid from cooking oils is associated with lower insulin resistance in the general population (Pizarra study)," European Journal of Endocrinology, vol. 150, pp. 33-39 (2004).

Terés, S. et al., "Oleic acid content is responsible for the reduction in blood pressure induced by olive oil," PNAs, vol. 105, No. 37, pp. 13811-13816 (Sep. 16, 2008).

Wang, Paul Y., "The Reliability of a Compressed Mixture of Insulin and Palmitic Acid to Sustain a Reduction in Hyperglycemia in Rodents," Trans. Am. Soc. Artif. Intern. Organs, vol. 33, pp. 319-322 (1987).

Watras, A. C. et al., "The role of conjugated linoleic acid in reducing body fat and preventing holiday weight gain," International Journal of Obesity, vol. 31, pp. 481-487 (2007).

\* cited by examiner

EXTRACTS FROM *EUCALYPTUS CAMALDULENSIS* FOR THE TREATMENT OF HYPERGLYCEMIA AND HYPERTENSION

This application claims priority to U.S. Provisional Application No. 61/709,893, filed on Oct. 4, 2012, and U.S. Provisional Application 61/722,614, filed on Nov. 5, 2012, which are herein incorporated by reference in their entireties.

All patents, patent applications and publications, and non-patent publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

High blood sugar (hyperglycemia) affects people who have diabetes. Several factors can contribute to hyperglycemia in people with diabetes, including food and physical activity choices, illness, nondiabetes medications, or not taking enough glucose-lowering medication (see e.g., http://www-.mayoclinic.com/health/hyperglycemia/DS01168).

Research into alternative treatment for diabetes, such as plant treatments, may provide valuable clues for the development of new oral hypoglycaemic agents. *Eucalyptus camaldulensis*, commonly called River Red Rum, is a species being investigated for the hypoglycaemic principle present within the leaves. The *eucalyptus* is a large, fast-growing evergreen from the Myrtaceae family having over 800 species.

SUMMARY OF THE INVENTION

The present invention relates to the discovery that compounds isolated from *Eucalyptus camaldulensis* can be used for the treatment of hyperglycemia and/or hypertension.

In one aspect, the present invention provides for a method of treating or preventing hyperglycemia, the method comprising administering to a subject in need thereof a therapeutically effective amount of one or more compounds isolated from *Eucalyptus camaldulensis*, thereby treating or preventing the hyperglycemia.

In another aspect, the present invention provides for a method of treating or preventing hypertension, the method comprising administering to a subject in need thereof a therapeutically effective amount of one or more compounds isolated from *Eucalyptus camaldulensis*, thereby treating or preventing the hypertension.

In one embodiment, the subject has been diagnosed with diabetes mellitus. In one embodiment, the compound is oleic acid, palmitic acid or both. In another embodiment, the compound is eicosane.

In one aspect, the present invention provides for a method of treating or preventing hyperglycemia, the method comprising administering to a subject in need thereof a therapeutically effective amount of a composition comprising oleic acid and palmitic acid, thereby treating or preventing the hyperglycemia.

In one embodiment, the oleic acid and palmitic acid are present in a ratio of about 3:1 oleic acid:palmitic acid. In another embodiment, the oleic acid and palmitic acid are present in a ratio of about 1:1 oleic acid:palmitic acid. In another embodiment, the oleic acid and palmitic acid are present in a ratio of about 1:3 oleic acid:palmitic acid. In another embodiment, the oleic acid and palmitic acid are present in a ratio of 2.3:1 oleic acid:palmitic acid.

In one embodiment, the oleic acid and palmitic acid are extracted from the leaves of *Eucalyptus camaldulensis*. In another embodiment, the oleic acid and the palmitic acid have a synergistic effect on hyperglycemia.

In one embodiment, the treating or preventing comprises lowering the subject's blood glucose concentration by about 10%. In another embodiment, the treating or preventing comprises lowering the subject's blood glucose concentration by about 15%. In another embodiment, the treating or preventing comprises lowering the subject's blood glucose concentration by about 20%. In one embodiment, the treating or preventing comprises lowering the subject's blood glucose concentration by about 25%. In another embodiment, the treating or preventing comprises lowering the subject's blood glucose concentration by about 30%.

In another aspect, the present invention provides for a method of treating or preventing hypertension, the method comprising administering to a subject in need thereof a therapeutically effective amount of a composition comprising oleic acid and palmitic acid, thereby treating or preventing the hypertension.

In one embodiment, the oleic acid and palmitic acid are present in a ratio of about 3:1 oleic acid:palmitic acid. In another embodiment, the oleic acid and palmitic acid are present in a ratio of about 1:1 oleic acid:palmitic acid. In another embodiment, the oleic acid and palmitic acid are present in a ratio of about 1:3 oleic acid:palmitic acid. In another embodiment, the oleic acid and palmitic acid are present in a ratio of 2.3:1 oleic acid:palmitic acid.

In one embodiment, the oleic acid and palmitic acid are extracted from the leaves of *Eucalyptus camaldulensis*. In another embodiment, the oleic acid and the palmitic acid have a synergistic effect on hypertension.

In one embodiment, the treating or preventing comprises reducing the subject's systolic blood pressure (SBP) by about 10%. In another embodiment, the treating or preventing comprises reducing the subject's systolic blood pressure (SBP) by about 15%. In one embodiment, the treating or preventing comprises reducing the subject's systolic blood pressure (SBP) by about 20%. In another embodiment, the treating or preventing comprises reducing the subject's systolic blood pressure (SBP) by about 25%.

In one embodiment, the treating or preventing comprises reducing the subject's diastolic blood pressure (DBP) by about 5%. In another embodiment, the treating or preventing comprises reducing the subject's diastolic blood pressure (DBP) by about 10%. In one embodiment, the treating or preventing comprises reducing the subject's diastolic blood pressure (DBP) by about 15%. In another embodiment, the treating or preventing comprises reducing the subject's diastolic blood pressure (DBP) by about 20%. In one embodiment, the treating or preventing comprises reducing the subject's diastolic blood pressure (DBP) by about 25%.

In one embodiment, the treating or preventing comprises reducing the subject's heart rate by about 5%. In another embodiment, the treating or preventing comprises reducing the subject's heart rate by about 10%. In one embodiment, the treating or preventing comprises reducing the subject's heart rate by about 15%. In another embodiment, the treating or preventing comprises reducing the subject's heart rate by about 20%.

In another aspect, the present invention provides for a method of treating or preventing hyperglycemia, the method comprising administering to a subject in need thereof a therapeutically effective amount of a composition comprising olive oil and coconut oil, thereby treating or preventing the hyperglycemia.

In one embodiment, the olive oil and coconut oil are present in a ratio of 2.3:1 olive oil:coconut oil. In another embodiment, the olive oil and coconut oil are present in a ratio of about 1:1 olive oil:coconut oil. In one embodiment, the olive oil and coconut oil are present in a ratio of about 3:1 olive oil:coconut oil. In one embodiment, the olive oil and coconut oil are present in a ratio of about 1:3 olive oil:coconut oil.

In one embodiment, the olive oil and the coconut oil have a synergistic effect on hyperglycemia.

In one embodiment, the treating or preventing comprises lowering the subject's blood glucose concentration by about 10%. In another embodiment, the treating or preventing comprises lowering the subject's blood glucose concentration by about 15%. In one embodiment, the treating or preventing comprises lowering the subject's blood glucose concentration by about 20%. In another embodiment, the treating or preventing comprises lowering the subject's blood glucose concentration by about 25%. In one embodiment, the treating or preventing comprises lowering the subject's blood glucose concentration by about 30%.

In another aspect, the present invention provides for a method of treating or preventing hyperglycemia, the method comprising administering to a subject in need thereof a therapeutically effective amount of one or more compounds, wherein at least one compound is eicosane, thereby treating or preventing the hyperglycemia.

In one embodiment, the subject has been diagnosed with diabetes mellitus. In another embodiment, the eicosane is isolated from *Eucalyptus camaldulensis*.

In one embodiment, the treating or preventing comprises lowering the subject's blood glucose concentration by about 10%. In another embodiment, the treating or preventing comprises lowering the subject's blood glucose concentration by about 15%. In one embodiment, the treating or preventing comprises lowering the subject's blood glucose concentration by about 20%. In another embodiment, the treating or preventing comprises lowering the subject's blood glucose concentration by about 25%. In one embodiment, the treating or preventing comprises lowering the subject's blood glucose concentration by about 30%.

In one embodiment, the treating or preventing comprises increasing the subject's blood insulin levels by about 30%. In another embodiment, the treating or preventing comprises increasing the subject's blood insulin levels by about 50%. In one embodiment, the treating or preventing comprises increasing the subject's blood insulin levels by about 80%.

In another aspect, the present invention provides for a method of treating or preventing hypertension, the method comprising administering to a subject in need thereof a therapeutically effective amount of one or more compounds, wherein at least one compound is eicosane, thereby treating or preventing the hypertension.

In one embodiment, the subject has been diagnosed with diabetes mellitus. In one embodiment, the eicosane is isolated from *Eucalyptus camaldulensis*.

In one embodiment, the treating or preventing comprises reducing the subject's systolic blood pressure (SBP) by about 15%. In another embodiment, the treating or preventing comprises reducing the subject's systolic blood pressure (SBP) by about 20%. In one embodiment, the treating or preventing comprises reducing the subject's systolic blood pressure (SBP) by about 25%.

In one embodiment, the treating or preventing comprises reducing the subject's diastolic blood pressure (DBP) by about 15%. In another embodiment, the treating or preventing comprises reducing the subject's diastolic blood pressure (DBP) by about 20%. In one embodiment, the treating or preventing comprises reducing the subject's diastolic blood pressure (DBP) by about 25%.

In one embodiment, the treating or preventing comprises reducing the subject's heart rate by about 5%. In another embodiment, the treating or preventing comprises reducing the subject's heart rate by about 10%. In one embodiment, the treating or preventing comprises reducing the subject's heart rate by about 15%.

In one embodiment, the treating or preventing comprises reducing the subject's mean arterial blood pressure by about 10%. In another embodiment, the treating or preventing comprises reducing the subject's mean arterial blood pressure by about 15%. In one embodiment, the treating or preventing comprises reducing the subject's mean arterial blood pressure by about 20%. In another embodiment, the treating or preventing comprises reducing the subject's mean arterial blood pressure by about 25%.

In one aspect, the present invention provides for a method of treating or preventing hyperglycemia, the method comprising administering to a subject in need thereof a therapeutically effective amount of a composition comprising oleic acid, palmitic acid and eicosane, thereby treating or preventing the hyperglycemia.

In one embodiment, the oleic acid and palmitic acid are present in a ratio of about 3:1 oleic acid:palmitic acid. In another embodiment, the oleic acid and palmitic acid are present in a ratio of about 1:1 oleic acid:palmitic acid. In another embodiment, the oleic acid and palmitic acid are present in a ratio of about 1:3 oleic acid:palmitic acid. In another embodiment, the oleic acid and palmitic acid are present in a ratio of 2.3:1 oleic acid:palmitic acid.

In one embodiment, the oleic acid, palmitic acid and eicosane are extracted from the leaves of *Eucalyptus camaldulensis*. In another embodiment, the oleic acid, palmitic acid and eicosane have a synergistic effect on hyperglycemia.

In one embodiment, the treating or preventing comprises lowering the subject's blood glucose concentration by about 10%. In another embodiment, the treating or preventing comprises lowering the subject's blood glucose concentration by about 15%. In another embodiment, the treating or preventing comprises lowering the subject's blood glucose concentration by about 20%. In one embodiment, the treating or preventing comprises lowering the subject's blood glucose concentration by about 25%. In another embodiment, the treating or preventing comprises lowering the subject's blood glucose concentration by about 30%.

In one embodiment, the treating or preventing comprises increasing the subject's blood insulin levels by about 30%. In another embodiment, the treating or preventing comprises increasing the subject's blood insulin levels by about 50%. In one embodiment, the treating or preventing comprises increasing the subject's blood insulin levels by about 80%.

In another aspect, the present invention provides for a method of treating or preventing hypertension, the method comprising administering to a subject in need thereof a therapeutically effective amount of a composition comprising oleic acid, palmitic acid and eicosane, thereby treating or preventing the hypertension.

In one embodiment, the oleic acid and palmitic acid are present in a ratio of about 3:1 oleic acid:palmitic acid. In another embodiment, the oleic acid and palmitic acid are present in a ratio of about 1:1 oleic acid:palmitic acid. In another embodiment, the oleic acid and palmitic acid are present in a ratio of about 1:3 oleic acid:palmitic acid. In another embodiment, the oleic acid and palmitic acid are present in a ratio of 2.3:1 oleic acid:palmitic acid.

In one embodiment, the oleic acid, palmitic acid and eicosane are extracted from the leaves of *Eucalyptus camaldulensis*. In another embodiment, the oleic acid, palmitic acid and eicosane have a synergistic effect on hypertension.

In one embodiment, the treating or preventing comprises reducing the subject's systolic blood pressure (SBP) by about 10%. In another embodiment, the treating or preventing comprises reducing the subject's systolic blood pressure (SBP) by about 15%. In one embodiment, the treating or preventing comprises reducing the subject's systolic blood pressure (SBP) by about 20%. In another embodiment, the treating or preventing comprises reducing the subject's systolic blood pressure (SBP) by about 25%.

In one embodiment, the treating or preventing comprises reducing the subject's diastolic blood pressure (DBP) by about 5%. In another embodiment, the treating or preventing comprises reducing the subject's diastolic blood pressure (DBP) by about 10%. In one embodiment, the treating or preventing comprises reducing the subject's diastolic blood pressure (DBP) by about 15%. In another embodiment, the treating or preventing comprises reducing the subject's diastolic blood pressure (DBP) by about 20%. In one embodiment, the treating or preventing comprises reducing the subject's diastolic blood pressure (DBP) by about 25%.

In one embodiment, the treating or preventing comprises reducing the subject's heart rate by about 5%. In another embodiment, the treating or preventing comprises reducing the subject's heart rate by about 10%. In one embodiment, the treating or preventing comprises reducing the subject's heart rate by about 15%. In another embodiment, the treating or preventing comprises reducing the subject's heart rate by about 20%.

In one aspect, the present invention provides for a method of preparing a composition with hypoglycemic properties, the method comprising isolating an extract from the leaves of *Eucalyptus camaldulensis*. In another aspect, the present invention provides for a method of preparing a composition with hypotensive properties, the method comprising isolating an extract from the leaves of *Eucalyptus camaldulensis*.

In another aspect, the present invention provides for a method of preparing a composition with hypoglycemic properties, the method comprising isolating an extract comprising one or more hypoglycemic compounds from the leaves of *Eucalyptus camaldulensis*.

In another aspect, the present invention provides for a method of preparing a composition with hypotensive properties, the method comprising isolating an extract comprising one or more hypotensive compounds from the leaves of *Eucalyptus camaldulensis*.

In one embodiment, the extract comprises palmitic acid, oleic acid, eicosane, or any combination thereof.

In one embodiment, the hypoglycemic compound is palmitic acid. In another embodiment, the hypoglycemic compound is oleic acid. In one embodiment, the hypoglycemic compound is eicosane. In another embodiment, the hypoglycemic compound is palmitic acid, oleic acid, eicosane, or any combination thereof.

In one embodiment, the hypotensive compound is palmitic acid. In another embodiment, the hypotensive compound is oleic acid. In one embodiment, the hypotensive compound is eicosane. In another embodiment, the hypotensive compound is palmitic acid, oleic acid, eicosane, or any combination thereof.

DETAILED DESCRIPTION OF THE INVENTION

Abbreviations and Definitions

Figure 1:
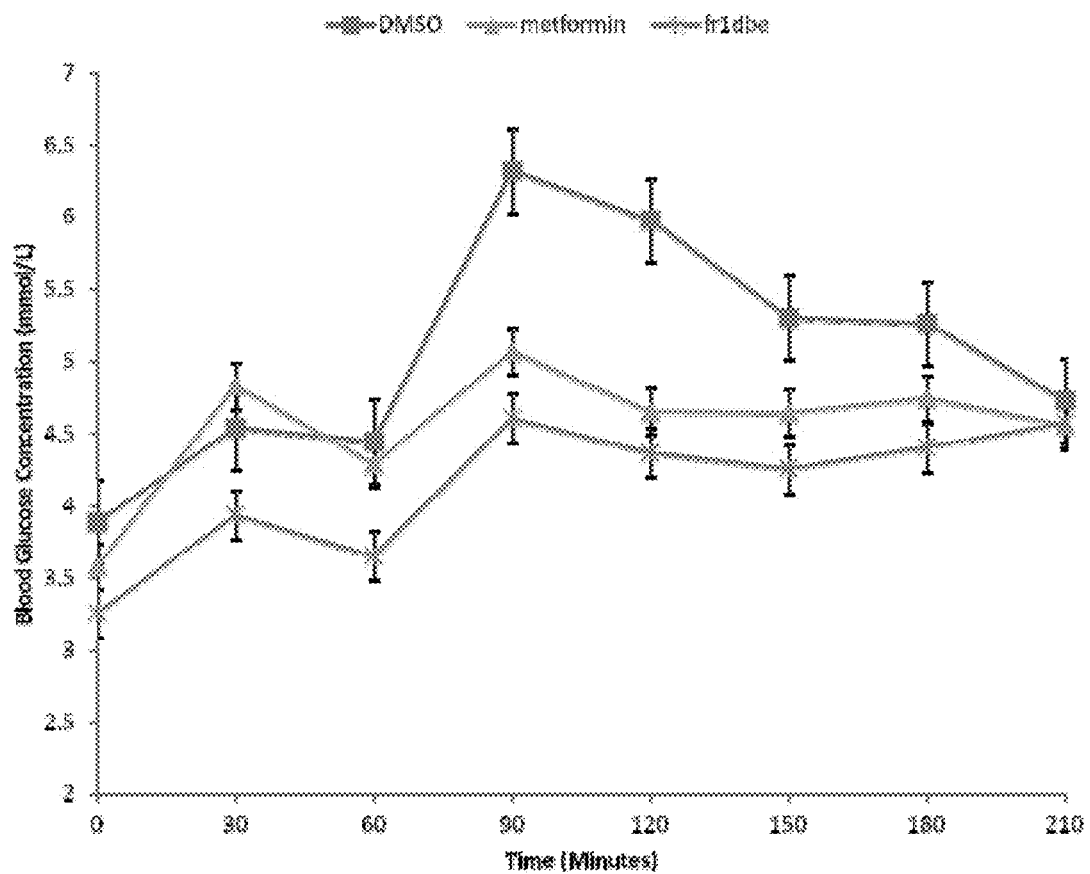
FIG. 1. GTC of FR1DBE at 30 mg/kg BW vs Metformin and DMSO via IV.

The singular forms "a", "an" and "the" include plural reference unless the context clearly dictates otherwise.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

The abbreviation GTC stands for Glucose Tolerance Curve.

The abbreviation DBP stands for Diastolic Blood Pressure.

The abbreviation SBP stands for Systolic Blood Pressure.

The abbreviation MAP stands for Mean Arterial Pressure.

The abbreviation FCC stands for Flash Column Chromatography.

The abbreviation BW stands for body weight.

The abbreviation OA stands for oleic acid.

The abbreviation PA stands for palmitic acid.

The abbreviation FR1DBY stands for palmitic acid. The structure of palmitic acid is well known in the art.

The abbreviation FR2DBW stands for an isolated combined mixture of oleic acid and palmitic acid. The structures of palmitic acid and oleic acid are well known in the art.

The abbreviation FR2DBS stands for oleic acid.

The abbreviation FR1DBE stands for eicosane. The structure of eicosane well known in the art.

DESCRIPTION

In one aspect, the present invention provides a method of treating or preventing hyperglycemia, the method comprising administering to a subject in need thereof a therapeutically effective amount of one or more compounds isolated from *Eucalyptus camaldulensis*, thereby treating or preventing the hyperglycemia.

In another aspect, the present invention provides a method of treating or preventing hypertension, the method comprising administering to a subject in need thereof a therapeutically effective amount of one or more compounds isolated from *Eucalyptus camaldulensis*, thereby treating or preventing the hypertension.

Part I. Fatty Acids Used for the Treatment of Hyperglycemia and Hypertension

Treatment and Prevention of Hyperglycemia

In one aspect, the present invention provides for a method of treating or preventing hyperglycemia, the method comprising administering to a subject in need thereof a therapeutically effective amount of one or more compounds isolated from *Eucalyptus camaldulensis*, thereby treating or preventing the hyperglycemia. In one embodiment, the compound is oleic acid, palmitic acid or both.

In one embodiment, in the treatment or prevention of hyperglycemia, the subject has been diagnosed with diabetes mellitus.

In one aspect, the present invention provides for a method of treating or preventing hyperglycemia, the method comprising administering to a subject in need thereof a therapeutically effective amount of a composition comprising oleic acid and palmitic acid, thereby treating or preventing the hyperglycemia.

In one embodiment, in the treatment or prevention of hyperglycemia, the oleic acid and palmitic acid are extracted from *Eucalyptus camaldulensis*. In one embodiment, the oleic acid and palmitic acid are extracted from the leaves of *Eucalyptus camaldulensis*. In another embodiment, the oleic acid and the palmitic acid have a synergistic effect on hyperglycemia.

In one embodiment in the treatment or prevention of hyperglycemia, the oleic acid and palmitic acid are present in a ratio of about 1:1 (oleic acid:palmitic acid). In another embodiment, the oleic acid and palmitic acid are present in a ratio of about 1.5:1 (oleic acid:palmitic acid). In another embodiment, the oleic acid and palmitic acid are present in a ratio of about 2:1 (oleic acid:palmitic acid). In one embodiment, the oleic acid and palmitic acid are present in a ratio of about 3:1 (oleic acid:palmitic acid). In another embodiment, the oleic acid and palmitic acid are present in a ratio of about 4:1 (oleic acid:palmitic acid). In one embodiment, the oleic acid and palmitic acid are present in a ratio of about 2.3:1 (oleic acid:palmitic acid). In one embodiment, the oleic acid and palmitic acid are present in a ratio of about 3:7 (oleic acid:palmitic acid). In one embodiment, the oleic acid and palmitic acid are present in a ratio of about 7:3 (oleic acid:palmitic acid). In one embodiment, the oleic acid and palmitic acid are present in a ratio of about 2.5:1 (oleic acid:palmitic acid). In one embodiment, the oleic acid and palmitic acid are present in a ratio of about 1:2.5 (oleic acid:palmitic acid). In one embodiment, the oleic acid and palmitic acid are present in a ratio of about 1:0 (oleic acid:palmitic acid). In one embodiment, the oleic acid and palmitic acid are present in a ratio of about 0:1 (oleic acid:palmitic acid).

In another embodiment in the treatment or prevention of hyperglycemia, the palmitic acid and oleic acid are present in a ratio of about 1:1 (palmitic acid:oleic acid). In another embodiment, the palmitic acid and oleic acid are present in a ratio of about 1.5:1 (palmitic acid:oleic acid). In another embodiment, the palmitic acid and oleic acid are present in a ratio of about 2:1 (palmitic acid:oleic acid). In one embodiment, the palmitic acid and oleic acid are present in a ratio of about 3:1 (palmitic acid:oleic acid). In another embodiment, the palmitic acid and oleic acid are present in a ratio of about 4:1 (palmitic acid:oleic acid). In one embodiment, the palmitic acid and oleic acid are present in a ratio of about 2.3:1 (palmitic acid:oleic acid). In one embodiment, the palmitic acid and oleic acid are present in a ratio of about 3:7 (palmitic acid:oleic acid). In one embodiment, the palmitic acid and oleic acid are present in a ratio of about 7:3 (palmitic acid:oleic acid). In one embodiment, the palmitic acid and oleic acid are present in a ratio of about 2.5:1 (palmitic acid:oleic acid). In another embodiment, the palmitic acid and oleic acid are present in a ratio of about 1:2.5 (palmitic acid:oleic acid). In another embodiment, the palmitic acid and oleic acid are present in a ratio of about 1:0 (palmitic acid:oleic acid). In another embodiment, the palmitic acid and oleic acid are present in a ratio of about) 0:1 (palmitic acid:oleic acid).

In one embodiment in the treatment or prevention of hyperglycemia, the treating or preventing comprises lowering the subject's blood glucose concentration by about 10%. In another embodiment, the treating or preventing comprises lowering the subject's blood glucose concentration by about 15%. In another embodiment, the treating or preventing comprises lowering the subject's blood glucose concentration by about 20%. In one embodiment, the treating or preventing comprises lowering the subject's blood glucose concentration by about 25%. In another embodiment, the treating or preventing comprises lowering the subject's blood glucose concentration by about 30%. In one embodiment, the treating or preventing comprises lowering the subject's blood glucose concentration by about 35%. In another embodiment, the treating or preventing comprises lowering the subject's blood glucose concentration by about 40%. In one embodiment, the treating or preventing comprises lowering the subject's blood glucose concentration by about 45%. In another embodiment, the treating or preventing comprises lowering the subject's blood glucose concentration by about 50%.

In another aspect, the present invention provides for a method of treating or preventing hyperglycemia, the method comprising administering to a subject in need thereof a therapeutically effective amount of one or more compounds, thereby treating or preventing the hyperglycemia. In one embodiment, the compound is coconut oil. In another embodiment, the compound is olive oil. In another embodiment, the compound is a combination of olive oil and coconut oil.

In another aspect, the present invention provides for a method of treating or preventing hyperglycemia, the method comprising administering to a subject in need thereof a therapeutically effective amount of a composition comprising olive oil and coconut oil, thereby treating or preventing the hyperglycemia.

In one embodiment, in the treatment or prevention of hyperglycemia, the olive oil and coconut oil are present in a ratio of about 2.3:1 olive oil:coconut oil. In another embodiment, the olive oil and coconut oil are present in a ratio of about 1:1 olive oil:coconut oil. In one embodiment, the olive oil and coconut oil are present in a ratio of about 3:1 olive oil:coconut oil. In another embodiment, the olive oil and coconut oil are present in a ratio of about 1:3 olive oil:coconut oil.

In one embodiment, the olive oil and the coconut oil have a synergistic effect on hyperglycemia.

In one embodiment, in the treatment or prevention of hyperglycemia, the treating or preventing comprises lowering the subject's blood glucose concentration by about 10%. In another embodiment, the treating or preventing comprises lowering the subject's blood glucose concentration by about 15%. In one embodiment, the treating or preventing comprises lowering the subject's blood glucose concentration by about 20%. In another embodiment, the treating or preventing comprises lowering the subject's blood glucose concentration by about 25%. In one embodiment, the treating or preventing comprises lowering the subject's blood glucose concentration by about 30%. In another embodiment, the treating or preventing comprises lowering the subject's blood glucose concentration by about 35%. In one embodiment, the treating or preventing comprises lowering the subject's blood glucose concentration by about 40%. In another embodiment, the treating or preventing comprises lowering the subject's blood glucose concentration by about 45%. In one embodiment, the treating or preventing comprises lowering the subject's blood glucose concentration by about 50%.

Treatment and Prevention of Hypertension

In another aspect, the present invention provides for a method of treating or preventing hypertension, the method comprising administering to a subject in need thereof a therapeutically effective amount of one or more compounds isolated from *Eucalyptus camaldulensis*, thereby treating or preventing the hypertension. In one embodiment, the compound is oleic acid, palmitic acid or both.

In one embodiment, in the treatment or prevention of hypertension, the subject has been diagnosed with diabetes mellitus.

In another aspect, the present invention provides for a method of treating or preventing hypertension, the method comprising administering to a subject in need thereof a therapeutically effective amount of a composition comprising oleic acid and palmitic acid, thereby treating or preventing the hypertension.

In one embodiment, in the treatment or prevention of hypertension, the oleic acid and palmitic acid are extracted from *Eucalyptus camaldulensis*. In one embodiment, the oleic acid and palmitic acid are present in a ratio of about 1:1 (oleic acid:palmitic acid). In another embodiment, the oleic acid and palmitic acid are present in a ratio of about 1.5:1 (oleic acid:palmitic acid). In another embodiment, the oleic acid and palmitic acid are present in a ratio of about 2:1 (oleic acid:palmitic acid). In one embodiment, the oleic acid and palmitic acid are present in a ratio of about 3:1 (oleic acid:palmitic acid). In another embodiment, the oleic acid and palmitic acid are present in a ratio of about 4:1 (oleic acid:palmitic acid). In one embodiment, the oleic acid and palmitic acid are present in a ratio of about 2.3:1 (oleic acid:palmitic acid). In one embodiment, the oleic acid and palmitic acid are present in a ratio of about 3:7 (oleic acid:palmitic acid). In one embodiment, the oleic acid and palmitic acid are present in a ratio of about 7:3 (oleic acid:palmitic acid). In one embodiment, the oleic acid and palmitic acid are present in a ratio of about 2.5:1 (oleic acid:palmitic acid). In one embodiment, the oleic acid and palmitic acid are present in a ratio of about 1:2.5 (oleic acid:palmitic acid). In one embodiment, the oleic acid and palmitic acid are present in a ratio of about 1:0 (oleic acid:palmitic acid). In one embodiment, the oleic acid and palmitic acid are present in a ratio of about 0:1 (oleic acid:palmitic acid).

In another embodiment, in the treatment or prevention of hypertension, the palmitic acid and oleic acid are present in a ratio of about 1:1 (palmitic acid:oleic acid). In another embodiment, the palmitic acid and oleic acid are present in a ratio of about 1.5:1 (palmitic acid:oleic acid). In another embodiment, the palmitic acid and oleic acid are present in a ratio of about 2:1 (palmitic acid:oleic acid). In one embodiment, the palmitic acid and oleic acid are present in a ratio of about 3:1 (palmitic acid:oleic acid). In another embodiment, the palmitic acid and oleic acid are present in a ratio of about 4:1 (palmitic acid:oleic acid). In one embodiment, the palmitic acid and oleic acid are present in a ratio of about 2.3:1 (palmitic acid:oleic acid). In one embodiment, the palmitic acid and oleic acid are present in a ratio of about 3:7 (palmitic acid:oleic acid). In one embodiment, the palmitic acid and oleic acid are present in a ratio of about 7:3 (palmitic acid:oleic acid). In one embodiment, the palmitic acid and oleic acid are present in a ratio of about 2.5:1 (palmitic acid:oleic acid). In another embodiment, the palmitic acid and oleic acid are present in a ratio of about 1:2.5 (palmitic acid:oleic acid). In another embodiment, the palmitic acid and oleic acid are present in a ratio of about 1:0 (palmitic acid:oleic acid). In another embodiment, the palmitic acid and oleic acid are present in a ratio of about) 0:1 (palmitic acid:oleic acid).

In one embodiment, the oleic acid and palmitic acid are extracted from the leaves of *Eucalyptus camaldulensis*. In another embodiment, the oleic acid and the palmitic acid have a synergistic effect on hypertension.

In another aspect, the present invention provides for a method of treating or preventing hypertension, the method comprising administering to a subject in need thereof a therapeutically effective amount of one or more compounds, thereby treating or preventing the hypertension. In one embodiment, the compound is coconut oil. In another embodiment, the compound is olive oil. In another embodiment, the compound is a combination of olive oil and coconut oil.

In another aspect, the present invention provides for a method of treating or preventing hypertension, the method comprising administering to a subject in need thereof a therapeutically effective amount of a composition comprising olive oil and coconut oil, thereby treating or preventing the hypertension.

In one embodiment, in the treatment or prevention of hypertension, the olive oil and coconut oil are present in a ratio of about 2.3:1 olive oil:coconut oil. In another embodiment, the olive oil and coconut oil are present in a ratio of about 1:1 olive oil:coconut oil. In one embodiment, the olive oil and coconut oil are present in a ratio of about 3:1 olive oil:coconut oil. In another embodiment, the olive oil and coconut oil are present in a ratio of about 1:3 olive oil:coconut oil.

In one embodiment, in the treatment or prevention of hypertension, the treating or preventing comprises reducing the subject's systolic blood pressure (SBP) by about 10%. In another embodiment, the treating or preventing comprises reducing the subject's systolic blood pressure (SBP) by about 15%. In one embodiment, the treating or preventing comprises reducing the subject's systolic blood pressure (SBP) by about 20%. In another embodiment, the treating or preventing comprises reducing the subject's systolic blood pressure (SBP) by about 25%. In one embodiment, the treating or preventing comprises reducing the subject's systolic blood pressure (SBP) by about 30%. In another embodiment, the treating or preventing comprises reducing the subject's systolic blood pressure (SBP) by about 35%. In one embodiment, the treating or preventing comprises reducing the subject's systolic blood pressure (SBP) by about 40%. In another embodiment, the treating or preventing comprises reducing the subject's systolic blood pressure (SBP) by about 45%. In one embodiment, the treating or preventing comprises reducing the subject's systolic blood pressure (SBP) by about 50%. In another embodiment, the treating or preventing comprises reducing the subject's systolic blood pressure (SBP) by about 55%.

In one embodiment, in the treatment or prevention of hypertension, the treating or preventing comprises reducing the subject's diastolic blood pressure (DBP) by about 5%. In another embodiment, the treating or preventing comprises reducing the subject's diastolic blood pressure (DBP) by about 10%. In one embodiment, the treating or preventing comprises reducing the subject's diastolic blood pressure (DBP) by about 15%. In another embodiment, the treating or preventing comprises reducing the subject's diastolic blood pressure (DBP) by about 20%. In one embodiment, the treating or preventing comprises reducing the subject's diastolic blood pressure (DBP) by about 25%. In another embodiment, the treating or preventing comprises reducing the subject's diastolic blood pressure (DBP) by about 30%. In one embodiment, the treating or preventing comprises reducing the subject's diastolic blood pressure (DBP) by about 35%. In another embodiment, the treating or preventing comprises reducing the subject's diastolic blood pressure (DBP) by about 40%. In one embodiment, the treating or preventing comprises reducing the subject's diastolic blood pressure (DBP) by about 45%.

In one embodiment, in the treatment or prevention of hypertension, the treating or preventing comprises reducing the subject's heart rate by about 5%. In another embodiment, the treating or preventing comprises reducing the subject's heart rate by about 10%. In one embodiment, the treating or preventing comprises reducing the subject's heart rate by about 15%. In another embodiment, the treating or preventing comprises reducing the subject's heart rate by about 20%. In one embodiment, the treating or preventing comprises reducing the subject's heart rate by about 25%. In another embodiment, the treating or preventing comprises reducing the subject's heart rate by about 30%. In one embodiment, the treating or preventing comprises reducing the subject's heart rate by about 35%. In another embodiment, the treating or preventing comprises reducing the subject's heart rate by about 40%.

Part II. Eicosane Used for the Treatment of Hyperglycemia and Hypertension

Treatment and Prevention of Hyperglycemia

In one aspect, the present invention provides for a method of treating or preventing hyperglycemia, the method comprising administering to a subject in need thereof a therapeutically effective amount of one or more compounds isolated from *Eucalyptus camaldulensis*, thereby treating or preventing the hyperglycemia.

In one embodiment, in the treatment or prevention of hyperglycemia, the subject has been diagnosed with diabetes mellitus. In one embodiment, the compound is eicosane.

In another aspect, the present invention provides for a method of treating or preventing hyperglycemia, the method comprising administering to a subject in need thereof a therapeutically effective amount of one or more compounds, wherein at least one compound is a hydrocarbon, thereby treating or preventing the hyperglycemia.

In one embodiment, the hydrocarbon is eicosane. In another embodiment, the hydrocarbon is isolated from *Eucalyptus camaldulensis*.

In one embodiment, in the treatment or prevention of hyperglycemia, the treating or preventing comprises lowering the subject's blood glucose concentration by about 10%. In another embodiment, the treating or preventing comprises lowering the subject's blood glucose concentration by about 15%. In one embodiment, the treating or preventing comprises lowering the subject's blood glucose concentration by about 20%. In another embodiment, the treating or preventing comprises lowering the subject's blood glucose concentration by about 25%. In one embodiment, the treating or preventing comprises lowering the subject's blood glucose concentration by about 30%. In another embodiment, the treating or preventing comprises lowering the subject's blood glucose concentration by about 35%. In one embodiment, the treating or preventing comprises lowering the subject's blood glucose concentration by about 40%. In another embodiment, the treating or preventing comprises lowering the subject's blood glucose concentration by about 45%. In one embodiment, the treating or preventing comprises lowering the subject's blood glucose concentration by about 50%.

In one embodiment, in the treatment or prevention of hyperglycemia, the treating or preventing comprises increasing the subject's blood insulin levels by about 20%. In one embodiment, the treating or preventing comprises increasing the subject's blood insulin levels by about 30%. In another embodiment, the treating or preventing comprises increasing the subject's blood insulin levels by about 40%. In one embodiment, the treating or preventing comprises increasing the subject's blood insulin levels by about 50%. In another embodiment, the treating or preventing comprises increasing the subject's blood insulin levels by about 60%. In one embodiment, the treating or preventing comprises increasing the subject's blood insulin levels by about 70%. In another embodiment, the treating or preventing comprises increasing the subject's blood insulin levels by about 80%. In one embodiment, the treating or preventing comprises increasing the subject's blood insulin levels by about 90%.

Treatment and Prevention of Hypertension

In another aspect, the present invention provides for a method of treating or preventing hypertension, the method comprising administering to a subject in need thereof a therapeutically effective amount of one or more compounds isolated from *Eucalyptus camaldulensis*, thereby treating or preventing the hypertension.

In one embodiment, in the treatment or prevention of hypertension, the subject has been diagnosed with diabetes mellitus. In one embodiment, the compound is eicosane.

In another aspect, the present invention provides for a method of treating or preventing hypertension, the method comprising administering to a subject in need thereof a therapeutically effective amount of one or more compounds, wherein at least one compound is a hydrocarbon, thereby treating or preventing the hypertension.

In one embodiment, the hydrocarbon is eicosane. In another embodiment, the hydrocarbon is isolated from *Eucalyptus camaldulensis*.

In one embodiment, in the treatment or prevention of hypertension, the treating or preventing comprises reducing the subject's systolic blood pressure (SBP) by about 15%. In another embodiment, the treating or preventing comprises reducing the subject's systolic blood pressure (SBP) by about 20%. In one embodiment, the treating or preventing comprises reducing the subject's systolic blood pressure (SBP) by about 25%. In one embodiment, the treating or preventing comprises reducing the subject's systolic blood pressure (SBP) by about 30%. In another embodiment, the treating or preventing comprises reducing the subject's systolic blood pressure (SBP) by about 35%. In one embodiment, the treating or preventing comprises reducing the subject's systolic blood pressure (SBP) by about 40%. In another embodiment, the treating or preventing comprises reducing the subject's systolic blood pressure (SBP) by about 45%. In one embodiment, the treating or preventing comprises reducing the subject's systolic blood pressure (SBP) by about 50%.

In one embodiment, in the treatment or prevention of hypertension, the treating or preventing comprises reducing the subject's diastolic blood pressure (DBP) by about 15%. In another embodiment, the treating or preventing comprises reducing the subject's diastolic blood pressure (DBP) by about 20%. In one embodiment, the treating or preventing comprises reducing the subject's diastolic blood pressure (DBP) by about 25%. In one embodiment, the treating or preventing comprises reducing the subject's diastolic blood pressure (DBP) by about 30%. In another embodiment, the treating or preventing comprises reducing the subject's diastolic blood pressure (DBP) by about 35%. In one embodiment, the treating or preventing comprises reducing the subject's diastolic blood pressure (DBP) by about 40%.

In one embodiment, in the treatment or prevention of hypertension, the treating or preventing comprises reducing the subject's heart rate by about 5%. In another embodiment, the treating or preventing comprises reducing the subject's heart rate by about 10%. In one embodiment, the treating or preventing comprises reducing the subject's heart rate by about 15%. In one embodiment, the treating or preventing comprises reducing the subject's heart rate by about 20%. In another embodiment, the treating or preventing comprises reducing the subject's heart rate by about 25%. In one embodiment, the treating or preventing comprises reducing the subject's heart rate by about 30%.

In one embodiment, in the treatment or prevention of hypertension, the treating or preventing comprises reducing the subject's mean arterial blood pressure by about 10%. In another embodiment, the treating or preventing comprises reducing the subject's mean arterial blood pressure by about 15%. In one embodiment, the treating or preventing comprises reducing the subject's mean arterial blood pressure by about 20%. In another embodiment, the treating or preventing comprises reducing the subject's mean arterial blood pressure by about 25%. In one embodiment, the treating or preventing comprises reducing the subject's mean arterial blood pressure by about 30%. In another embodiment, the treating or preventing comprises reducing the subject's mean arterial blood pressure by about 35%. In one embodiment, the treating or preventing comprises reducing the subject's mean arterial blood pressure by about 40%. In another embodiment, the treating or preventing comprises reducing the subject's mean arterial blood pressure by about 45%.

Compounds

Part I. Fatty Acids Used for the Treatment of Hyperglycemia and Hypertension

The present disclosure provides methods for the treatment and/or prevention of hyperglycemia and/or hypertension, which comprise administration of one or more compounds. The compounds of the invention include compounds isolated from *Eucalyptus camaldulensis*, including, but not limited to, oleic acid and palmitic acid. The compounds of the invention include compounds that are commercially available, including, but not limited to, oleic acid, olive oil, coconut oil and palmitic acid.

The structures of oleic acid and palmitic acid are well known in the art. The triglyceride composition of coconut oil is well known in the art. The structures of the triglycerides comprised in coconut oil, including, but not limited to, palmitic acid, are well known in the art. The triglyceride composition of olive oil is well known in the art. The structures of the triglycerides comprised in olive oil, including, but not limited to, oleic acid, are well known in the art.

Part II. Eicosane Used for the Treatment of Hyperglycemia and Hypertension

The present disclosure provides methods for the treatment and/or prevention of hyperglycemia and/or hypertension, which comprise administration of one or more compounds. The compounds of the invention include compounds isolated from *Eucalyptus camaldulensis*, including, but not limited to, eicosane.

The structure of eicosane is well known in the art.

Pharmaceutical Compositions and Administration for Therapy

Compounds of the invention can be administered to the subject once (e.g., as a single injection or deposition). Alternatively, compounds of the invention can be administered once or twice daily to a subject in need thereof for a period of from about two to about twenty-eight days, or from about seven to about ten days. Compounds of the invention can also be administered once or twice daily to a subject for a period of 1, 2, 3, 4, 5, 6, 7, 8, 9, 10, 11, 12 times per year, or a combination thereof. Furthermore, compounds of the invention can be co-administered with another therapeutic. Where a dosage regimen comprises multiple administrations, the effective amount of the compound(s) administered to the subject can comprise the total amount of the compound(s) administered over the entire dosage regimen.

Compounds can be administered to a subject by any means suitable for delivering the compounds to cells of the subject. For example, compounds can be administered by methods suitable to transfect cells. Transfection methods for eukaryotic cells are well known in the art, and include direct injection of a nucleic acid into the nucleus or pronucleus of a cell; electroporation; liposome transfer or transfer mediated by lipophilic materials; receptor mediated nucleic acid delivery, bioballistic or particle acceleration; calcium phosphate precipitation, and transfection mediated by viral vectors.

The compositions of this invention can be formulated and administered to reduce the symptoms associated with hyperglycemia and/or hypertension by any means that produces contact of the active ingredient with the agent's site of action in the body of a subject, such as a human or animal (e.g., a dog, cat, or horse). They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The compounds of the invention may be administered to a subject in an amount effective to treat or prevent hyperglycemia and/or hypertension. One of skill in the art can readily determine what will be an effective amount of the compounds of the invention to be administered to a subject, taking into account whether the compound is being used prophylactically or therapeutically, and taking into account other factors such as the age, weight and sex of the subject, any other drugs that the subject may be taking, any allergies or contraindications that the subject may have, and the like. For example, an effective amount can be determined by the skilled artisan using known procedures, including analysis of titration curves established in vitro or in vivo. Also, one of skill in the art can determine the effective dose from performing pilot experiments in suitable animal model species and scaling the doses up or down depending on the subjects weight etc. Effective amounts can also be determined by performing clinical trials in individuals of the same species as the subject, for example starting at a low dose and gradually increasing the dose and monitoring the effects on hyperglycemia and/or hypertension. Appropriate dosing regimens can also be determined by one of skill in the art without undue experimentation, in order to determine, for example, whether to administer the agent in one single dose or in multiple doses, and in the case of multiple doses, to determine an effective interval between doses.

A therapeutically effective dose of a compound that treats or prevents hyperglycemia and/or hypertension can depend upon a number of factors known to those of ordinary skill in the art. The dose(s) of the compounds can vary, for example, depending upon the identity, size, and condition of the subject or sample being treated, further depending upon the route by which the composition is to be administered, if applicable, and the effect which the practitioner desires the compound to have upon the target of interest. These amounts can be readily determined by a skilled artisan. These amounts include, for example, mg or microgram (µg) amounts per kilogram (kg) of subject weight, such as about 1 mg/kg, about 2 mg/kg, about 3 mg/kg, about 4 mg/kg, about 5 mg/kg, about 6 mg/kg, about 7 mg/kg, about 8 mg/kg, about 9 mg/kg or about 10 mg/kg, or about 11 mg/kg, or about 12 mg/kg, or about 13 mg/kg, or about 14 mg/kg, or about 15 mg/kg, or about 16 mg/kg, or about 17 mg/kg, or about 18 mg/kg, or about 19 mg/kg, or about 20 mg/kg, or about 21 mg/kg, or about 22 mg/kg, or about 23 mg/kg, or about 24 mg/kg, or about 25 mg/kg, or about 26 mg/kg, or about 27 mg/kg, or about 28 mg/kg, or about 29 mg/kg, or about 30 mg/kg, or about 31 mg/kg, or about 32 mg/kg, or about 33 mg/kg, or about 34 mg/kg, or about 35 mg/kg, or about 36 mg/kg, or about 37 mg/kg, or about 38 mg/kg, or about 39 mg/kg, or about 40 mg/kg, or about 41 mg/kg, or about 42 mg/kg, or about 53 mg/kg, or about 44 mg/kg, or about 45 mg/kg, or about 46 mg/kg, or about 47 mg/kg, or about 48 mg/kg, or about 49 mg/kg, or about 50 mg/kg, or about 51 mg/kg, or about 52 mg/kg, or about 53 mg/kg, or about 54 mg/kg, or about 55 mg/kg, or between about 1 mg/kg to 2 mg/kg, 2 mg/kg to 3 mg/kg, 3 mg/kg to 4 mg/kg, 4 mg/kg to 5 mg/kg, 5 mg/kg to 6 mg/kg, 6 mg/kg to 7 mg/kg, 7 mg/kg to 8 mg/kg, 8 mg/kg to 9 mg/kg, or 9 mg/kg to 10 mg/kg, or between about 10 mg/kg to 15 mg/kg, or between about 15 mg/kg to 20 mg/kg, or between about 20 mg/kg to 25 mg/kg, or between about 25 mg/kg to 30 mg/kg, or between about 30 mg/kg to 35 mg/kg, or between about 35 mg/kg to 40 mg/kg, or between about 40 mg/kg to 45 mg/kg, or between about 45 mg/kg to 50 mg/kg, or between about 50 mg/kg to 55 mg/kg, or between about 55 mg/kg to 60 mg/kg, or any range in between. These amounts also include a unit dose of a compound, for example, at least about 1 mg, 2 mg, 5 mg, 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 750 mg, 800 mg, 850 mg, 900 mg, 1 g, 1.5 g, 2 g, 2.5 g, 3 g, 3.5 g, 4 g, 4.5 g, 5 g, 5.5 g, 6 g, or more. Any of the therapeutic applications described herein can be applied to any subject in need of such therapy, including, for example, a mammal such as a dog, a cat, a cow, a horse, a rabbit, a monkey, a pig, a sheep, a goat, or a human.

Pharmaceutical compositions for use in accordance with the invention can be formulated in conventional manner using one or more physiologically acceptable carriers or excipients. The therapeutic compositions of the invention can be formulated for a variety of routes of administration, including systemic and topical or localized administration. Techniques and formulations generally can be found in *Remmington's Pharmaceutical Sciences*, Meade Publishing Co., Easton, Pa. (20$^{th}$ Ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers such as Hank's solution or Ringer's solution. In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

A pharmaceutical composition containing a compound of the invention can be administered in conjunction with a pharmaceutically acceptable carrier, for any of the therapeutic effects discussed herein. The compositions can be administered alone or in combination with at least one other agent, such as a stabilizing compound, which can be administered in any sterile, biocompatible pharmaceutical carrier including, but not limited to, saline, buffered saline, dextrose, and water. The compositions can be administered to a patient alone, or in combination with other agents, drugs or hormones.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyethylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it can be useful to include isotonic agents, for example, sugars, polyalcohols such as mannitol, sorbitol, sodium chloride in the composition. Prolonged absorption of injectable compositions can be brought about by incorporating an agent which delays absorption, for example, aluminum monostearate and gelatin.

Sterile injectable solutions can be prepared by incorporating the compound (e.g., a small molecule, peptide or antibody) in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. In some embodiments, the compound can be applied via transdermal delivery systems, which slowly releases the active compound for percutaneous absorption. Permeation enhancers can be used to facilitate transdermal penetration of the active factors in the conditioned media. Transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Administration of the compound is not restricted to a single route, but may encompass administration by multiple routes. For instance, exemplary administrations by multiple routes include, among others, a combination of intradermal and intramuscular administration, or intradermal and subcutaneous administration. Multiple administrations may be sequential or concurrent. Other modes of application by multiple routes will be apparent to the skilled artisan.

The compounds of the invention may be formulated into compositions for administration to subjects for the treatment and/or prevention of hyperglycemia and/or hypertension. Such compositions may comprise the compounds of the invention in admixture with one or more pharmaceutically acceptable diluents and/or carriers and optionally one or more other pharmaceutically acceptable additives. The pharmaceutically-acceptable diluents and/or carriers and any other additives must be "acceptable" in the sense of being compatible with the other ingredients of the composition and not deleterious to the subject to whom the composition will be administered. One of skill in the art can readily formulate the compounds of the invention into compositions suitable for administration to subjects, such as human subjects, for example using the teaching a standard text such as Remington's Pharmaceutical Sciences, 18th ed, (Mack Publishing Company: Easton, Pa., 1990), pp. 1635-36), and by taking into account the selected route of delivery.

Examples of diluents and/or carriers and/or other additives that may be used include, but are not limited to, water, glycols, oils, alcohols, aqueous solvents, organic solvents, DMSO, saline solutions, physiological buffer solutions, peptide carriers, starches, sugars, preservatives, antioxidants, coloring agents, pH buffering agents, granulating agents, lubricants, binders, disintegrating agents, emulsifiers, binders, excipients, extenders, glidants, solubilizers, stabilizers, surface active agents, suspending agents, tonicity agents, viscosity-altering agents, carboxymethyl cellulose, crystalline cellulose, glycerin, gum arabic, lactose, magnesium stearate, methyl cellulose, powders, saline, sodium alginate. The combination of diluents and/or carriers and/or other additives used can be varied taking into account the nature of the active agents used (for example the solubility and stability of the active agents), the route of delivery (e.g. oral, parenteral, etc.), whether the agents are to be delivered over an extended period (such as from a controlled-release capsule), whether the agents are to be co-administered with other agents, and various other factors. One of skill in the art will readily be able to formulate the compounds for the desired use without undue experimentation.

The compounds of the invention may be administered to a subject by any suitable method that allows the agent to exert its effect on the subject in vivo. For example, the compositions may be administered to the subject by known procedures including, but not limited to, by oral administration, sublingual or buccal administration, parenteral administration, transdermal administration, via inhalation, via nasal delivery, vaginally, rectally, and intramuscularly. The compounds of the invention may be administered parenterally, or by epifascial, intracapsular, intracutaneous, subcutaneous, intradermal, intrathecal, intramuscular, intraperitoneal, intrasternal, intravascular, intravenous, parenchymatous, or sublingual delivery. Delivery may be by injection, infusion, catheter delivery, or some other means, such as by tablet or spray. In one embodiment, the compounds of the invention are administered to the subject by way of delivery directly to the muscle tissue of interest, such as by way of a catheter inserted into, or in the proximity of the subject's muscle of interest, or by using delivery vehicles capable of targeting the drug to the muscle.

For oral administration, a formulation of the compounds of the invention may be presented as capsules, tablets, powders, granules, or as a suspension or solution. The formulation may contain conventional additives, such as lactose, mannitol, cornstarch or potato starch, binders, crystalline cellulose, cellulose derivatives, acacia, cornstarch, gelatins, disintegrators, potato starch, sodium carboxymethylcellulose, dibasic calcium phosphate, anhydrous or sodium starch glycolate, lubricants, and/or or magnesium stearate.

For parenteral administration (i.e., administration by through a route other than the alimentary canal), the compounds of the invention may be combined with a sterile aqueous solution that is isotonic with the blood of the subject. Such a formulation may be prepared by dissolving the active ingredient in water containing physiologically-compatible substances, such as sodium chloride, glycine and the like, and having a buffered pH compatible with physiological conditions, so as to produce an aqueous solution, then rendering the solution sterile. The formulation may be presented in unit or multi-dose containers, such as sealed ampoules or vials. The formulation may be delivered by injection, infusion, or other means known in the art.

For transdermal administration, the compounds of the invention may be combined with skin penetration enhancers, such as propylene glycol, polyethylene glycol, isopropanol, ethanol, oleic acid, N-methylpyrrolidone and the like, which increase the permeability of the skin to the compounds of the invention and permit the compounds to penetrate through the skin and into the bloodstream. The compounds of the invention also may be further combined with a polymeric substance, such as ethylcellulose, hydroxypropyl cellulose, ethylene/vinylacetate, polyvinyl pyrrolidone, and the like, to provide the composition in gel form, which are dissolved in a solvent, such as methylene chloride, evaporated to the desired viscosity and then applied to backing material to provide a patch.

In some embodiments, the compounds of the invention are provided in unit dose form such as a tablet, capsule or single-dose injection or infusion vial.

Combination Therapy

According to the methods of the invention, a compound of the invention can be administered to a subject either as a single agent, or in combination with one or more other agents. In one embodiment, a compound of the invention is administered to a subject as a single agent. In one embodiment, a compound of the invention is administered to a subject alone. In one embodiment, a compound of the invention is administered to a subject in combination with one or more other agents.

In certain embodiments, a compound of the invention may be used in combination with other agents that are used for the treatment or prevention of hyperglycemia and/or hypertension. In certain embodiments, a compound of the invention may be used in combination with other agents that are not used for the treatment or prevention of hyperglycemia and/or hypertension. In one embodiment, the hyperglycemia and/or hypertension is associated with diabetes mellitus. In another embodiment, the hyperglycemia and/or hypertension is not associated with diabetes mellitus.

In one embodiment, a compound of the invention may be delivered to a subject as part of the same pharmaceutical composition or formulation containing one or more additional active agents. In another embodiment, a compound of the invention may be delivered to a subject in a composition or formulation containing only that active agent, while one or more other agents are administered to the subject in one or more separate compositions or formulations. In one embodiment, the other agents are not used for the treatment or prevention of hyperglycemia and/or hypertension. In another embodiment, the other agents are used for the treatment or prevention of hyperglycemia and/or hypertension. In one embodiment, the hyperglycemia and/or hypertension is associated with diabetes mellitus. In another embodiment, the hyperglycemia and/or hypertension is not associated with diabetes mellitus.

A compound of the invention and the other agents that are used for the treatment or prevention of hyperglycemia and/or hypertension may be administered to the subject at the same time, or at different times. A compound of the invention and the other agents that are not used for the treatment or prevention of hyperglycemia and/or hypertension may be administered to the subject at the same time, or at different times. For example, a compound of the invention and the other agents may be administered within minutes, hours, days, weeks, or months of each other, for example as part of the overall treatment regimen of a subject. In some embodiments, a compound of the invention may be administered prior to the administration of other agents. In other embodiments, a compound of the invention may be administered subsequent to the administration of other agents.

A compound of the invention may also be used in combination with known therapies for hyperglycemia and/or hypertension.

Compounds of the invention, as described above, including, but not limited to, compounds isolated from the plant *Eucalyptus camaldulensis*, such as oleic acid, palmitic acid and eicosane, may be used in combination with each other for the treatment or prevention of hyperglycemia and/or hypertension. In one embodiment, the hyperglycemia and/or hypertension is associated with diabetes mellitus. In another embodiment, the hyperglycemia and/or hypertension is not associated with diabetes mellitus.

In some embodiments, the administration of a compound of the invention in combination with one or more other agents has an additive effect, in comparison with administration of the compound of the invention alone, or administration of the one or more other agents alone. In other embodiments, the administration of a compound of the invention in combination with one or more other agents has a synergistic effect, in comparison with administration of the compound of the invention alone, or administration of the one or more other agents alone. In some embodiments, the administration of a compound of the invention in combination with one or more other agents can help reduce side effects, in comparison with administration of the compound of the invention alone, or administration of the one or more other agents alone.

In some embodiments, the compound of the invention is used as an adjuvant therapy. In other embodiments, the compound of the invention is used in combination with an adjuvant therapy.

Subjects

According to the methods of the invention, the subject or patient can be any animal that has or is diagnosed with hyperglycemia and/or hypertension. In one embodiment, the hyperglycemia and/or hypertension is associated with diabetes mellitus. In another embodiment, the hyperglycemia and/or hypertension is not associated with diabetes mellitus.

According to the methods of the invention, the subject or patient can be any animal that is predisposed to or is at risk of developing hyperglycemia and/or hypertension. In preferred embodiments, the subject is a human subject. In some embodiments, the subject is a rodent, such as a mouse. In some embodiments, the subject is a cow, pig, sheep, goat, cat, horse, dog, and/or any other species of animal used as livestock or kept as pets.

In some embodiments, the subject is already suspected to have hyperglycemia and/or hypertension. In other embodiments, the subject is being treated for hyperglycemia and/or hypertension, before being treated according to the methods of the invention. In other embodiments, the subject is not being treated for hyperglycemia and/or hypertension, before being treated according to the methods of the invention.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

The Isolate of the Hypoglycemic Principles of *Eucalyptus camaldulensis* Showing a Similar Effect as Metformin The objective of this study is to isolate the hypoglycaemic compound(s) from crude extracts of the leaves of *Eucalyptus camaldulensis* and subsequently purify and elucidate its structure. The objective is also to observe the efficacy of the compound(s) by a comparison with a known oral hypoglycaemic agent, metformin.

Crude hexane, ethyl acetate, and methanol extracts (50 mg/kg BW) were administered intravenously to normoglycaemic Sprague-Dawley rats. The Oral Glucose Tolerance Test (OGTT) was then carried out using the Accu-Check Advantage II glucose kit to examine their effect on blood glucose concentration. Chromatography was then used to purify the active crude hexane extract, and the most hypoglycaemic fractions, yielded compounds FR2DBW (30 mg/kg BW) and FR1DBY (50 mg/kg BW) whose structures were elucidated by spectroscopic analysis. A comparison was carried out using metformin (25 mg/kg BW).

The glucose tolerance curve for the crude hexane extract showed a significant lowering of the blood glucose concentration at the 90 minutes interval (4.71±0.19 mmol/L vs 6.1±0.68 mmol/L dimethyl sulfoxide, DMSO). Compounds FR1DBY and FR2DBW were isolated from Fractions 1 and 2 respectively after purification by column chromatography; these were the most hypoglycaemic fractions ($p<0.05$). FR1DBY and FR2DBW elicited the same effect as Metformin ($p=0.36$ and 0.94 respectively at 90 minute interval), significantly lowering the blood glucose concentration. Spectroscopy was then done to deduce their structures.

The hypoglycaemic principles (FR2DBW and FR1DBY) that were isolated from the crude hexane extract of *Eucalyptus camaldulensis* were fatty acids.

Example 2

Hypoglycemic Compounds Isolated from *Eucalyptus camaldulensis* Showing a Similar Effect with Metformin River Red Rum or *Eucalyptus camaldulensis*, is a fast-growing evergreen from the Myrtaceae family being investigated for the hypoglycaemic principle present within the leaves. Ethnomedicinal plants have formed the basis of various treatments in the medical world today, for example, diabetes. This study aims to isolate the hypoglycaemic compound(s) from crude extracts of the leaves of the said plant and subsequently purify and elucidate its structure, and also, to observe the efficacy of the compound(s) by a comparison with a known oral hypoglycaemic agent, metformin.

Crude hexane, ethyl acetate, and methanol extracts (50 mg/kg BW) were administered intravenously to normoglycaemic Sprague-Dawley rats. The Oral Glucose Tolerance Test (OGTT) was then carried out using the Accu-Check Advantage II glucose kit to examine their effect on blood glucose concentration. Chromatography was then used to purify the active crude hexane extract, and the most hypoglycaemic fractions, yielded compounds FR2DBW (30 mg/kg BW) and FR1DBY (50 mg/kg BW) whose structures were elucidated by spectroscopic analysis. A comparison was carried out using metformin (25 mg/kg BW).

The glucose tolerance curve for the crude hexane extract showed a significant lowering of the blood glucose concentration at the 90 minutes interval (4.71±0.19 mmol/L vs 6.1±0.68 mmol/L dimethyl sulfoxide, DMSO). Compounds FR1DBY and FR2DBW were isolated from Fractions 1 and 2 respectively after purification by column chromatography; these were the most hypoglycaemic fractions ($p<0.05$). FR1DBY and FR2DBW elicited the same effect as Metformin ($p=0.36$ and 0.94 respectively at 90 minute interval), significantly lowering the blood glucose concentration. Spectroscopy was then done to deduce their structures.

The hypoglycaemic principles (FR2DBW and FR1DBY) that were isolated from the crude hexane extract of *Eucalyptus camaldulensis* were fatty acids.

Example 3

Compounds Isolated from *Eucalyptus camaldulensis* Showing a Dose Dependent Hypoglycemic Effect Within the Caribbean, diabetes mellitus is the leading cause of secondary blindness, and in Jamaica, it is one of the leading causes of death. Over 400 traditional plant treatments for diabetes mellitus have been recorded, with only a small number receiving scientific and medicinal appraisal. These are predominantly used in under-developed regions, thus, research into alternative treatment for diabetes may provide valuable clues for the development of new oral hypoglycaemic agents. As a result, this investigation aims to validate the ethnomedicinal use of the *Eucalyptus camaldulensis* associated with the treatment of hyperglycaemia and the most effective dosage for the isolated hypoglycaemic compound(s).

Crude hexane, ethyl acetate, and methanol extracts (50 mg/kg BW) were administered intravenously to normoglycaemic Sprague-Dawley rats. The Oral Glucose Tolerance Test (OGTT) was then carried out using the Accu-Check Advantage II glucose kit to examine their effect on blood glucose concentration. Chromatography was then used to purify the active crude hexane extract, and the most hypoglycaemic fractions, yielded compounds FR2DBW (15 and 30 mg/kg BW) and FR1DBY (30 and 50 mg/kg BW) whose structures were elucidated by spectroscopic analysis.

The glucose tolerance curve for the crude hexane extract showed a significant lowering of the blood glucose concentration at the 90 minutes interval (4.71±0.19 mmol/L vs 6.1±0.68 mmol/L dimethyl sulfoxide, DMSO). Compounds FR1DBY, and FR2DBW were isolated from Fractions 1 and 2 respectively after purification by column chromatography (p<0.05). FR1DBY (30 mg/kg BW) was able to reduce the glycaemic peak at the 90 minutes interval (5.4±0.163 mmol/L) when compared to the control (6.32±0.369; p=0.038). When administered at 50 mg/kg BW there was an increase in the area under the glucose tolerance curve. At 90 minutes (5.26±0.183 mmol/L) was significantly different from the control (6.32±0.369 mmol/L; p≥0.05. FR2DBW was dose fr2dbw (5.05±0.182 mmol/L) was able to reduce the level of glucose within the blood when compared with the control (6.32±0.369 mmol/L; p=0.01). However, at a dosage of 15 mg/kg BW (6.10±0.200 mmol/L) where p=0.002. FR2DBW was less potent and similar to that of the control (6.32±0.369 mmol/L; p=0.614).

The hypoglycaemic compounds, FR1DBY and FR2DBW, were dose dependent and were more effective at a dosage of 50 and 30 mg/kg BW respectively.

Example 4

The Isolation, Purification and Elucidation of the Hypoglycaemic Principle of *Eucalyptus camaldulensis* in Normoglycaemic Sprague-Dawley Rats In the medical world today, herbal medicine has formed the foundation for various treatments, even with diabetes. In this study, *Eucalyptus camaldulensis*, commonly called River Red Rum, is one of such species being investigated for the hypoglycaemic principle present within the leaves. The *eucalyptus* is a large, fast-growing evergreen from the Myrtaceae family having over 800 species.

Methodology:
Crude hexane, ethyl acetate, and methanol extracts (50 mg/kg BW) were administered intravenously to normoglycaemic Sprague-Dawley rats. The Oral Glucose Tolerance Test (OGTT) was then carried out using the Accu-Check Advantage II glucose kit to examine their effect on blood glucose concentration Chromatography was used to purify the active crude hexane extract, and the most hypoglycaemic fraction (30 mg/kg BW), yielded Compound FR2DBW whose structure was elucidated by spectroscopy analysis.

Results:
The glucose tolerance curve for the crude hexane and methanol extracts showed a significant lowering of the blood glucose concentration at the 90 minutes interval (4.71±0.19 mmol/L vs 6.1±0.68 mmol/L dimethyl sulfoxide, DMSO), and (4.47±0.23 mmol/L vs 4.78±0.58 mmol/L water) at the 30 minutes interval, respectively.

Conclusion:
Overall, these results indicate that the crude hexane and methanol extracts illustrate significant hypoglycaemic activity. The hypoglycaemic principles (FR2DBW and FR1DBY) that were isolated from the crude hexane extract of *Eucalyptus camaldulensis* are fatty acids.

Example 5

The Hypoglycaemic and Hypotensive Effects of Eicosane

Eicosane, also known as icosane or didecyl, is a wax-like odorless compound containing a hydrocarbon link of twenty carbons and forty-two hydrogen atoms ($C_{20}H_{42}$). It has a molecular weight of 282.55 g/mol and is soluble in alcohol. This alkane is commonly used as an emollient/moisturizer, as a masking agent, for skin conditioning and other cosmetic uses. Eicosane occurs naturally in some plants in minute quantities, such as, cabocla flower oil brazil at 0.30%, cassie absolute at 0.40%, borania absolute, ketaki flower oil india in trace amounts, and witch hazel leaf oil at 0.60%.

These isolated compounds can be placed on the armamentarium of hyperglycaemia and hypertension with continued research, and as such help to reduce the prevalence of these chronic diseases and potentially could combat some of the side effects associated with some of the current remedies; while significantly contributing to the use of herbal medicine as alternative treatments.

Isolation and Investigation of the Hypogluycaemic Properties of FR1DBE (Eicosane)

A small quantity of white, wax-like crystals was obtained from column chromatography of the non-polar fractions of *Eucalyptus camaldulensis*. These crystals were recrystallized from fraction DB1, and were identified to be eicosane, as described below. The hypoglycaemic activity of the eicosane crystals was determined using the Oral Glucose Tolerance Test (OGTT) (FIG. 1) and rat models. From the Glucose Tolerance Curve (GTC), this compound, fr1dbe, was shown to be able to significantly lower the blood glucose concentration when administered at 30 mg/kg BW as evident when compared with the control during the fasting region (p=0.022 at the 30 minutes interval) and also at the 60 minutes interval where fr1dbe resulted in a blood glucose concentration of 3.7±0.154 mmol/L and DMSO had 4.44±0.115 mmol/L; p=0.002). During the post prandial region, fr1dbe significantly lowered the blood glucose concentration compared with the control DMSO (4.71±1.43 vs 6.32±0.369 mmol/L respectively) after the glucose load was administered (90 minutes interval). The reduced area under the curve persisted throughout the post-prandial region to the end of the experiment, where p<0.05, for example at 150 minutes interval, p=0.0015. A comparison done with metformin (FIG. 1) showed also the effectiveness of fr1dbe as there was a similar reduction in the blood glucose concentration as metformin. During the fasting region of the GTC, FR1DBE was significantly lower than both the negative DMSO and positive metformin controls (p<0.05 for both controls). At the 90 minutes interval, the area under the curve was less when FR1DBE was administered and compared with the metformin control, which showed 4.71±1.43 vs 5.07±0.089 mmol/L respectively At 90 min., there was no significant difference between the two (p=0.058). This continued throughout the post-prandial curve as the probability was greater than 0.05 at all intervals, for example p=0.374 at the 120 minute interval which showed that fr1dbe and metformin caused a similar reduction in the amount of glucose present within the blood.

The Identification of FR1DBE as Eicosane

Elucidation of FR1DBE was then done using spectroscopy. In the UV spectrum there was absorption at 246-303 nm lambda max, which is within the region of absorption of a long chain hydrocarbon compound (see Table 6). The FT-IR spectrum showed functional groups at peaks within the 2962-2850 $cm^{-1}$ region (2961.92-2848.24 $cm^{-1}$) which is also similar to that of the methylene chain and below 1500 $cm^{-1}$ (1470.88 and 716.20 $cm^{-1}$) which is typical of C—H deformations. A comparison of the published IR for eicosane was similar to the IR obtained above, especially in the regions mentioned above (NIST—National Institute of Standards and Technology. 2011). The melting point (m.p.) of the isolated fridbe was measured as 40-42° C. This compares with the published m.p. of eicosane as 36.8° C.

The gas chromatography-mass spectroscopy of compound fr1dbe was most informative and confirmed the presence of only one compound, which comprised 99.62% of the sample. The NIST library determination of its Mass Spectrum, determined the identity of this single compound as being eicosane to the high probability of 99%.

Final confirmation that fr1dbe was eicosane was obtained by a direct match by GC of fr1dbe and an authentic standard of eicosane, in three different temperature programs.

TABLE 1

Gas Chromatogram-Mass Spectrogram of FR1DBE

| $T_R$/min | Compound[a] | % Area | ID[b] |
|---|---|---|---|
| 21.21 | Eicosane | 99.62 | GC-MS, Match with standard of eicosane |

[a]Elution order on HP capillary column.
[b]GC-MS identification by Gas Chromatography - Mass spectrometry, and a Matching with an Authentic Sample of Eicosane in Three Different temperature Programs.

Matching of FR1DBE with Eicosane Standard

A Varian CP-3800 ® gas chromatograph interfaced with a Flame Ionization Detector (FID) was used to compare the isolated fr1dbe and an authentic standard of eicosane obtained from the Sigma-Aldrich company. The gas chromatograph was equipped with a (WCOT) fused silica coated with CP WAX 52CB capillary column (length 60 m×inner diameters 0.25 mm; 0.25 nm film thickness). The analytical conditions used were as follows; carrier gas Nitrogen, flow rate 1 mL min-1, split 1:100, injector temperature 250° C.; FID temperature was maintained at 300° C. Column oven temperature programs for matching with authentic standard from Aldrich (lot #13912HX) are as follows:

1. Column oven temperature program of initial temperature of 80° C. held for 1 minute, then increased from 80° C. to 190° C. at a rate of 20° C. $min^{-1}$ and held for 10 minutes. Retention time of Sample: 3.05 min. Retention time of Icosane std: 3.04

2. Column oven temperature program of 40° C. held for 3 minute, then increased from 40° C. to 800 C at a rate of 10° C. min-1, and held for 1 minute, then 80° C. to 200° C. at 10° C. min-1 held for 2 minutes and finally 200° C. to 250° C. at a rate of 10° C. min-1 and held for 10 minutes. Retention time of Sample: 5.43 min. Retention time of Icosane std: 5.42

3. Column oven temperature program of 70° C. held for 1 minute, then 70° C. to 200° C. at a rate of 20° C. min-1 and held for 5 minute, and finally 200° C. to 250° C. at a rate of 20° C. min-1 held for 1 minute.

All other instrument conditions were the same as used in the analysis of the essential oils. Retention time of Sample: 3.11 min. Retention time of Icosane std: 3.10

Determination of Haemodynamic Parameters

A non-invasive method was used to measure the blood pressure and heart rate of the rats using the CODA machine from Kent Scientific Corporation. The rats were placed in a restraint (rat holder), to reduce agitation, and then placed on a warming pad of the machine (to reduce anxiety). The occlusion and volume pressure recording cuffs (O-cuff and VPR-cuff respectively) were placed onto the tail of the animal in that order respectively, in order to record the readings. The O-cuff terminates blood flow to the tail and then dilates slowly allowing for the physiological readings to be obtained from the returning blood flow, which is determined by the VPR sensor. The VPR-cuff is then used to measure the arterial pulsations as blood returns to the tail and it begins to swell. As the tail begins to swell the systolic blood pressure is measured, while the diastolic blood pressure is calculated when swelling stops.

The rats were trained within the restrain for three to four days prior to the measurements in order to reduce errors and an additional acclimatization period was done to allow the rats to relax prior to the basal blood pressure readings. After this the active principles or extracts were administered at 30 mg/kg BW for the compounds fr1dbe, fr2dbs and fr2dbw and at 50 mg/kg BW for FR1DBY. The systolic and diastolic pressures, mean arterial pressure and the heart rate per minute was measured and about 20-25 readings were recorded and timed for approximately 30 minute including an allowance for acclimatization. For additional information, see Feng, M. and DiPetrillo, K. (2009). Non-invasive blood pressure Measurement in Mice. Dipetrillo, K. (Ed.) Cardiovascular Genomics, Methods and Protocols in Molecular Biology 573, (pp. 45-45). Humana Press, which is herein incorporated by reference in its entirety.

Hormonal Analysis.

This was carried out using the Mercodia ELISA Diagnostic kit in order to deduce the plasma insulin and glucagon levels respectively. These levels were used to determine the effect of the compound fr1dbe, on glucose homeostasis, when compared with a positive methformin and a DMSO negative control.

Serum Samples.

The samples were administered intravenously and orally at their respective dosages. After 15 minutes 75 mg/kg BW of sodium pentabarbitol was administered to the rats via an intraperitoneal injection. Blood samples were then obtained from the renal artery of the rats and collected in the (red)

vacutainer for the serum sample. The samples were then centrifuged at 3,000 r.p.m. for 10 minutes and stored at −20° C. until used.

Insulin Analysis.

The Mercodia ELISA is a direct technique utilizing two monoclonal antibodies of the insulin molecule, one of which binds to the microtitre well, while the other binds to the insulin within the sample. When the unbound antibody is removed, a reaction with 3,3',5,5'-tetramethylbenzidine aids in detection and spectophotometric analysis after the reaction is stopped.

Procedure.

The enzyme conjugate solution and wash buffer solution were prepared prior to the experiment. 10 μL of the calibrators, samples and controls were pipetted into the microtitre wells in duplicate. 100 μL of enzyme conjugate solution was pipetted into each well and allowed to incubate on a plate shaker (700-900 rpm) for 2 hours at room temperature (18-25° C.); after which the wells were washed six times with 350 μL wash buffer solution each. The ELISA plate was then inverted over the sink and tapped dry using absorbent paper. The substrate (TMB 200 μL) was then added into each well and left to incubate for 15 minutes at room temperature (18-25° C.). The reaction was then stopped with 50 μL of the stop solution to each well and adequately mixed on a plate shaker for about 5 seconds. The ELISA plate was read immediately at an optical density at 450 nm and the results calculated.

Glycosylated Haemoglobin ($HbAl_c$) Analysis.

This was done using the BioRad D-10 glycosylated HbAlc machine which utilizes the Helena Glyco-Tek Affinity Column Principle. This automated method separates the glycosylated and the non-glycosylated haemoglobins as the dihydroxyboryl group that is attached to the cellulose resin binds to the glucose molecule via the cis-diol group. The unwanted haemoglobins are removed while the glycosylated haemoglobins are eluted using a sorbitol buffer and recorded. Therefore, the sample was placed in the minute column and the $HbAl_c$ levels were determined as the amount of glucose found on the red blood cells are determined and recorded as the percentage $HbAl_c$ present.

Dosage.

The dosage of the extracted fr1dbe (30 mg/kg BW) and the glucose loads (1.75 g/kg BW were administered to the rats intravenously and orally, respectively. The extract was administered intravenously in order to reduce the amounts of sample that were used for the bioassays. The volume of the negative control/carrier agent (DMSO) used was approximately 0.3 mL.

GC-MS Analyses

The chemical compositions of the non-polar extracts were also determined using GC-MS. The instrument used was Hewlett Packard (HP) 6890 system Gas Chromatograph interfaced with a HP-5973 Mass Spectrometer. The gas chromatograph was equipped with a DB-VRX fused silica column (length 20 m×internal diameters 0.18 mm, film thickness of 1 μm). Analytical condition employed were, carrier gas He, flow rate 1 $min^{-1}$, split less mode, injector temperature of 250° C., interface temperature was 280° C., oven temperature program was 40° C. $min^{-1}$ for 2 minutes, then increased to 210° C. at a rate of 10° C. $min^{-1}$ and held for 15 minutes. The mass spectra data were collected with ionization energy of 70 eV and a mass range of 50-500 M/Z. These GC-MS analyses are reported (see Tables 3 to 8). All analyses were done at least twice and average values used.

Identification of Components from GC-MS

The components of the extract of the non-polar compounds were matched with mass spectral data of the NIST 98 library. Peaks which had a peak quality match greater than 70% was assumed to be accurately matches with the suggested compound from the library. Peaks of substantial quantity but poor quality were identified either by matching GC analyses with authentic compounds run in several programmes There was only one compound detected in the purified non-polar extract containing FR1DBE. This was determined to be eicosane by the mass spectral pattern of the NIST library. The identity of FR1DBE was definitively confirmed as eicosane by a direct match against an authentic sample of eicosane in three different temperature programs, using the Varian CP-3800 instrument.

The Effect of FR1DBE on Haemodynamic Parameters

Figure 2:
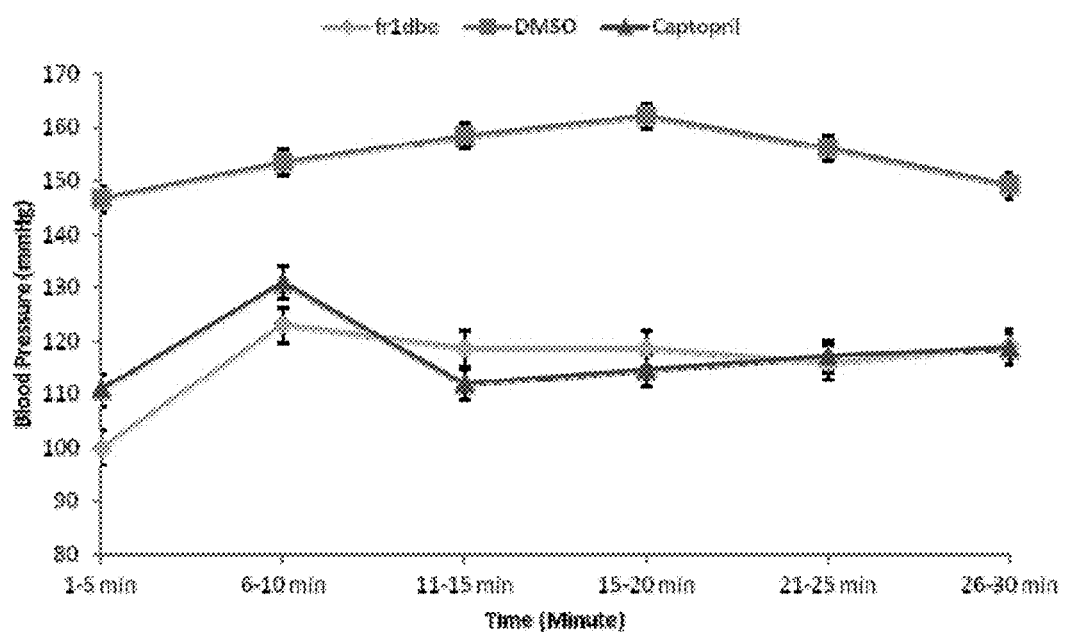
FIG. 2. SBP of FR1DBE (30 mg/kg BW) vs captopril (30 mg/kg BW) and DMSO.
Figure 3:
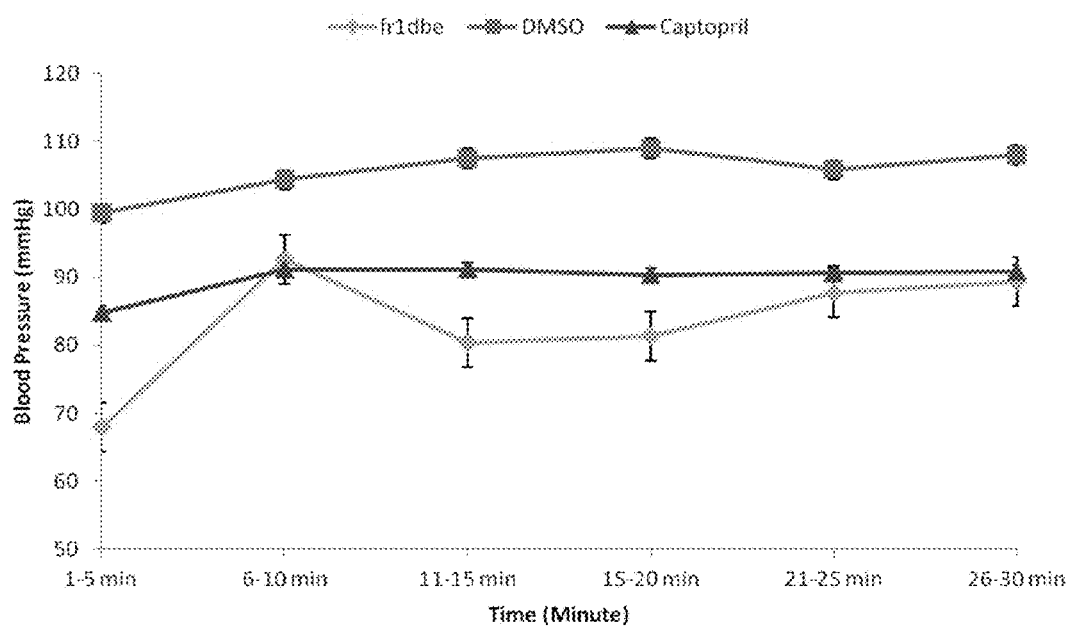
FIG. 3. DBP of FR1DBE (30 mg/kg BW) vs captopril (30 mg/kg BW) and DMSO.
Figure 4:
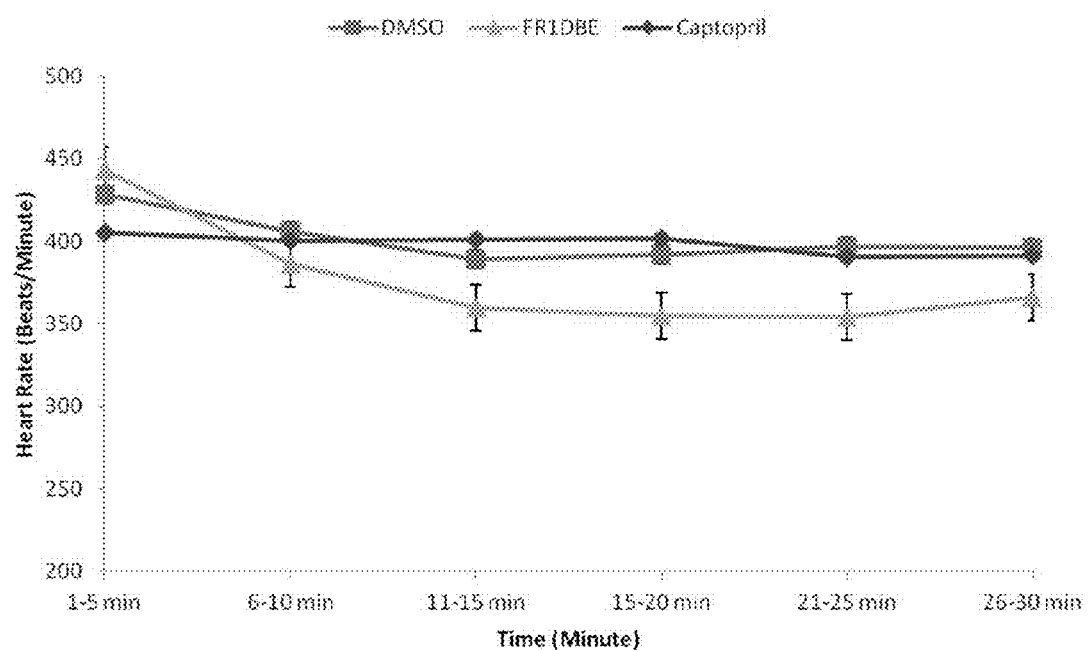
FIG. 4. Heart rate of FR1DBE (30 mg/kg BW) vs captopril (30 mg/kg BW) and DMSO.

The compound FR1DBE (eicosane) significantly reduced the systolic blood pressure (SBP) when compared with the control ($p<0.05$) as seen in (FIG. 2). It was able to cause an effect similar to that of captopril overall, however there was a little variation at the 10 minutes interval where FR1DBE was 118.42±1.87 mmHg and captopril was 131.35±1.50 mmHg ($p=1.54×10^{-05}$). However, at the 15 minute interval, fr1dbe was 122.21±1.1 mmHg and captopril was 119.81±2.61 mmHg showing significant difference ($p=0.40$). FIG. 3 also showed FR1DBE and captopril with a similar effect in reducing the diastolic blood pressure (DBP). However, at the 15 minute interval fr1dbe was significantly lower than captopril as seen in their values 84.0±0.98 mmHg and 91.19±1.37 mmHg respectively ($p=0.0001$) and also at the 20 minutes interval ($p=0.001$). Therefore, FR1DBE effectively reduced the diastolic rate, as compared with captopril, and by being significantly lower than the negative control with 'p' significantly less than 0.05 throughout.

Figure 5:
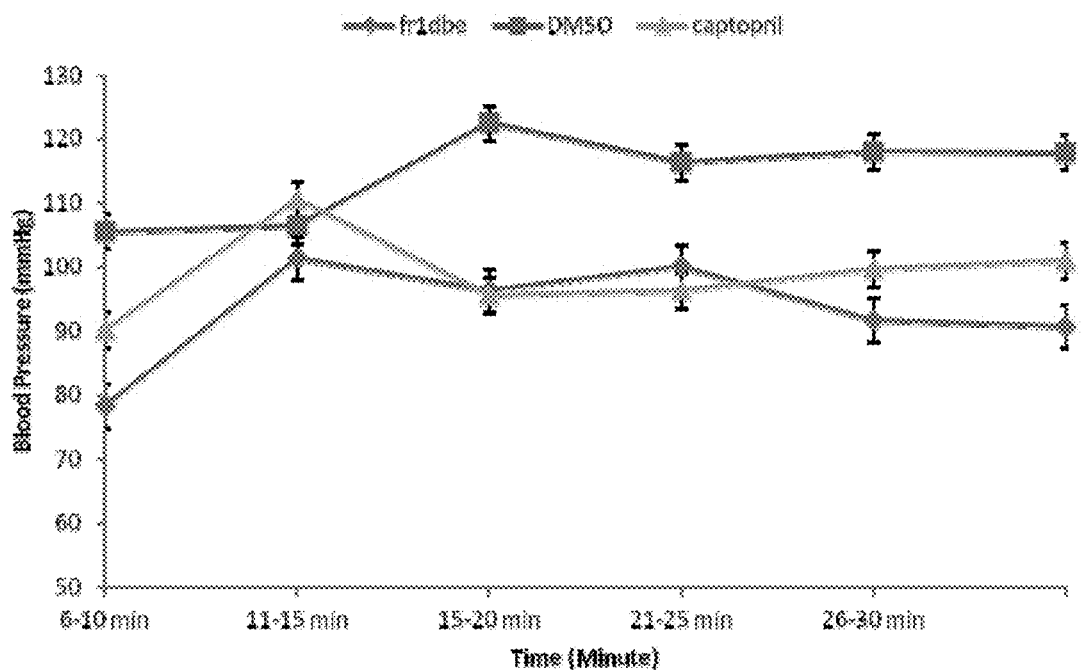
FIG. 5. MAP of FR1DBE (30 mg/kg BW) vs captopril (30 mg/kg BW) and DMSO.

FR1DBE (386.33±7.91 mmHg) did not significantly lower the heart rate at the 10 minutes interval when compared with DMSO (405.70±8.95; $p=0.30$) and captopril (412.52±6.91 mmHg; $p=0.09$). The lowering effect of fr1dbe was more apparent through the next 20 minutes. The mean arterial blood pressure was significantly reduced by the administration of fr1dbe (FIG. 5) when compared with DMSO, even at the 10 minutes interval ($p=0.03$). When compared with captopril, both captopril and fr1dbe were effective in obtaining a lower mean blood pressure. At the 15 minutes interval, fr1dbe and captopril, $p=0.002$, exhibited similar effects in reducing mean arterial pressure. As a result, fr1dbe can have a mechanism of action similar to that of captopril but also has some effect on the heart rate that causes a reduction in the number of beats per minute thus resulting in a lower blood pressure.

The Effect of Fr1dbe on the Post-Prandial Blood Insulin Level.

Figure 6:
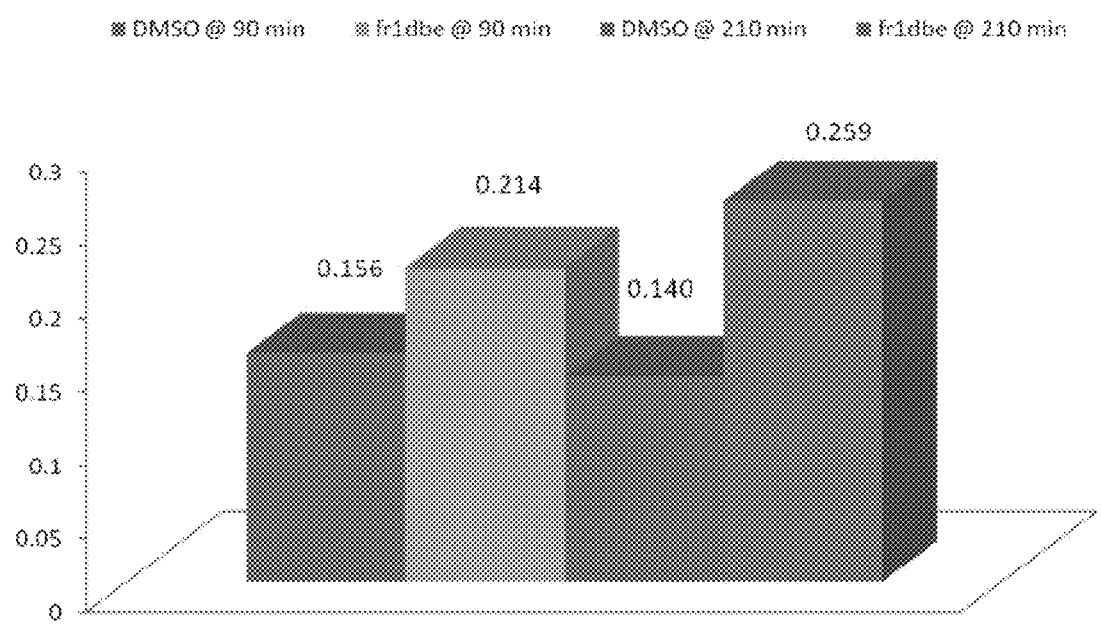
FIG. 6. The effect of FR1DBE (30 mg/kg BW) on blood insulin levels at the 90 and 210 minute intervals, respectively.

Fr1dbe was not soluble in water and as such was administered in DMSO intravenously. The fr1dbe sample (FIG. 6) was also able to significantly reduce the blood glucose concentration and as such resulted in an increase in the blood insulin concentration. After the 90 minute interval the insulin levels had significantly increased from 0.156±0.01 ug/L to 0.214±0.02 ug/L for the DMSO control and the isolated fr1dbe, respectively where $p=0.007$. Therefore, this hypoglycaemic isolate was able to initiate insulin release more rapidly, at the 90 minute interval. Its effect was greater than the two other isolated fractions, fr2dbw and fr1dby, in response to the glucose load that was given after an hour. This reduction in the blood glucose concentration was even significantly higher after 3½ hours of administration, as the control had little insulin released (0.140±0.002 ug/L) when compared with fr1dbe (0.259±0.03) which produced a significantly different result ($p=0.005$).

Materials and Methods

Materials and Methods used in this section were generally the same as those described above in examples on the determinations for oleic and palmitic acids.

The blood pressure and heart rate of the rats were done using the CODA machine from Kent Scientific Corporation.

The hormonal analysis was carried out using the Mercodia ELISA Diagnostic kits in order to deduce the plasma insulin and glucagon levels respectively.

Conclusion

From further examination of the non-polar extract of *Eucalyptus camaldulensis*, it was shown that there was another compound apart from oleic and palmitic acids that was also hypoglycaemic. This additional hypoglycaemic compound was positively identified as eicosane.

From this investigation, it was determined that eicosane, isolated from *Eucalyptus camaldulensis* (Myrtaceae), also reduced blood glucose levels, and this property was confirmed in experiments with both a negative and a positive control, DMSO and Metformin, respectively. These experiments were done with rat models.

It was also confirmed, in rat models also, that blood pressure levels are also reduced by the application of eicosane. This property of eicosane was also confirmed by comparative experiments using a negative and positive controls, DMSO and Captopril, respectively.

In the experiments using the rat models, eicosane was shown to at least as effective as Metformin and Captopril.

Example 6

Over 400 traditional plant treatments for Diabetes mellitus have been recorded, with only a small number receiving scientific and medicinal validation. These are predominantly used in under-developed regions, thus, research into alternative treatment for diabetes may provide valuable clues for the development of new oral hypoglycaemic agents. As a result, this investigation seeks to validate the ethnobotanical uses of *Eucalyptus camaldulensis* associated with the treatment of diabetes. The leaves and stems of this plant were obtained from Hope Bay, Portland where it is commonly used in Jamaica as a "sugar lowering" tea. The plant materials were dried, milled and solvent extractions were carried out in order to isolate the compounds that were soluble in hexane, ethyl acetate and methanol, and these were referred to as the crude hexane, ethyl acetate and methanol extracts respectively. The bioactivity of these extracts was then tested using normglycaemic Sprague-Dawley rats, in order to determine the effect on the blood glucose concentration using the Oral Glucose Tolerance Test (OGTT).

The extracts were administered both orally and intravenously to the rats with the crude hexane extract being the most hypoglycaemic and because of this; the active component in this extract (FR1DBY, FR1DBE, FR2DBS and FR2DBW) were isolated after a series of purification procedures. The structures of the active compounds were elucidated and found to be known compounds that were commercially available; however, their direct hypoglycaemic activity and various dosage abilities were unknown, especially with the combined effect of FR2DBW (synergistic effect observed from two of the compounds that were isolated). These compounds can be marketed as new oral hypoglycaemic agents that would aid in the reduction of elevated blood sugar levels that are seen in diabetics, especially after a meal is ingested. These compounds have been consumed over centuries and as such would reduce or eliminate the toxicity tests that would be required, for new pharmaceuticals/nutraceuticals.

An agent that can significantly reduce the post-prandial blood glucose concentration would be a major breakthrough to the control of the disease and will undoubtedly add to the wealth of knowledge of folkloric plants and increase the number of the said by scientific research. Although there are various oral agents being used for the treatment of hyperglycaemia, one that can be incorporated in the preparation of meals as functional foods for diabetic patients would not only be convenient but also dramatically reduce the incidence of high blood sugar as FR2DBS and FR2DBW can stimulate the release of insulin from the beta-cells of the pancreas and in effect lower the blood glucose concentration. The addition of these edible compounds in the preparation of cooking oils, margarines, salad dressings and mayonnaise would significantly lower the blood glucose level while also protecting the cardiovascular system as they are known to promote the lowering of cholesterol level.

Diabetes and hypertension are considered the chronic duo in society; complications of Diabetes mellitus often lead to elevated blood sugar concentration and other cardiovascular diseases, kidney problems, among others. These compounds were also tested for their hypotensive activity using a Coda-6-Non-Invasive machine and were shown to aid in the reduction of the blood pressure. Capsules of these hypoglycaemic compound as dietary supplements would be advantageous especially to the control of hyperglyceamia and T2DM by extension and would also give a dual effect in reducing the blood pressure. The purified crude hexane extract can also be made into convenient nutraceutical capsules or powder/granules which can be conveniently taken throughout the course of the day. This would indeed assist in the overall managing of the blood sugar level where at the first sign of dizziness or upon checking the blood glucose concentration these remedies can provide quick, effective and efficient relief.

Further studies were done to deduce the efficacy of the active compounds isolated from *E. camaldulensis*. These compounds were shown to be comparable to metformin, which is a common oral hypoglycaemic agent being used in the treatment of T2DM, in eliciting their effect. A comparison was also done with a known hypertensive drug (Captopril), to determine the effect of these isolated compounds on hypertension. These compounds were able to significantly reduce the blood pressure similarly to the effect obtained when captopril was administered at the same dosage, and as such, increase the effectiveness of these oral agents in the treatment of hyperglycaemia and hypertension.

There is a need for affordable, quick and effective control of hyperglycaemia and hypertension, which would prevent an onset or worsening of T2DM and reduce person having elevated blood pressure levels within society, and eventually a reduction in society. These compounds are organic and would be easily broken down in the system and utilized. Further studies that will be conducted will be to determine the effectiveness in streptozotocin-induced diabetic rats; and also to deduce if there are any interactions that can occur with other medications that a patient or person are likely to be taking. This would be carried out by deducing the interaction with the P450 enzymes within the liver, which are responsible for the breakdown and release of compounds within the body.

Various conventional treatments have been established for a plethora of diseases with the use of herbal medicines, such as Diabetes mellitus and Hypertension. Diabetes mellitus is a chronic disease which affects about 150,000 Jamaicans within the age group 15-74 and has become one of the leading causes of death directly or indirectly. While, among the most threatening chronic diseases today are renal, cardiac and cerebrovascular diseases, the effects of which are significantly increased as a result of elevated blood pressure. In this study, *Eucalyptus camaldulensis*, commonly called River Red Rum, was investigated for the hypoglycaemic principle present within the leaves and stems and subsequently, their hypotensive activity. The *eucalyptus* is a large, fast-growing evergreen from the Myrtaceae family which has been used by folklore medicine for anti-diabetic effects.

In the Caribbean, and specifically Jamaica, plants are used as food, but also they are the first source of treatment, especially amongst the elderly and those residing in the rural areas. Thus to authenticate their ethnobotanical and medicinal uses scientifically will provide the much needed information to substantiate their uses and to produce various oral therapies without the high toxicity levels and other possible side effects. Therefore, preventing or treating hyperglycaemia would be a major step in the overall control of type 2 Diabetes mellitus (T2DM) and by extension a hypotensive effect in the blood pressure as both diseases are often considered the chronic duo. In 2008, approximately 40% of the world adult population above the age of 25 had a blood pressure that was above normal with a population of approximately one billion experiencing uncontrolled hypertension (Global Health Organization (GHO-WHO, 2012). In Jamaica, hypertension affects 30.8% of Jamaicans at or over the age of 15 years old, with an estimated prevalence of 39.9% in the upper middle income group alone in 2008, as reported by the WHO in 2011. As a result, new and improved measures have to be taken in order to combat this growing trend of elevated blood pressure levels.

The active crude leaves and stems extract of the *E. camaldulensis* corroborated the use of the plant as an anti-diabetic agent. This was investigated using a series of Oral Glucose Tolerance Tests and a comparative study with the commercially available compounds (after elucidation of the structures) and a known oral hypoglycaemic drug, metformin. The Coda-6-Non-Invasive machine was used to determine the effect of the isolated compounds on the blood pressure and a comparison was also done with a commonly used hypertension drug (Captopril), in order to increase the efficacy of the findings and thus produce scientific credence for the use of the plant.

This type of research is imperative as Diabetes has become a global epidemic to over 170 million people worldwide in 2000; with 800,000 new cases diagnosed every year. It has become the sixth leading cause of death in America, having over 18 million affected, which is almost 7% of the total population and is the major cause of disability from the disease. Thirteen million are currently being treated; however, five million are yet to be diagnosed. Within the Caribbean, it is the leading cause of secondary blindness, and in Jamaica, it is one of the leading causes of death and about 150,000 Jamaicans within the age group 15-74 have diabetes mellitus (World Health Organization, 2006). The WHO estimates that by 2025, 300 million people could be diagnosed with diabetes worldwide. Currently, 5% of the world's population is diabetics, and in many countries, diabetes mellitus has consumed 10% of the total health care expenditure.

Once diagnosed with diabetes, especially T2DM, with immediate effect lifestyle changes have to take place in order to control hyperglycaemia. The ADA and the European Association for the Study of Diabetes in September 2006 recommended that those recently diagnosed diabetics, must also be treated with metformin, an oral hypoglycaemic drug, along with lifestyle modifications in order to combat the deleterious effects of diabetes, regardless of their body weight, disregarding the previous recommendations that oral hypoglycaemic drugs be used as a second option when lifestyle changes are not apparent in glycaemic control. Oral hypoglycaemic agents are referred to as those orally administered drugs that lower the blood glucose concentration in order to treat Diabetes mellitus. However, there are many other anti-diabetic drugs that are currently being used in conventional therapy; such as Exenatide™ and Pramlintide™ which were approved in 2005 for the treatment of diabetes. In South Africa, *Hypoxis hemerocallidea*, also called the "African Potato" is known to be a good remedy to control or treat diabetes, where about 80% of the rural communities were still employing their natural vegetative resources for treatment. In developing countries, such as Jamaica, medicinal plants have been and are still being used as the remedy from the smallest ailments to complications as large as diabetes and hypertension. Some of these plants are already being packaged as dietary adjuncts, while for others the active compounds have been isolated successfully, and may pave the way for the development of new anti-diabetic drugs and phytotherapy.

Various scientific methods have been used to corroborate the hypoglycaemic activity present within the tested plants as stipulated or demonstrated by ethnomedicinal practices in treating and controlling Diabetes mellitus, and others for hypertension. This research aims to do the same by purifying and isolating the bioactive principle(s) in this *eucalyptus* species and as such will increase the overall control of those diagnosed, and by extension to reduce the prevalence of T2DM and hypertension in Jamaica and even globally.

Example 7

Three compounds from a local plant were discovered, and their effectiveness against two of the "Lifestyle Diseases" of hyperglycaemia, high blood sugar level, and hypertension, high blood pressure, was confirmed.

In investigating a local ethnomedical claim for the blood sugar lowering properties of the leaves of *Eucalyptus camaldulensis* (Myrtaceae) from the Hope Bay, Portland area, inter alia, three compounds, two of which are commonly consumed fatty acids and the third, a hydrocarbon, were identified. Remarkably, it was found that all three compounds, not only reduced blood sugar levels and that their effectiveness were as good as the well known medication used to treat Diabetes mellitus, Metformin, but in addition, they were also as good in reducing blood pressure levels as Captopril, one of the widely used treatments against high blood pressure. The results were also confirmed in comparisons with negative controls of the solvents only.

It was also found that the two well known fatty acids exhibit a synergistic effect, that the effect of a combination of the two of them had a greater effect than either used singly. This was true for both their blood sugar lowering and their blood pressure lowering properties. For the blood sugar lowering property, a series of experiments were conducted of a range of mixtures and obtained the ideal synergistic mixture for optimal hypoglycaemic effect.

The experiments were carried out on rat model experiments using Sprague-Dawley rats, and the results were subjected statistical analyses in order to confirm these conclusions. For human usage and confirmation of effectiveness in humans, clinical trials would have to be done, but it is a common drug development pathway to start with pre-clinical trials with rat models and if successful, to proceed to clinical trials on humans.

The chemical identity of the isolated plants constituents were confirmed by spectroscopy, primarily NMR. and gas chromatography (G.C.). Experiments using the purchased identified compounds gave similar results to the extracted ones in the experiments described herein, and G.C. comparisons between a standard of the hydrocarbon and that of the extracted constituent in three different temperature programs, confirmed their identity.

The extracted constituents were administered both intravenously and orally with the same positive results. In the case of the two fatty acids, their oral application with reduction of blood sugar and high blood pressure levels is extremely attractive. Firstly, being well used foods, the need for extensive toxicity studies would not be necessary. In a separate experiment, the fatty acids were administered as a mixture of the oils which contain them as their most important component, and which are widely used as foods. The confirmation that the beneficial effects can be obtained from a mixture of the oils, is commercially beneficial, and the fact that the beneficial effects are also obtained from an oral administration, will allow for the commercial use in functional foods such as dressings, mixed oils, and directly as supplements such as soft capsules.

No reports of toxicity for the hydrocarbon which also exhibit hypoglycaemic and hypotensive properties, were found, and its usage for humans can require toxicity and similar evaluations in humans.

The tree from which these active ingredients were extracted, Eucalyptus camaldulensis (Myrtaceae) has been reported to have been introduced into the island in the early twentieth century, to assist in watershed management and as a known source of both lumber and firewood. It has since become established in the flora of the island and can be found in many locations across the island. It has many reported medicinal and ethno-medical uses in its native Australia but also in the many countries in which it has been introduced.

The hypoglycaemic property of palmitic acid has not been reported, and the synergistic behavior of oleic acid and palmitic acid has not been previously reported. Similarly, the hypoglycaemic and hypotensive properties of the hydrocarbon eicosane has not been reported.

With the advances in medicine, the contagious diseases of the past have become less important in the health of modern society and of increasing importance are the so called "Lifestyle diseases", such as obesity, the cardio-vascular diseases, diabetes, hypertension, some cancers, etc. These are argued to be the result of modern society: diet, lack of exercise, chemical contaminants of modern industry.

Diabetes, for example, has become a global epidemic affecting over 170 million persons in 2000, with an estimated 800,000 new cases diagnosed every year. It has become the sixth leading cause of death in the USA, with over 18 millions or almost 7% of the population affected.

In the Caribbean, it has been determined as the leading cause of secondary blindness, and in Jamaica, it is one of the leading causes of death with an estimated 150,000 Jamaicans within the age group 15-74 developing the disease.

The effects of high blood pressure are also very damaging and similar to high blood sugar levels can be undetected for years, becoming a silent killer. Hypertension has an adverse affect on many of the organs of the body. It will increase the incidences of cardio-vascular diseases, increasingly damage eyesight and result in glaucoma, and adversely affect the heart and kidneys as some examples.

It is an extremely useful to find previously undocumented or unknown health benefits for well used foods, especially when the potential benefits are the combating of two of the very important lifestyle diseases of modern society. The investigations into different modes of administration, of the ideal synergistic mixture, and with the parent oils themselves, all afford a variety of applications as functional foods, nutraceuticals, dietary supplements, inter alia.

It was found that two fatty acids, oleic acid and palmitic acid, are among the hypoglycaemic and hypotensively active compounds of Eucalyptus camaldulensis. The finding that palmitic acid has both hypoglycaemic and hypotensive properties has not been reported. In addition, it was found that there is a synergistic effect in the use of palmitic acid and oleic acid, and the optimal mixture of both has been determined.

Example 8

Purification of Hypoglycaemic Components

The techniques used to purify the crude hexane extract included: Thin Layer Chromatography (TLC) and Flash Column Chromatography (FCC). The semi-purified fractions obtained from the FCC were screened for their hypoglycaemic activity using the OGTT (Oral Glucose Tolerance Tests) after being grouped into five main groups according to their TLC profile. Further purification was carried out using recrystallization to obtain the precipitate from the semi-purified sub-fractions and bio-assayed until the active compound(s) were identified.

Thin Layer Chromatography

This method was carried out in order to separate the compounds that were present in the crude extract or fraction using the Sigma-Aldrich plastic backed TLC plates with plate size of 20×20 cm; 250 µm thickness. The solvent chamber was set up with the solvent system to be used, for example 85% hexane: 14% ethyl acetate: 1% methanol; it was then left for approximately 5 minutes in order to saturate the chamber. The solvent was allowed to move up the filter paper that was used to protect any light sensitive compounds that may have been present. The sample was prepared in an eppendorf tube where a small amount of the crude hexane extract was dissolved in about 1000 µL of hexane. A spot of the crude hexane extract (sample) was placed at approximately 1 cm from the base, which was just above the solvent (mobile phase) when placed in the chamber, it was allowed to air dry before being placed in the developing chamber.

The TLC plate was removed from the chamber when the solvent front was about 1 cm from the top. The separated compounds were then visualized using the ultraviolet radiation at 254 and 366 nm which was the short and long wavelengths respectively. For long term use, the plates were sprayed with ammonium molybdate-sulfuric acid reagent and heated in order to identify most organic compounds that would produce a blue or green spot afterwards. The most suitable solvent system was then used to purify the crude hexane extract using flash column chromatography Column Chromatography
1. The apparatus was set up by measuring about 287.7 g of Sigma silica (200-425 mesh; Cas 112926008) which was packed in the glass column using hexane.
2. A layer of sand was then placed on the top of the silica bed to ensure that it was stable. Approximately 14.5 g of the crude hexane extract was then applied on top of the sand using a Pasteur pipette.
3. Hexane (500 mL) was then added to the column to initiate separation and the eluent was collected in 125 mL conical flasks in volumes of 100 mL each.
4. When no further movement was observed within the column, TLC was carried out to confirm that the most non-polar compounds were already eluted. Ethyl acetate was then added to increase the polarity of the solvent system.

5. Varying solvent systems were used of hexane:ethyl acetate (90%: 10% respectively; 1.5 L). Fractionation was obtained as the solvent was added with increasing polarity (hexane:ethyl acetate) until all the non-polar compounds were eluted; after which methanol was used to remove the most polar compounds and in effect to wash the column (Table 6).

Forty-four (44) sub-fractions were obtained and subsequently grouped according to their TLC profiles into five (5) main fractions: fraction 1 was a bright yellow and wax-like solid (DB1; 2.98 g), fraction 2 was light yellow and also a wax-like solid (DB2; 1.23 g), fraction 3 was an army green solid (DB3; 3.04 g), fraction 4 (DB4; 1.89 g) and fraction 5 (DB5; 3.92 g) were dark green and viscous (gummy-like). These 5 groups were then bioassayed using the OGTT in order to identify the active fraction.

Recrystallization

Recrystallization was carried out to isolate the precipitate that was observed in fractions DB1, DB2 and in minute quantities of DB3. About 500 mg of the sample was sparingly dissolved in a small amount of methanol with about 2 drops of hexane and 1 drop of ethyl acetate. The purified precipitate from the fractions was then isolated and dried using vacuum filtration. Fraction DB1 yielded white crystals referred to as FR1DBY with a retention factor ($R_f$) of 0.24 cm (100.31 mg was obtained), the remaining solution was then heated with hexane and drops of methanol and allowed to cool.

Another compound, white and wax-like crystals, were isolated via recrystallization to yield FR1DBE. A clear, waxy oily-like compound was also isolated from fraction DB1 and referred to as FR1DB(1-3); this was the first compound that was eluted from the FCC column. It was further dried under the vacuum and tested for its bio-activity via OGTT. From fractions DB2 and DB3 that was recrystallized, off-white crystalline compounds were obtained. TLC profile showed that it was the same compound with a retention factor ($R_f$) of 0.19 cm; this compound was cumulated and referred to as FR2DBW (397.3 mg was obtained). The solution in the flask referred to as the mother solution, a yellow oily compound referred to as FR2DBS was then dried and a TLC profile done to ensure that the precipitated compound was removed. All the isolated compounds were then tested for bioactivity using the OGTT and subsequently, for its hypotensive properties.

Elucidation of the Active Component/s

In order to elucidate the structures of the isolated compounds that showed significant hypoglycaemic activity a series of spectroscopic techniques were employed. Identification of the active components was done using nuclear magnetic resonance ($^{13}$C-NMR and $^1$H-NMRProton (H) and Carbon (C) Nuclear Magnetic Resonance (NMR) in order to identify the basic structures of the compounds by the number of carbon and hydrogen atoms that were present in the compound. NMR also elucidated the number of double or triple bonds that were present if at all, the types of groups that may be present based on the chemical shifts and coupling of the carbon and hydrogen atoms.

The Bruker Vector 22 Instrument, wavelength 633 nm was used to deduce the functional groups by Fourier-Transform infra-red spectroscopy and Hewlett-Packard ultraviolet machine and Bruker gas chromatography-mass spectroscopy was used to identify the molecular aspects of the compounds and subsequently identify the structure using the NIST library determination of the mass spectrum of the compounds.

Elucidation of FR1DBE was also done using gas chromatography as a final confirmation of its structure using a direct match by GC with an authentic standard of eicosane, in three different temperature programs.

A Varian CP-3800® gas chromatograph interfaced with a Flame Ionization Detector (FID) was used to carry out the comparison with an authentic standard of eicosane obtained from the Sigma-Aldrich company. The gas chromatograph was equipped with a (WCOT) fused silica coated with CP WAX 52CB capillary column (length 60 m×inner diameters 0.25 mm; 0.25 μm film thickness). The analytical conditions used were as follows; carrier gas Nitrogen, flow rate 1 mL min$^{-1}$, split 1:100, injector temperature 250° C.; FID temperature was maintained at 300° C. Column oven temperature programs for matching with authentic standard from Aldrich (lot no. 13912HX) are as follows:

Temperature 1: The column oven temperature program of initial temperature of 80° C. was held for 1 minute, then increased from 80 to 190° C. at a rate of 20° C. min$^{-1}$ and held for an additional 10 minutes. Temperature 2: The column oven temperature program of 40° C. held for 3 minute, then increased from 40 to 80° C. at a rate of 10° C. min$^{-1}$, and held for 1 minute, then from 80 to 200° C. at 10° C. min$^{-1}$ held for 2 minutes and finally 200 to 250° C. at a rate of 10° C. min$^{-1}$ and held for 10 minutes. Temperature 3: The column oven temperature program of 70° C. held for 1 minute, then 70 to 200° C. at a rate of 20° C. min$^{-1}$ and held for 5 minutes, and finally from 200 to 250° C. at a rate of 20° C. min$^{-1}$ held for 1 minute. All other instrument conditions were the same.

The compounds are identified as oleic and palmitic acids by spectroscopy. The active compounds are confirmed as oleic and palmitic acids by their GC-MS and also confirmed by the NIST library of fragmentation patterns.

OGTT of the Commercially Available Compounds.

After elucidation of the compounds isolated from *E. camaldulensis* as oleic acid and palmitic acid, the commercially available compounds were obtained from Sigma-Aldrich and used to carry out OGTTs (FIGS. 9-13). A comparison of the bought and isolated samples was then done at the same dosages of 700 and 900 mg/kg BW.

OGTT of the Comparison with Metformin.

Figure 14:
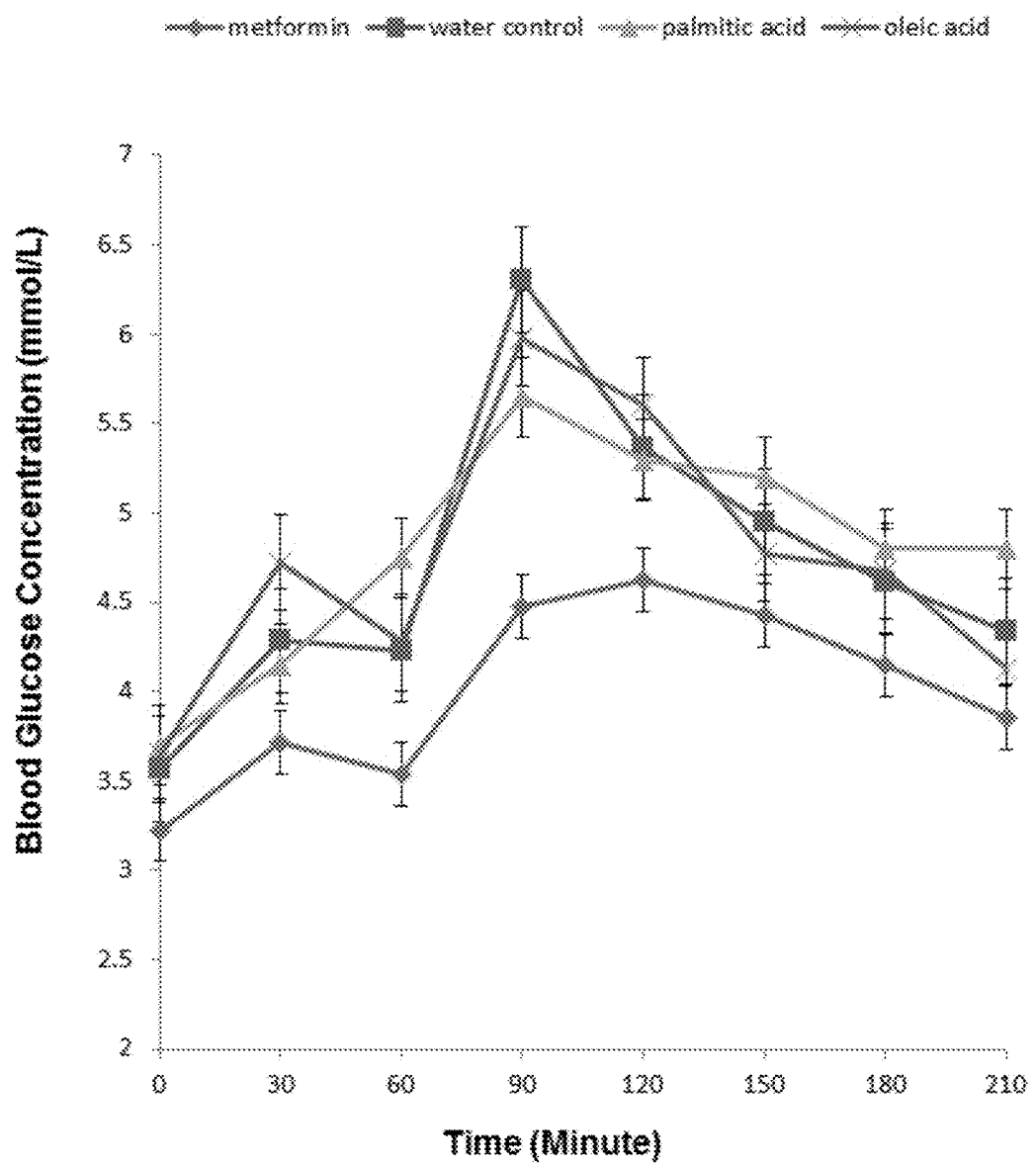
FIG. 14. GTC of oleic and palmitic acids at 200 mg/kg BW vs water and methformin (oral administration).
Figure 15:
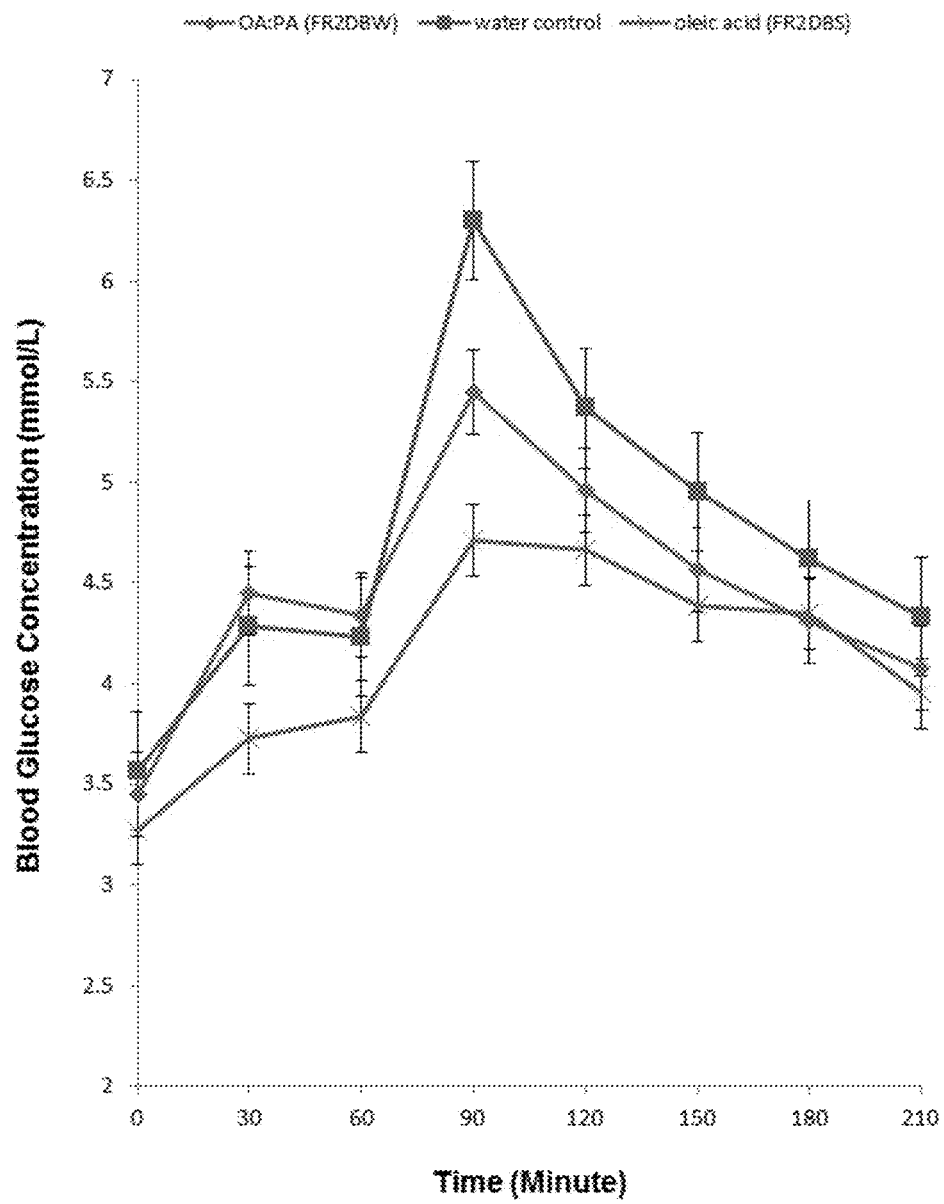
FIG. 15. GTC of OA:PA (oleic:palmitic acid) and oleic acid only at 700 mg/kg BW vs water (oral administration).
Figure 16:
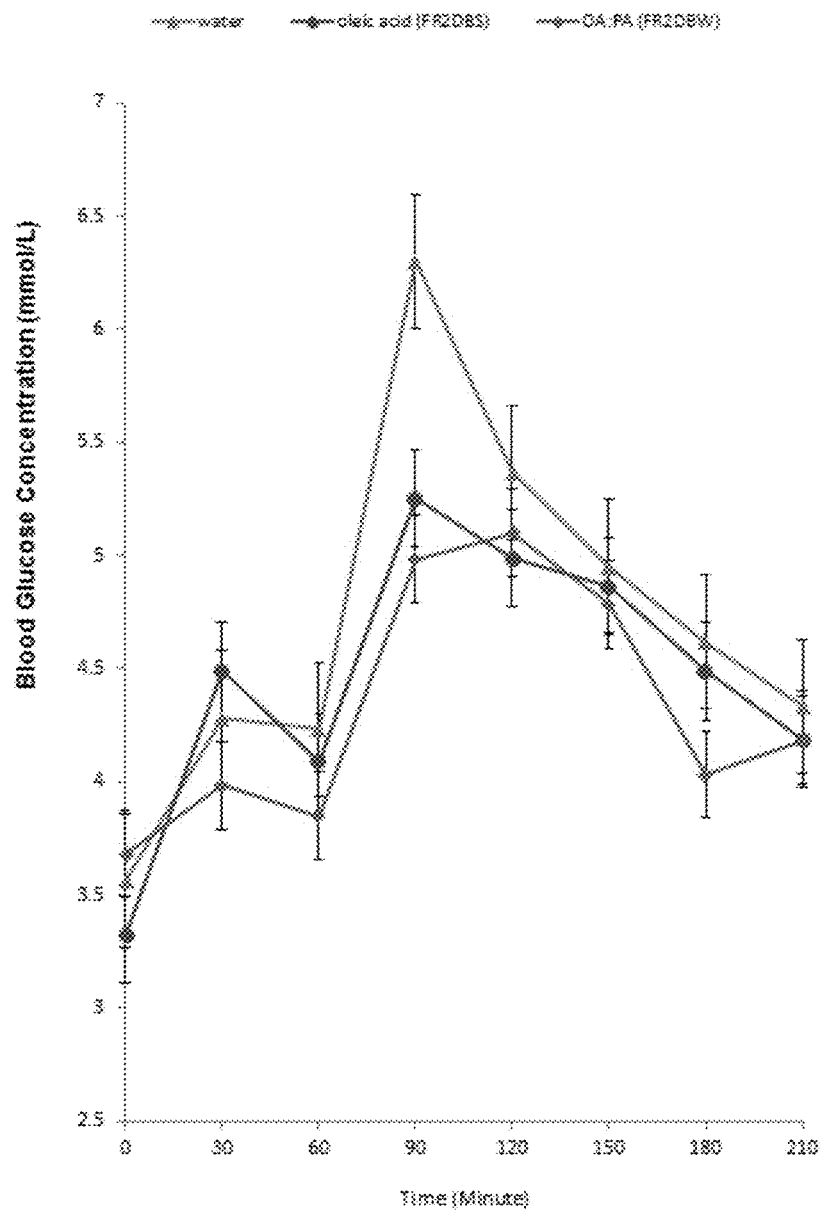
FIG. 16. GTC of oleic acid only (FR2DBS) and the OA:PA combined at 900 mg/kg BW vs oral water control.

In order to determine the efficacy of the isolated compounds, a known oral hypoglycaemic drug, metformin was used to do a comparison. Metformin was obtained from Sigma-Aldrich (Cat. No. d15, 095-9) and OGTTs were done via intravenous (FIGS. 7-13) and oral administration (FIGS. 14-16).

OGTT of Oleic Acid (OA):Palmitic Acid (PA) Ratios.

The synergistic effect of both fatty acids, palmitic and oleic acid was evident in FR2DBW. As a result different ratios (Table 2) were used to determine the best ratio that would be most effective in reducing the blood glucose concentration. These ratios were also compared with metformin, a known hypoglycaemic agent, vs DMSO control. Table 2 below shows the ratios used to carry out the OGTT, which is shown on the FIGS. 9-13.

TABLE 2

The synergistic effect of octadecanoic and hexadecanoic acids on the blood glucose concentration at different ratios.

| Sample | Octadecanoic (Oleic) Acid (%) | Hexadecanoic (Palmitic) Acid (%) |
|---|---|---|
| OA | 100 | 0 |
| OA:PA (3:1) | 70 | 30 |
| OA:PA (1:1) | 50 | 50 |
| OA:PA (1:3) | 30 | 70 |
| PA | 0 | 100 |

Dose-Dependent OGTT of the Hypoglycaemic Compounds Via Oral Administration.

The hypoglycaemic principles of E. camaldulensis were also administered orally. Preliminary OGTT experiments at 200 and 500 mg/kg BW were done, and as a result the dosage was increased to 700 and 900 mg/kg BW. The glucose tolerance curves (GTC) were obtained similarly to the OGTT done via intravenous administration, in that the compound was administered after the fasting blood sample was obtained, however via a oral gavage (FIGS. 14-16).

The Effect of the Hypoglycaemic Compounds on Haemodynamic Parameters (Blood Pressure and Heart Rate)

A non-invasive method was used to measure the blood pressure and heart rate of the rats using the CODA-6-non-invasive machine from Kent Scientific Corporation. The rats were placed in a restraint (rat holder), to reduce agitation, which was then placed on a warming pad of the machine (to reduce anxiety). The occlusion and volume pressure recording cuffs (O-cuff and VPR-cuff respectively) were placed on to the tail of the animal in that order respectively, in order to record the readings. The O-cuff terminates blood flow to the tail and then dilates slowly allowing for the physiological readings to be obtained from the returning blood flow which is determined by the VPR sensor. The VPR-cuff then measured the arterial pulsations as blood returns to the tail and begins to swell. As the tail begins to swell the systolic blood pressure is measured, while the diastolic blood pressure is calculated when swelling stops.

The rats were trained within the restrain for three to four days prior to experiment in order to reduce errors and an additional acclimatization period was done to allow the rat to relax prior to the blood pressure readings, after which the active principles or extract was administered at 30 mg/kg BW for the compounds: FR1DBE, FR2DBS, FR2DBW and captopril, and at 50 mg/Kg BW for FR1DBY. The systolic and diastolic blood pressure, mean arterial pressure and the heart rate per minute was measured and about 20-25 readings were recorded and timed for approximately 30 minutes including acclimatization (FIGS. 17-28). For additional information, see Feng, M. and DiPetrillo, K. (2009). Non-invasive blood pressure Measurement in Mice. Dipetrillo, K. (Ed.) Cardiovascular Genomics, Methods and Protocols in Molecular Biology 573, (pp. 45-45). Humana Press, which is herein incorporated by reference in its entirety.

Comparison of the Bioactive Compounds (Combined Fatty Acids (FR2DBW), Eicosane (FR1DBE), Oleic Acid (FR2DBS) and Palmitic Acid (FR1DBY) with Metformin.

Figure 7:
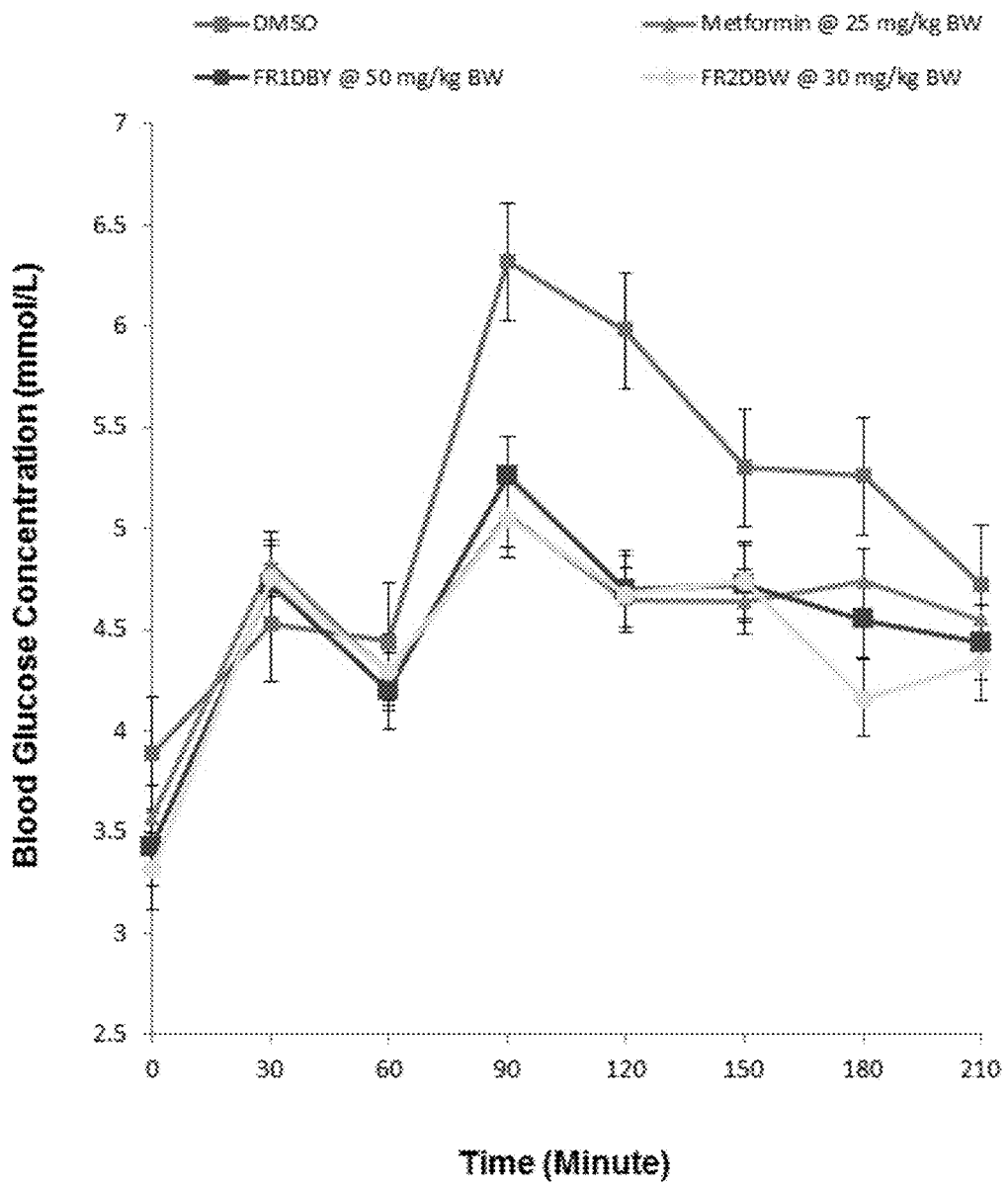
FIG. 7. GTC of FR1DBY and FR2DBW at the most effective dosages vs DMSO and metformin (IV administration).

An overall comparison between the compounds isolated from the crude hexane extract of *Eucalyptus camaldulensis* and metformin showed significant hypoglycaemic activity at their most ideal dosage of 30 mg/kg BW for FR2DBW, FR1DBE and FR2DBS and at 50 mg/kg BW for FR1DBY, via intravenous administration. Metformin was administered at 25 mg/kg BW also via intravenous administration. All isolated compounds were able to dramatically reduce the blood glucose concentration vs control (DMSO). FR2DBW was the most abundant compound isolated from the fractions of the crude hexane extract and when compared with metformin at 30 and 25 mg/kg BW respectively, the same level of reduction in the blood glucose concentration was observed throughout the experiment even at the 180 minute interval (p=0.069). Therefore, metformin and FR2DBW had a significant effect after the oral glucose gavage. This is important as it demonstrated the use of FR2DBW as a potential hypoglycaemic drug that was able to contain the amount of glucose found in the blood after a meal was ingested as it was capable of reducing the glycaemic peak by 1.27 mmol/L when compared with the control (5.05±0.182 vs 6.32±0.369 mmol/L). Metformin was also able to cause a drastic decrease in the blood sugar level by a value similar to that of FR2DBW (1.26 mmol/L), this was significantly different from the control (5.06±0.089 vs 6.32±0.369 mmol/L (FIG. 7).

Metformin (25 mg/kg BW) and FR1DBY (50 mg/kg BW) both significantly reduced the blood glucose concentration similarly (FIGS. 7 and 13); at the 90 minute interval (5.07±0.089 vs 5.26±0.183 mmol/L respectively; p=0.359). Although the decrease in the amount of glucose in the blood was not significantly different from metformin, there was a difference of 1.06 mmol/L for FR1DBY at 50 mg/kg BW and the control (at the 90 minute interval). Therefore, FR1DBY was also effective at inducing a hypoglycaemic effect, similar to metformin.

Figure 8:
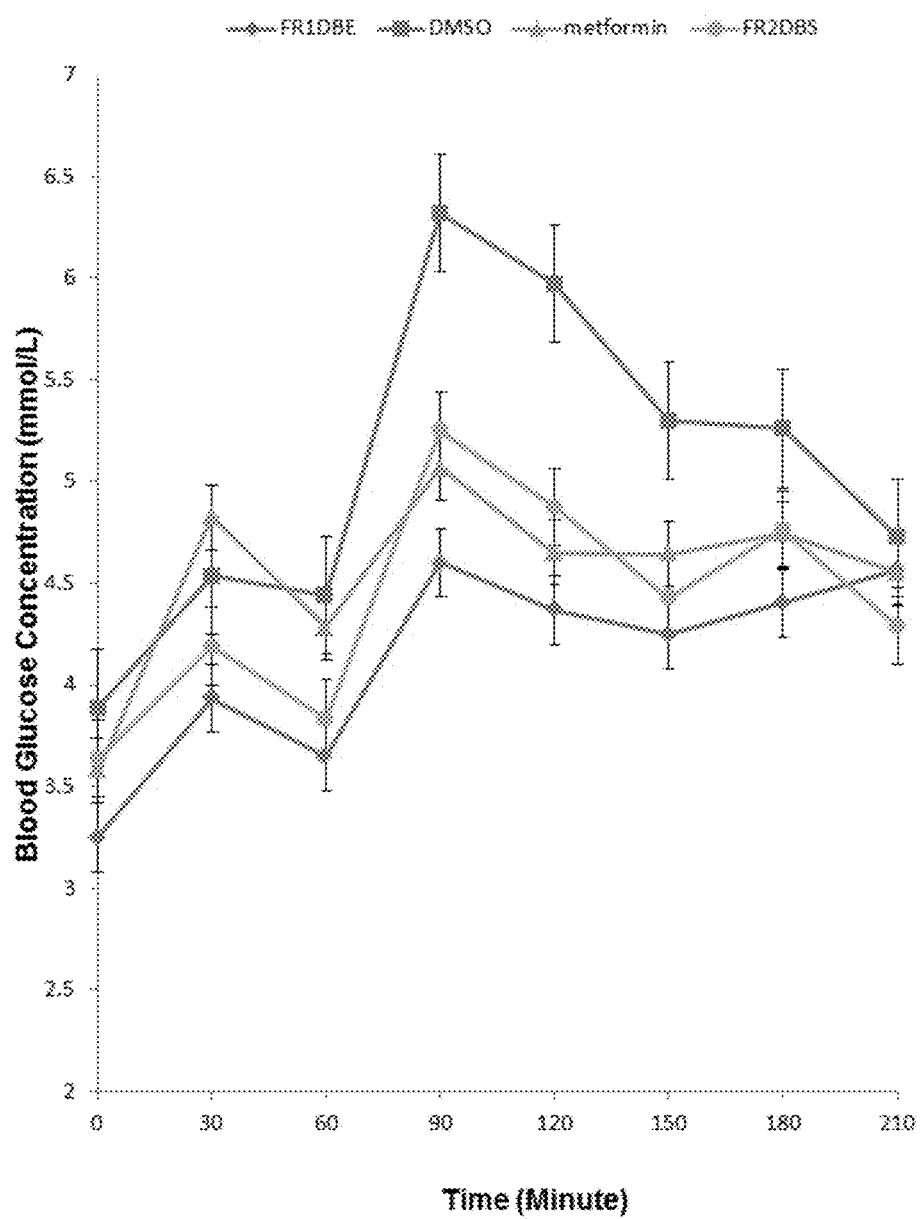
FIG. 8. GTC of FR2DBS and FR1DBE at 30 mg/kg BW vs metformin and DMSO (IV administration).
Figure 9:
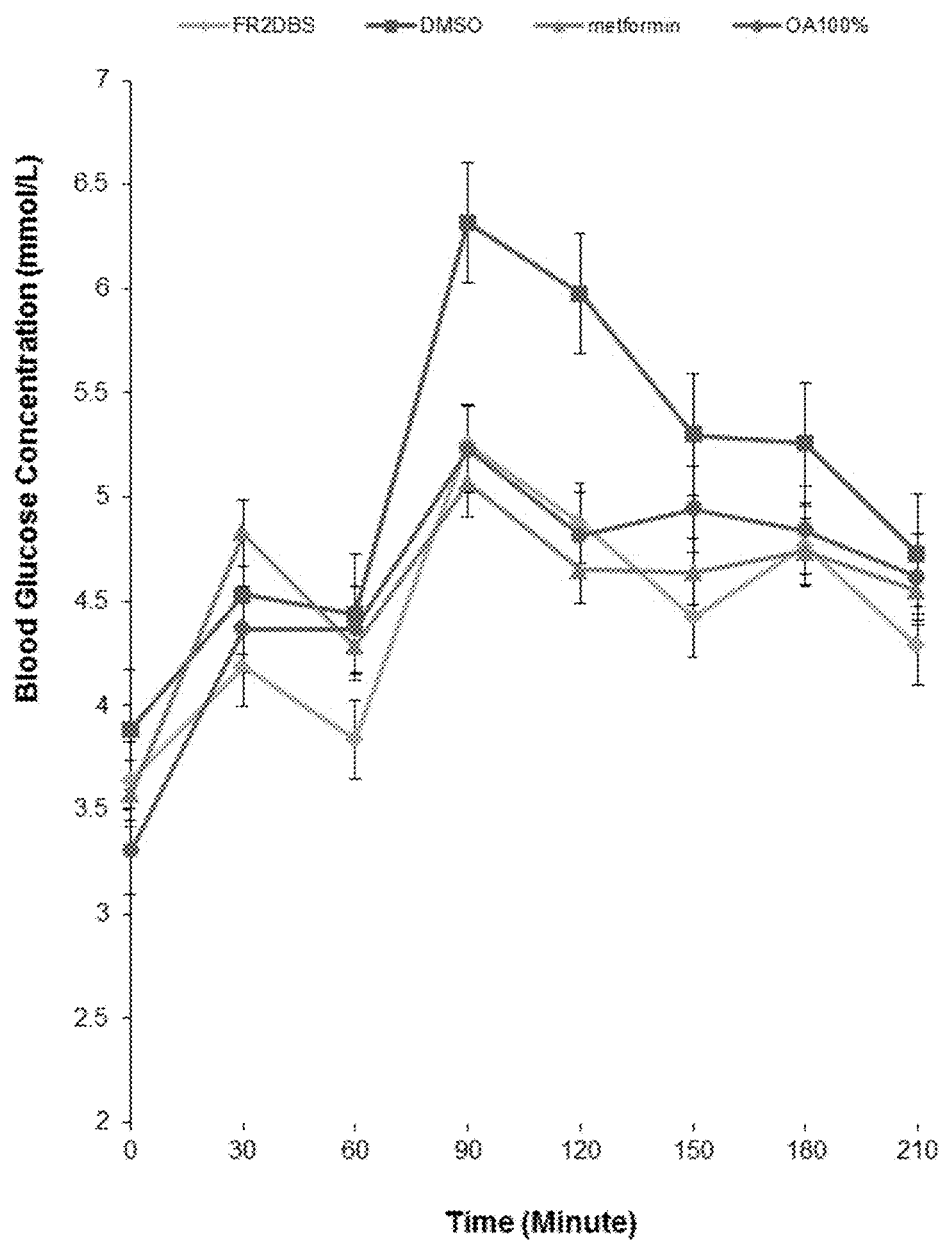
FIG. 9. GTC of isolated FR2DBS, commercial oleic acid (OA 100%) at 30 mg/kg BW vs DMSO and metformin (IV administration).

FIG. 8 showed that there was significant comparison between FR2DBS and metformin, as there was similarity in causing a hypoglycaemic effect. At the 90 minute interval, both FR2DBS and metformin were significantly lower than the control (p<0.05). A comparison of FR1DBE with metformin also showed the effectiveness of these waxy crystals as there was a similar reduction in the blood glucose concentration as metformin. During the fasting region of the GTC, FR1DBE was significantly lower than both the negative (DMSO) and positive (metformin) controls (p<0.05 for both controls). At the 90 minute interval, the area under the curve was less when FR1DBE was administered and compared with the metformin control, which showed 4.71±143 vs 5.07±0.089 mmol/L respectively, however, there was no significant difference between the two (p=0.058). This continued throughout the post-prandial curve as the probability was greater than 0.05 at all intervals. At the 120 minute interval (p=0.374) FR1DBE and metformin caused a similar reduction in the amount of glucose present within the blood.

In general, all the blood glucose values were lower than the control and indicated that these compounds (FR1DBE, FR1DBY, FR2DBW and FR2DBS) had hypoglycaemic activity. These isolated compounds are therefore responsible for the active component present in the crude hexane extract, which showed similar hypoglycaemic activity to the known oral hypoglycaemic agent.

Elucidation of the Structures of FR1DBY, FR2DBW, FR2DBS and FR1DBE.

The H and C-NMR analysis were done on compounds FR1DBY and FR2DBW. Long chain of carbon atoms containing methyl groups, an acidic group and a carbonyl group that formed a carboxylic group (COOH) were observed for both compounds.

Elucidation of the Structures of FR1DBY

FR1DBY contained sixteen carbon atoms, thirty-two hydrogens and two oxygen atoms that formed the carboxylic group of the acid. The chemical formula was similar to that of an unsaturated fatty acid as such further analysis was done to confirm the previous findings. Ultra-violet (UV) absorption was observed between approximately 240-300 nm with maximum absorption <1, this absorption was similar to carboxylic acid compounds. The long chain of carbon atoms (methylene groups; 2962-2850 $cm^{-1}$) was observed along with a carbonyl (C=O) group (1715-1695 $cm^{-1}$) and a carboxylic acid (COOH) group (3200-2500 $cm^{-1}$) were confirmed using FT-infrared absorption; thus indicating the presence of a fatty acid.

TABLE 3

The spectral data of compound FR1DBY (Palmitic Acid).

| Compound FR1DBY | Literature Value | Compound Value |
|---|---|---|
| UV | 240-300 nm | 274 |
| FT-IR | 2962-2850 cm$^{-1}$ | 2916.4 cm-1 |
|  | 1715-1695 cm$^{-1}$ | 2848.9 cm-1 |
|  | 3200-2500 cm$^{-1}$ | 1631.8 cm-1 |

The mass spectrum of FR1DBY was then deduced using gas-chromatography mass spectroscopy which showed a 96-99% match from the NIST library to be hexadecanoic acid (palmitic acid, PA).

Figure 13:
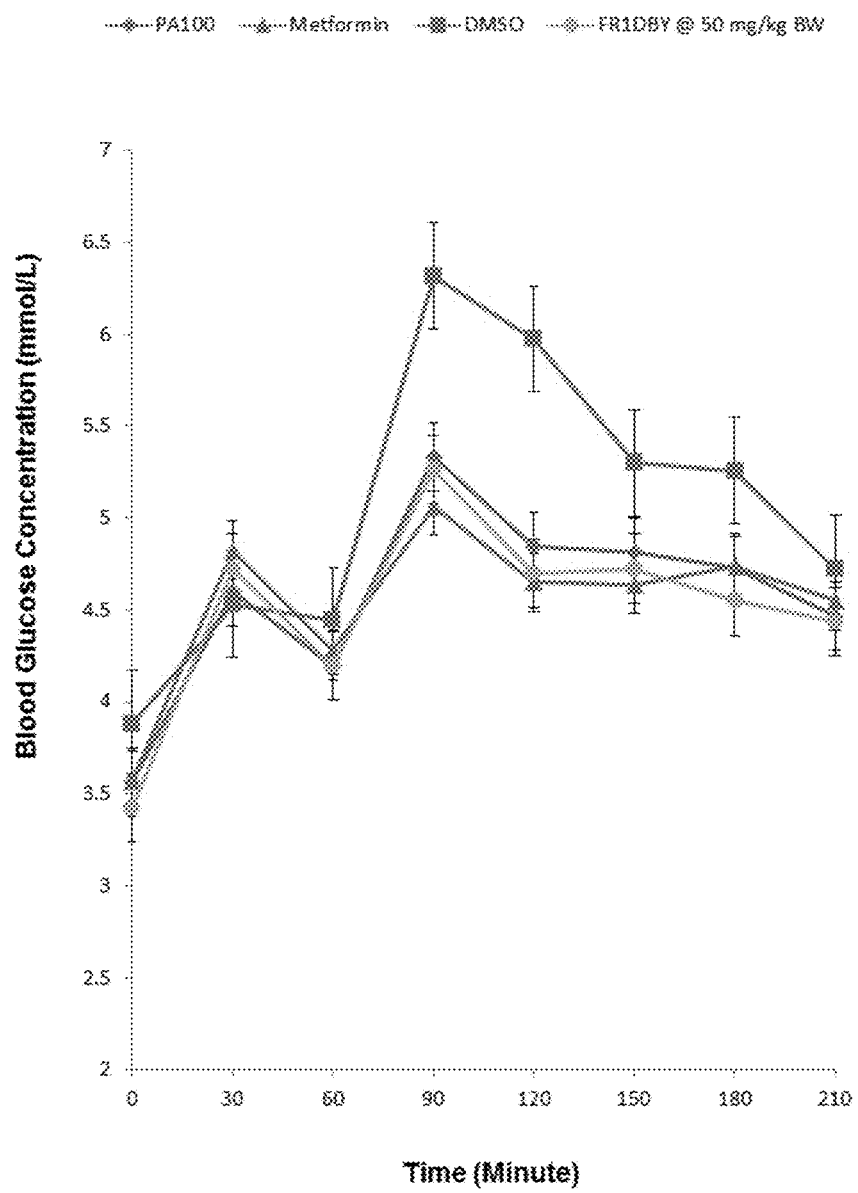
FIG. 13. GTC of PA100 (0% OA:100% PA) and isolated FR1DBY vs DMSO and metformin (IV administration).

A comparison carried out with FR1DBY (palmitic acid) and the commercially available palmitic acid confirmed the hypoglycaemic ability of the compound (FIG. 13). The spectroscopy results of FR1DBY cumulatively revealed the structure of hexadecanoic acid (Tables 3 and 4). The commercially available palmitic acid was able to significantly lower the blood glucose concentration however the hypoglycaemic effect was more significant with the palmitic acid isolated (FR1DBY) from the E. camaldulensis.

Elucidation of the Structures of FR2DBW (Combined Fatty Acids)

The elucidation of the structure of FR2DBW using $^1$H and $^{13}$C NMR showed that the structure was somewhat similar to that of FR1DBY. However, more carbon atoms were attached and there was also a trans-carbon to carbon double bond present which depicted an unsaturated compound. Table 4 shows that FR2DBW was absorbed between 245-345 nm of the UV spectrum which is due to the carbonyl group of the acid. There were more than one carbonyl group of an acid being observed (1715-1695 cm$^{-1}$), a double bond (1650-1590 cm$^{-1}$) and two distinct peaks due to the presence of two long chain methylene rich compounds (2962-2850 cm$^{-1}$) when the FT-IR analysis was done. The GC-MS of FR2DBW identified the compound to be oleic acid (OA) and palmitic acid (PA) in a ratio of 2.3 to 1 (area percent respectively). This also had a high percentage identification of 92-98% similarity to the known compounds according to the NIST library.

TABLE 4

The spectral data of compound FR2DBW (Combined Fatty Acids).

| Compound FR2DBW (Combined fatty acids) | Literature Value | Actual Value |
|---|---|---|
| UV | 240-300 nm | 277 and 283 nm |
| FT-IR | 2962-2850 cm$^{-1}$ | 2921.6 cm$^{-1}$ |
|  | 1715-1695 cm$^{-1}$ | 1731.8 cm$^{-1}$ |
|  | 3200-2500 cm$^{-1}$ | 3131.8 cm$^{-1}$ |
|  | 1650-1590 cm$^{-1}$ | 1461.8 cm$^{-1}$ |
|  | 2962-2850 cm$^{-1}$ |  |

Elucidation of the Structure of FR2DBS (Oleic Acid) Spectroscopy

The UV absorption of FR2DBS was between 247-303 nm (Table 5) as shown in the Appendix and the FT-IR showed similar patterns to FR2DBW at several peaks, such as the double bond being present between 1650-1590 cm-1 (1622.53 cm-1) and the methylene chain present between 2962-2850 cm-1 (Table 5) which can be seen in Appendix I. FR2DBS spectroscopy results was the further elucidated using GC-MS and was confirmed to be octadecanoic acid (oleic acid, OA).

TABLE 5

The spectral data of compound FR2DBS (Combined Oil).

| Compound FR2DBS | Literature Value | Actual Value |
|---|---|---|
| UV | 245-300 nm | 247-303 nm |
| FT-IR | 2962-2850 cm$^{-1}$ | 2961.92-2848.24 cm$^{-1}$ |
|  | 1650-1590 cm$^{-1}$ | 1500 cm$^{-1}$ |
|  | 2962-2850 cm$^{-1}$ | 2923.57-2853.55 cm$^{-1}$ |
|  | 1470.88 and 716.20 cm$^{-1}$ |  |

Elucidation of Compound FR1DBE (Eicosane).

Elucidation of FR1DBE using UV spectroscopy had an absorbance between 246-303 nm lambda max (Table 6) which is within the region of absorption of a long chain compound. The FT-IR showed functional groups at peaks within the 2962-2850 cm-1 region (2961.92-2848.24 cm-1) which was also similar to that of the methylene chain and below 1500 cm-1 (1470.88 and 716.20 cm-1) which is typical of C—H deformations. The gas chromatography-mass spectroscopy of compound FR1DBE had a high percentage identification to have the structure of eicosane at 99% identified from the NIST library (Table 7).

TABLE 6

The spectral data of compound FR1DBE (Eicosane).

| Compound FR1DBE | Literature Value | Actual Value |
|---|---|---|
| UV | 245-300 nm | 247-303 nm |
| FT-IR | 2962-2850 cm$^{-1}$ | 2961.92-2848.24 cm$^{-1}$ |
|  | 1650-1590 cm$^{-1}$ | 1500 cm$^{-1}$ |
|  | 2962-2850 cm$^{-1}$ | 2923.57-2853.55 cm$^{-1}$ |
|  | 1470.88 and 716.20 cm$^{-1}$ |  |

TABLE 7

The GC-MS spectral data of FR1DBE (Eicosane).

| $T_R$/min | Compound[a] | % Area | ID[b] |
|---|---|---|---|
| 21.21 | Eicosane | 99.62 | GC-MS, Match with standard of eicosane |

[a]Elution order on HP capillary column.
[b]GC-MS identification by Gas Chromatography -Mass spectrometry, and a Matching with an Authentic Sample of Eicosane in Three Different temperature Programs.

TABLE 8

The Gas Chromatogram of FR1DBE (Eicosane).

| Temperature Change | Retention Time of Standard Eicosane (Minute) | Retention Time of Isolated FR1DBE (Minute) |
|---|---|---|
| 1 | 3.04 | 3.05 |
| 2 | 5.42 | 5.43 |
| 3 | 3.10 | 3.11 |

Bioassay (OGTT) of the Different Ratios of Oleic Acid (OA): Palmitic Acid (PA)

Figure 10:
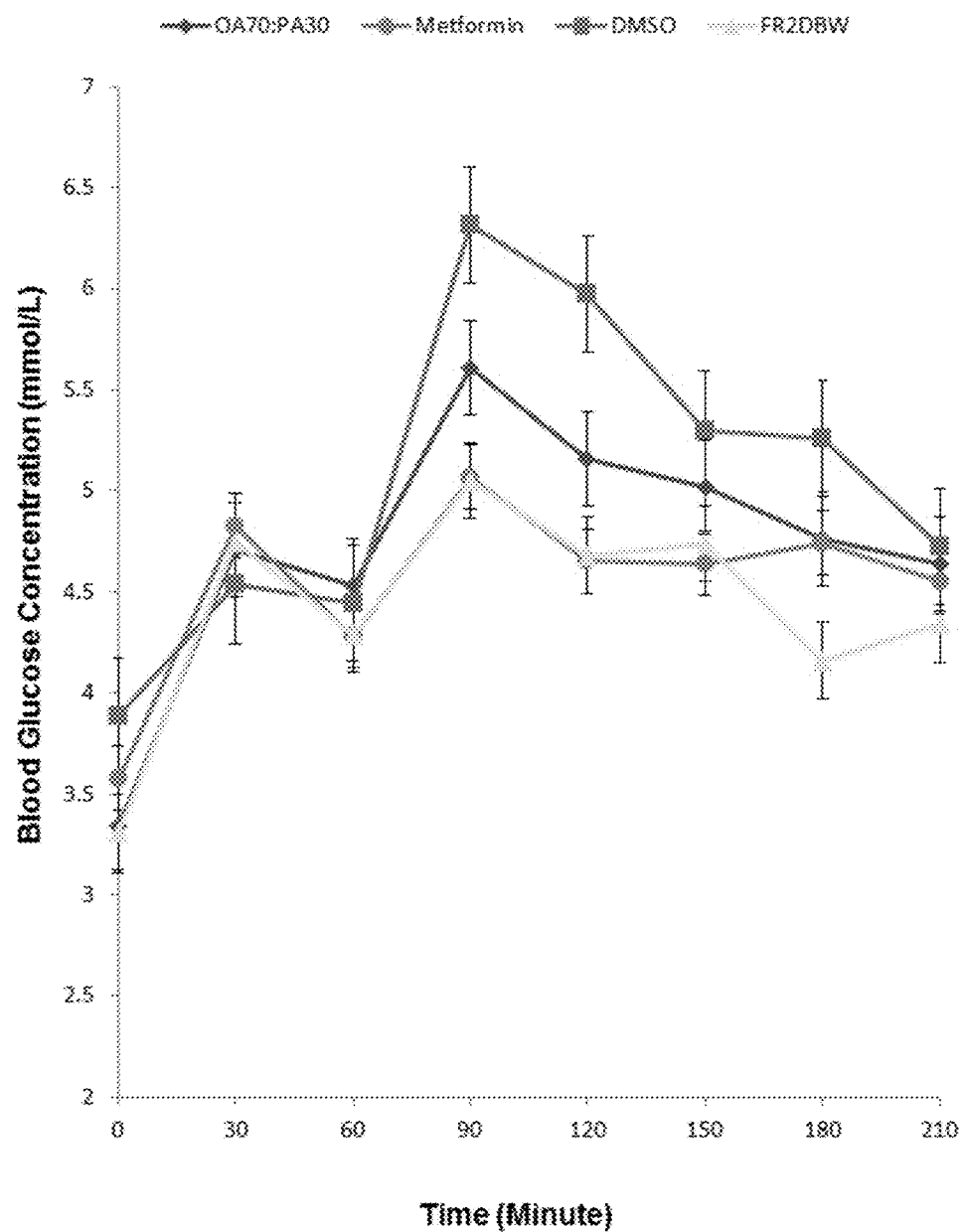
FIG. 10. GTC of isolated FR2DBW and commercial OA:PA (70%:30%) at 30 mg/kg BW vs DMSO and metformin (IV administration).
Figure 11:
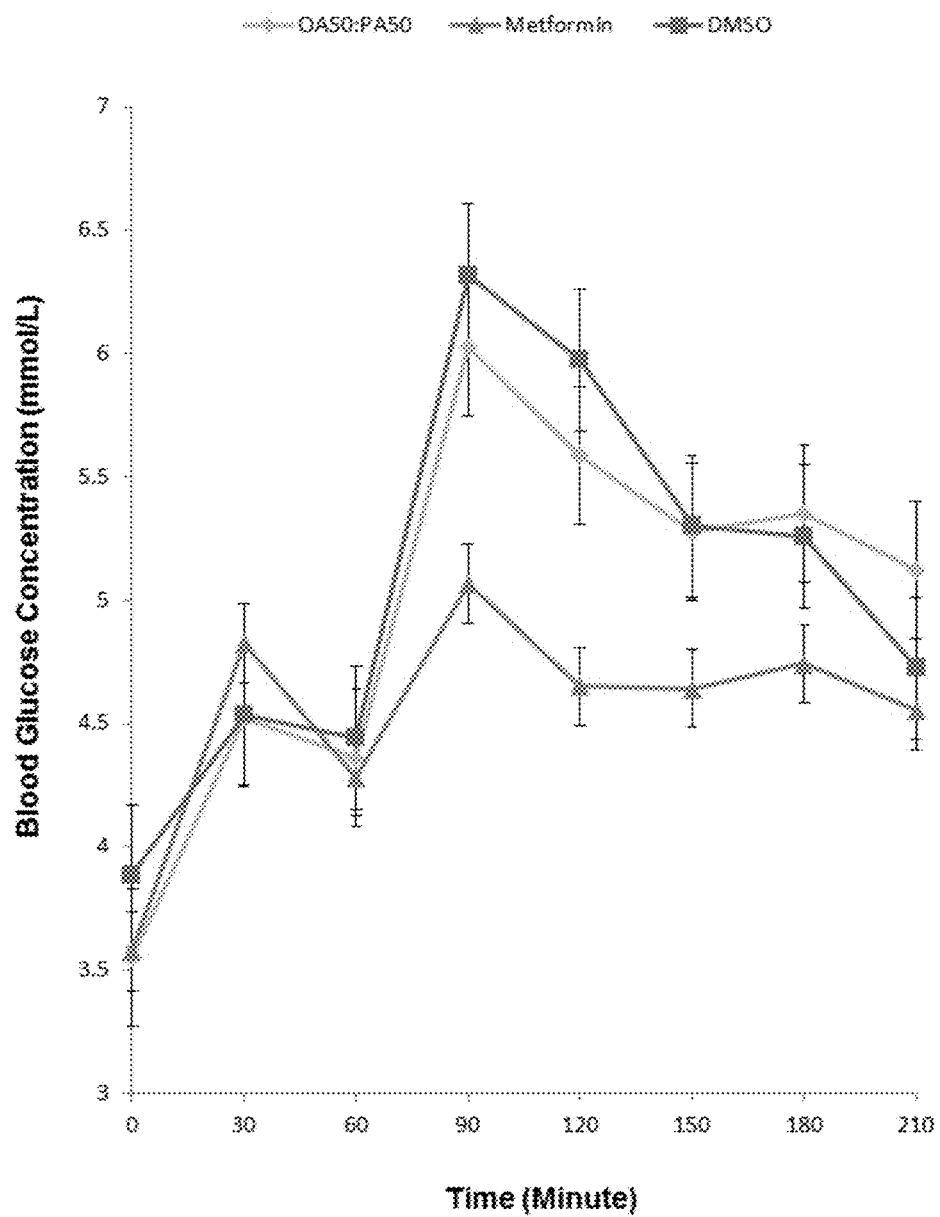
FIG. 11. GTC of OA:PA (50%:50%) vs metformin and DMSO (IV administration).

The GTC of the different ratios (FIGS. 9-13) showed the hypoglycaemic effect of the mixtures of oleic acid and palmitic acid (Table 8). The overall synergistic effect was significantly lower than the DMSO control at a ratio of 70% oleic acid:30% palmitic acid. This was the ratio extracted from the plant (FR2DBW) and was most significant compound isolated in reducing the blood glucose concentration (FIG. 10).

The effect of the varying dosages of these fatty acids was done, thus showing the synergistic effect.

Figure 12:
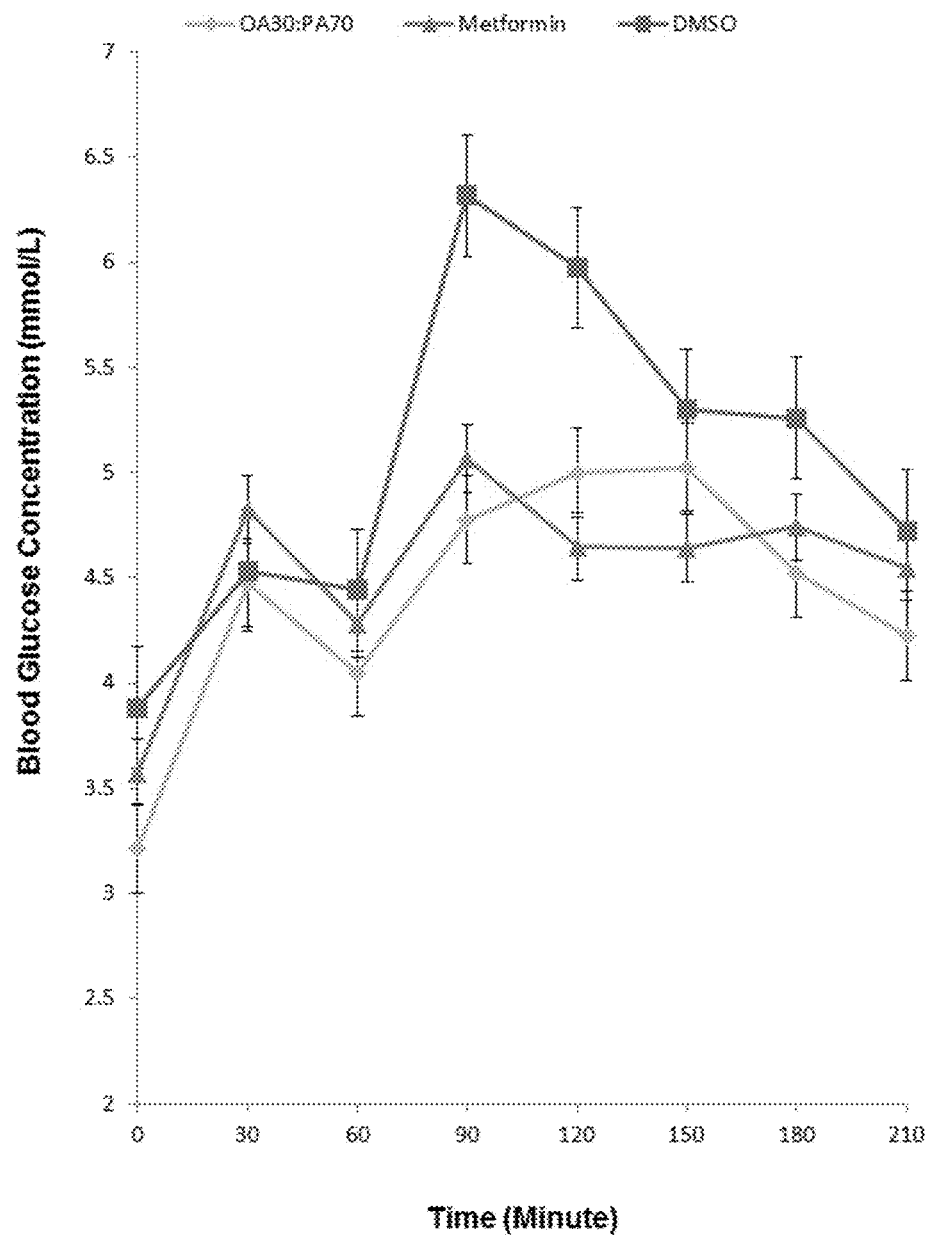
FIG. 12. GTC of OA:PA (30%:70%) vs metformin and DMSO (IV administration).

Oleic acid at 100% (OA100) showed some amount reduction of the blood glucose concentration (FIG. 9) which was significantly different from the control. During the post-prandial region there was significant reduction of the blood glucose concentration, except for the 150 minute interval (p=0.261) and subsequently. This ratio lowered the glycaemic peak (at the 90 minute interval) similarly to metformin (5.23±0.14 vs 5.07±0.09 mmol/L respectively; p=0.324). In FIG. 10, the OA:PA (3:1) ratio showed the most significant decrease in the blood glucose concentration. There was no significant difference between OA:PA at 1:1 (50%:50%) ratio (FIG. 11) and the control, therefore metformin was more significant in reducing the blood glucose concentration. At the 90 minute interval, this ratio gave 6.03±0.165 vs 6.32±0.37 mmol/L for the control (p=0.482) and therefore the compound OA; PA at 50% each was unable to lower the glycaemic peak significantly. When compared with metformin p=0.0003, showing that metformin was much more significant in reducing the glycaemic peak. When administered in a 1:3 (OA:PA) ratio, there was a decrease in the post-prandial region which was significantly different from the control (p−0.001 at the 90 minute interval) (FIG. 12). However, metformin reduced the glycaemic peak more significantly than the 30% OA: 70% PA mixture (4.78±1.0 vs 5.07±0.09 mmol/L; p=0.048). The administration of PA at 100% (FIG. 13) had a significant decrease in the blood glucose concentration when compared with the control (p=0.041 at the 90 minute interval). Thus a range from 60%: 40% oleic:palmitic acid would be the most ideal combination range having a hypoglycaemic effect.

TABLE 9

The Effect of Combinations of Oleic:Palmitic Acids used.

| Sample | Figure | Octadecanoic Oleic) Acid (%) | Hexadecanoic Palmitic) Acid (%) | Hypoglycaemic effect compared with control |
| --- | --- | --- | --- | --- |
| OA | 36 | 100 | 0 | Significant |
| OA:PA (3:1) | 37 | 70 | 30 | Significant |
| OA:PA (1:1) | 38 | 50 | 50 | Not significant |
| OA:PA (1:3) | 39 | 30 | 70 | Significant |
| PA | 40 | 0 | 100 | Significant |

Oral Administration of the Hypoglycaemic Compounds

A comparison was done of the oral administration of the fatty acids with the respective oil on the blood glucose concentration by using the OGTT done in order to deduce their effect. Oleic and palmitic acids are major constituents of olive oil and coconut oil respectively. As such, comparisons were made after OGTTs were carried out to determine the effect of olive oil, coconut oil and the combined product (2.3 olive oil:1 coconut oil), on blood glucose concentration.

Figure 29:
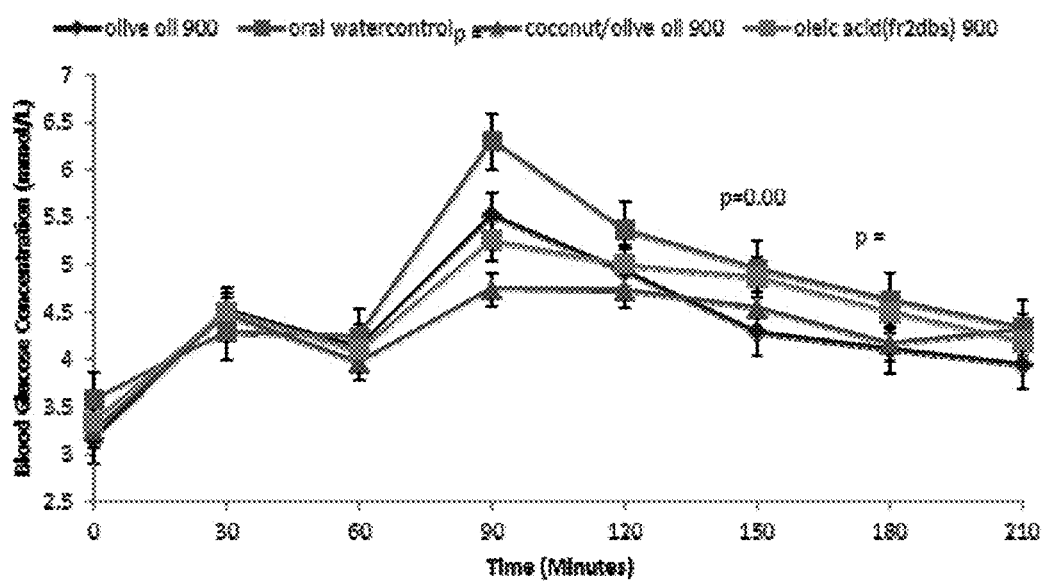
FIG. 29. GTC of olive oil, coconut/olive oil (ratio) and oleic acid administered orally at 900 mg/kg BW.

An analysis of glucose tolerance curves to compare olive oil, FR2DBS (oleic acid) and the combined oil (FR2DBW; 2.3 olive oil:1 coconut oil) at 900 mg/kg BW vs the control (water) all administered orally, was conducted. The olive oil and the oleic acid were able to reduce the post-prandial glucose level, however, the combined oil was the most effective in lowering the blood glucose level. At the 90 minute interval this was evident as there was 4.74±0.13 mmol/L of glucose present which was significantly less than the control (6.03±0.26 mmol/L). See also FIG. 29.

Palmitic acid (FR1DBY) at the same dosage was able to significantly lower the area under the glucose tolerance curve one hour after the glucose load was administered (p=0.01 and 0.002 at 120 and 150 minute intervals respectively) and therefore was hypoglycaemic only after food (glucose) was present as it significantly reduced the blood glucose concentration.

The coconut oil was not able to reduce the blood glucose level significantly when compared with the control. During the post-prandial period of the GTC there was no difference shown with the administration of the coconut oil (p=0.227 and 0.125 at the 90 and 120 minutes intervals respectively).

The combined oil (FR2DBW/olive oil:coconut oil) was more effective in producing a hypoglycaemic effect and a significantly lower glycaemic peak when compared with the coconut oil (4.74±0.13 mmol/L vs 5.81±0.10 mmol/L respectively). The increase in the blood glucose concentration after the glucose load was considerably less for the combined oil than the control and continued to decrease for the remaining 2½ hours of post-prandial.

The comparison between the combined oil (olive oil:coconut oil) and FR2DBW compound at 900 mg/kg BW showed that both were significantly hypoglycaemic. At the 90 minute interval the compound FR2DBW had a lower glycaemic peak (5.05±0.18 mmol/L) but was not significantly different from the combined oil (4.74±0.13 mmol/L; p=0.183). Therefore, both were effective at reducing the blood glucose concentration after a meal is ingested.

The results above demonstrate that cooking oils, and not just fatty acids, exhibit hypoglycaemic properties.

Oral Administration of the Combined Fatty Acids (FRDBW), Oleic Acid (FR2DBS) and Palmitic Acid (FR1DBY)

The compound FR2DBW (combined OA:PA) was able to significantly reduce the blood glucose concentration when administered intravenously (FIG. 10), and as such, oral dose dependent OGTTs were carried out to determine the most effective hypoglycaemic dosage. Preliminary dosages of 200 and 500 mg/kg BW were done. These dosages appeared to have no effect on the blood glucose level and as such, higher dosages of 700 and 900 mg/kg BW were done.

When FR2DBW was administered at 700 mg/kg BW (FIG. 15), there was a significant reduction in the area under the curve. The higher dosage (900 mg/Kg BW; FIG. 16) of FR2DBW also reduced the glycaemic peak and was not significantly different at the 90 minute interval (p=0.099). A comparison done with an oral administration of metformin at 200 mg/kg BW also concurred this finding of increased efficacy of FR2DBW with an increase in the dosage, thus showing the dosage at 900 mg/kg BW having a lower area under the curve.

FR1DBY and FR2DBS were also able to lower the blood glucose concentration when administered orally at a dosage of 900 mg/Kg BW (FIGS. 14-16). As such, these isolated compounds may be administered orally to aid in the reduction of hyperglycaemia in T2DM, as the effect on the blood glucose level was comparable to that produced when metformin is administered orally.

The Effect of FR1DBY (Palmitic Acid) on Haemodynamic Parameters

There was also a significant decrease in the blood pressure when FR1DBY was administered to the rats. The effect of FR1DBY on the systolic blood pressure (FIG. 17) showed that it was significantly lower than the control throughout the 30 minutes (p<0.05). The compound had reduced the systolic blood pressure from 153.35±3.62 mmHg (DMSO) to 123.42±1.27 mmHg (FR1DBY) at the 10 minute interval, which was very significant, even when compared with captopril (130.92±1.50 mmHg at 10 minutes; p=0.0003). Captopril produced a more significant reduction than FR1DBY for the remaining 20 minutes of the experiment (p<0.05) and even more so when compared with the control, DMSO. This is depicted throughout the graph.

Figure 18:
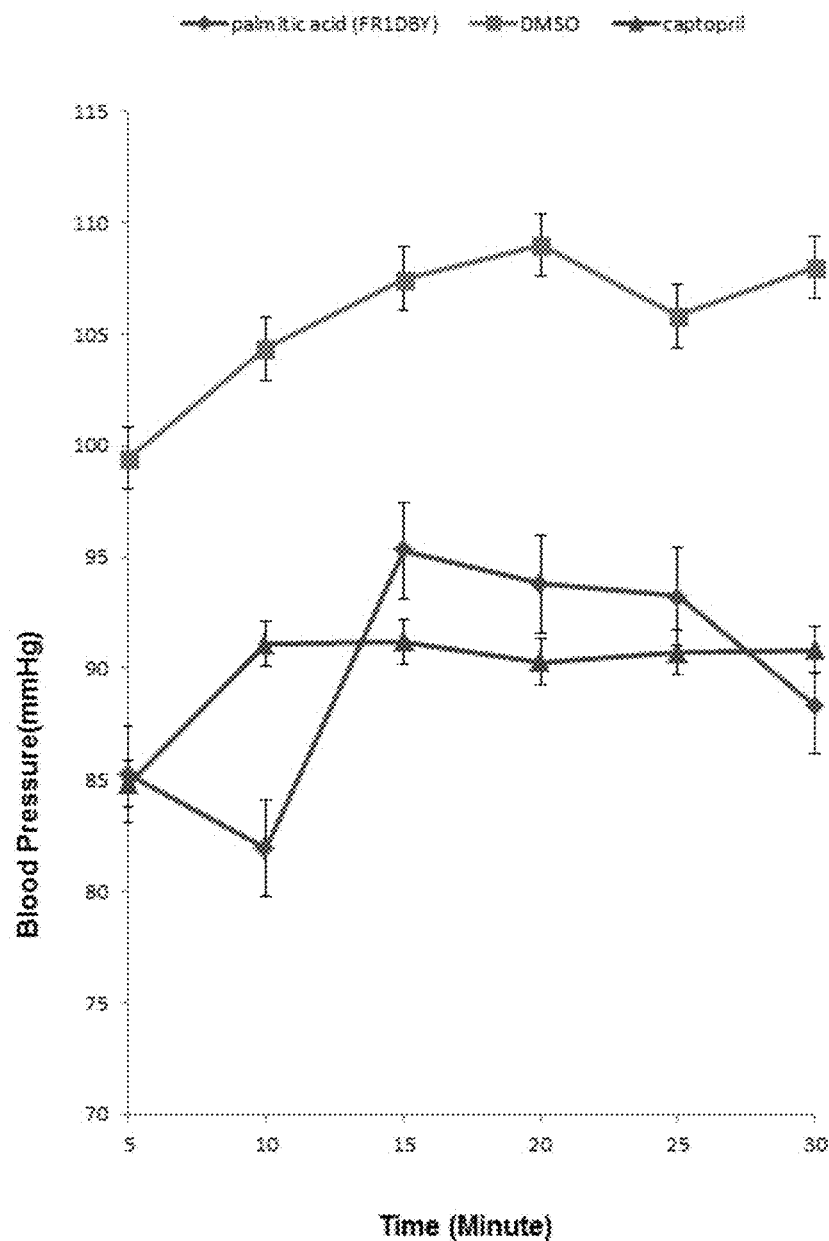
FIG. 18. DBP of palmitic acid (FR1DBY) (at 50 mg/kg BW), and captopril (30 mg/kg BW) vs DMSO.

At the 15 minute interval the systolic control (158.45±2 8 mmHg) was significantly higher than that of captopril (111.93±2.61 mmHg) and also FR1DBY (139.0±3.5 mmHg). FIG. 18 showed the effect of FR1DBY on the diastolic blood pressure. There was no significant difference between FR1DBY and captopril in reducing the diastolic rate ($p=0.18$ and 0.33 at the 15 and 20 minute intervals respectively), except at the 10 minute interval, where FR1DBY was significantly lower than the positive control (81.93±1.74 vs 91.09±1.90 mmHg; $p=0.002$). Both were more effective, in causing a decrease in the diastolic blood pressure, than DMSO which was 109.0±1.95 mmHg at the 20 minute interval, compared with 93.79±3.14 mmHg (FR1DBY) and 93.30±1.58 mmHg (captopril).

Figure 17:
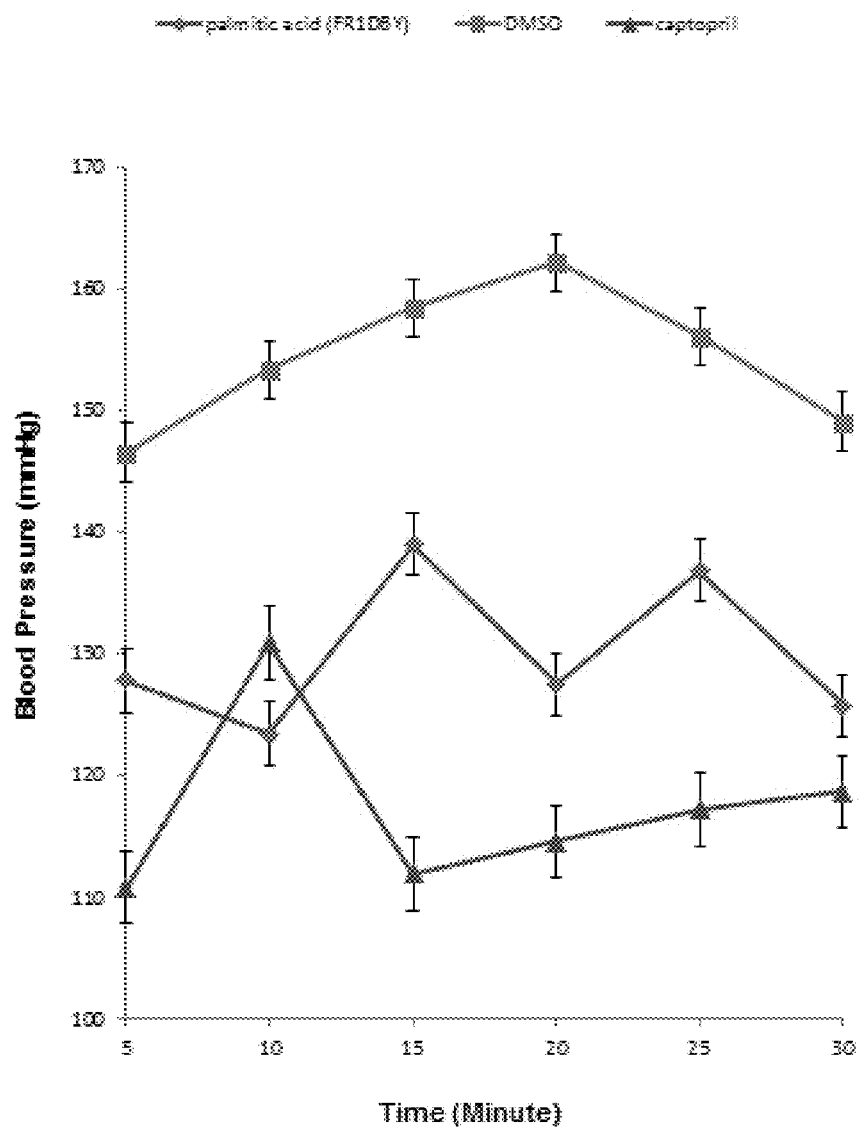
FIG. 17. SBP of palmitic acid (FR1DBY) (at 50 mg/kg BW), and captopril (30 mg/kg BW) vs DMSO.
Figure 19:
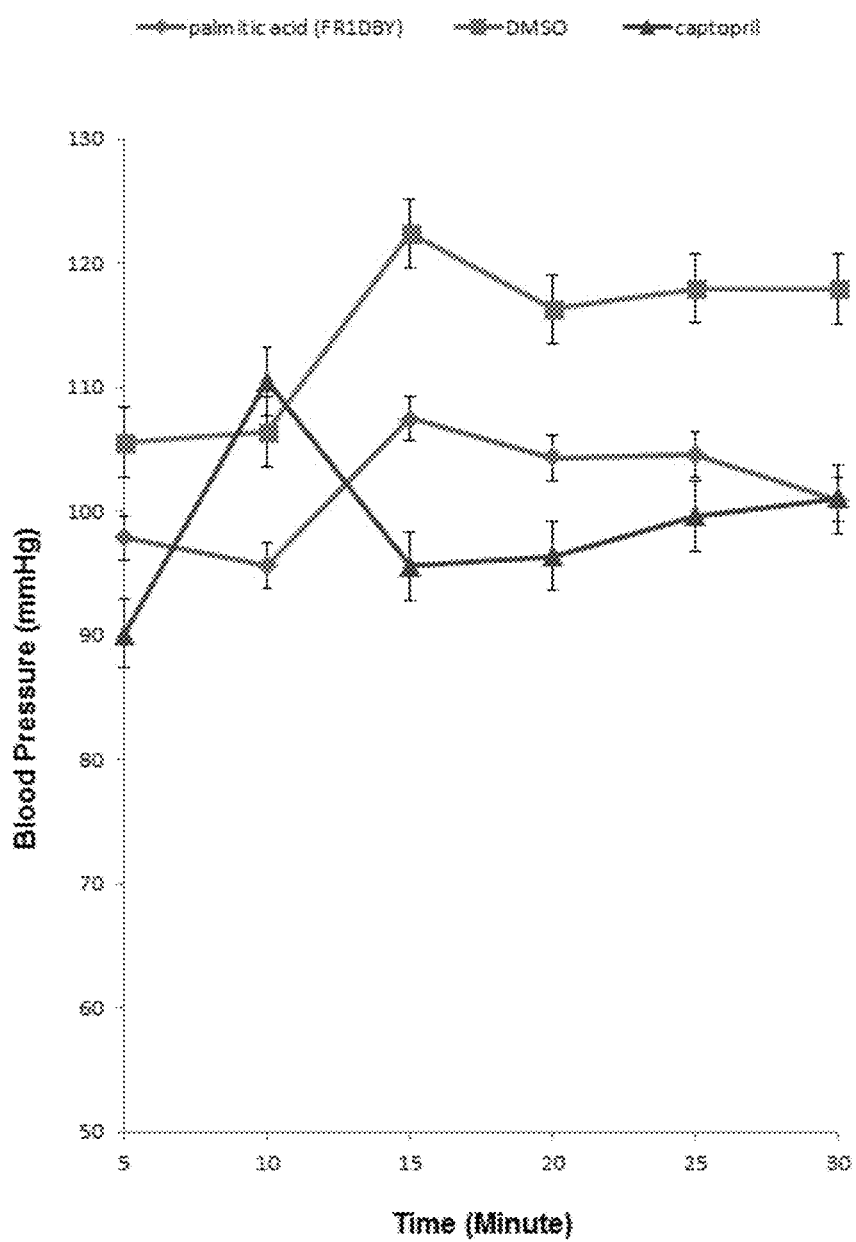
FIG. 19. MAP of palmitic acid (FR1DBY) (at 50 mg/kg BW), and captopril (30 mg/kg BW) vs DMSO.

The mean blood pressure was also significantly affected by FR1DBY in that there was an overall reduction in the mean arterial pressure being exerted when compared with the control at 10 minute interval ($p=0.008$) (FIGS. 17, 18 and 19). This drop is due to the fact that DMSO caused 106.42±3.28 mmHg of pressure to be exerted while FR1DBY was much lower with 95.67±1.77 mmHg After the 10 minute interval captopril resulted in a slightly lower mean arterial blood pressure, but was significantly lower at the 20 minute interval ($p=0.82$) where FR1DBY was 104.23±3.08 mmHg and captopril was 105.07±2.06 mmHg Although FR1DBY was able to lower the blood pressure similar to that of captopril. However, the mechanism of action seems possibly different as FR1DBY caused an overall reduction in the heart rate whereas captopril did not affect it.

Figure 20:
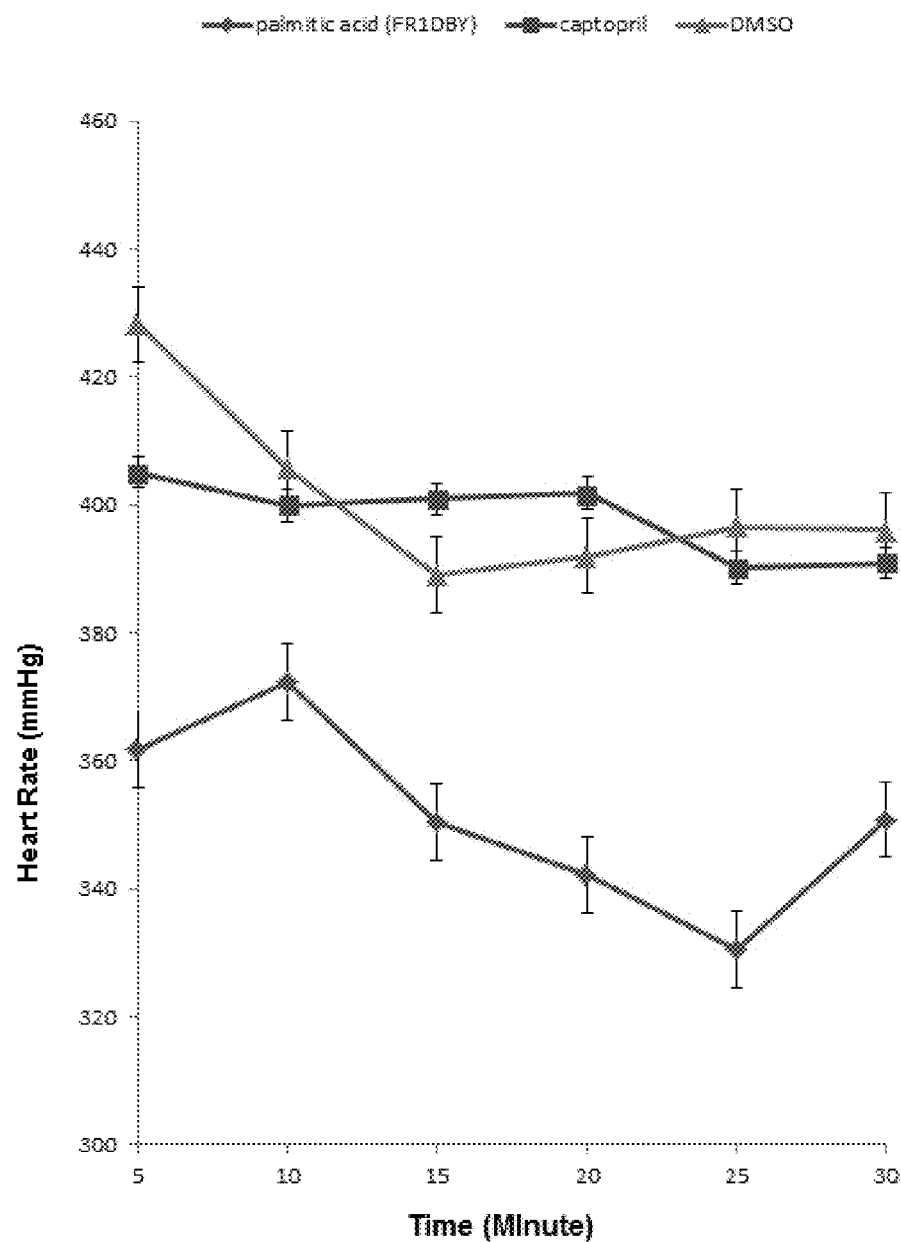
FIG. 20. The effect of palmitic acid (FR1DBY) (at 50 mg/kg BW) and captopril (30 mg/kg BW) vs DMSO on heart rate.

FR1DBY caused a significant reduction in the heart rate throughout the 30 minutes of the experiment (FIG. 20). At the 10 minute interval FR1DBY reduced the heart rate more significantly when compared with the controls (372.40±3.07 mmHg for FR1DBY vs 412±6.91 mmHg for captopril; $p<0.05$; and vs 405±8.95 mmHg for DMSO; $p=0.002$). $P<0.05$ at the 15 minute interval also showing a significant decrease, while there was no significant difference between the positive and negative controls' heart rate.

Captopril is a known ACE inhibitor which initiates vasodilation, however FR1DBY can be reducing the blood pressure by a mechanism similar to that of the beta blockers or the calcium channel blockers. In the case of the beta blockers, FR1DBY can reduce the heart rate and its output by stimulating a decrease in the hormone epinephrine that is released and in effect results in a reduced blood pressure or reducing the rate at which the heart contracts due to termination of the movement of calcium ions which will lead to a widening of the blood vessels and thus a lower blood pressure as with the calcium channel blockers.

The Effect of FR2DBW on Haemodynamic Parameters

Figure 21:
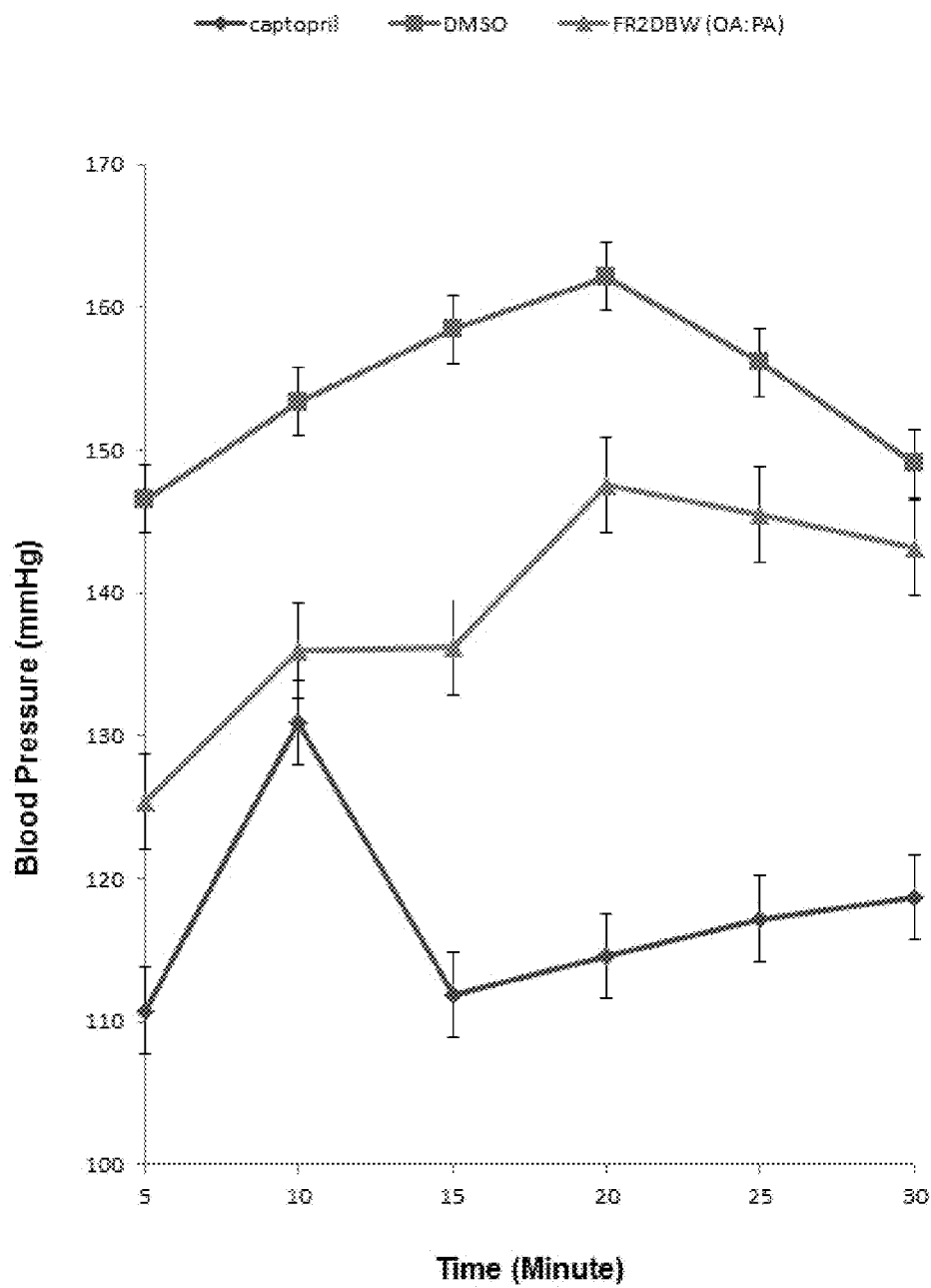
FIG. 21. SBP of oleic:palmitic acid (FR2DBW) and captopril at 30 mg/kg BW vs DMSO.
Figure 22:
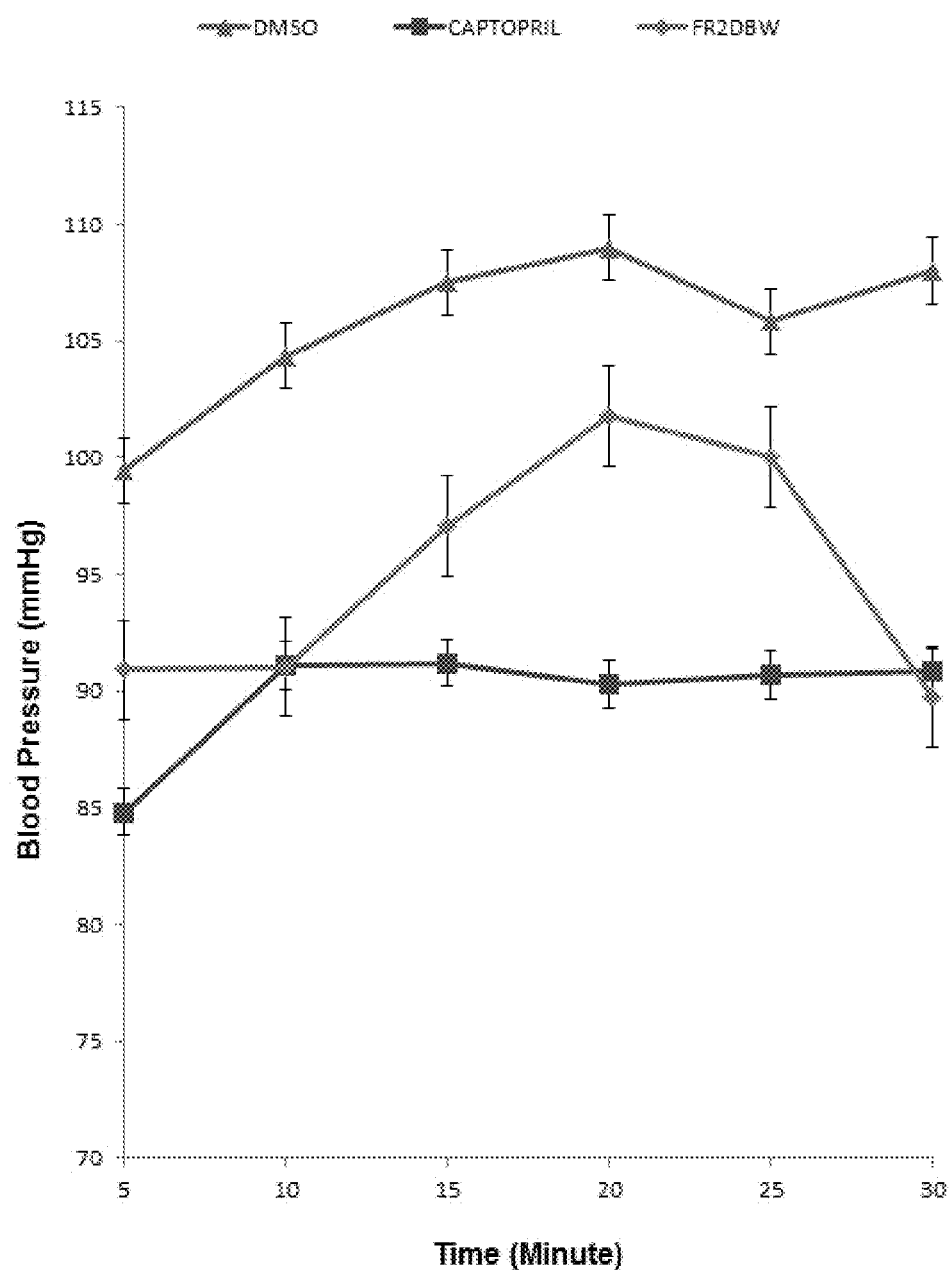
FIG. 22. DBP of oleic:palmitic acid (FR2DBW) and captopril at 30 mg/kg BW vs DMSO.

The sample FR2DBW (OA:PA combined) showed significant reduction in the haemodynamic parameters FIGS. 21-24). The systolic blood pressure (SBP) of FR2DBW was significantly lower than that of the negative control (FIG. 21). At the 15 minute interval there was a decrease from 158.45±2.81 mmHg to 136.21±2.60 mmHg due to FR2DBW; and this continued throughout for another 10 minutes of the experiment ($p<0.05$). The positive control, captopril, was able to more effectively reduce the systolic rate more than FR2DBW, except at the 10 minute interval where the combined fatty acids (FR2DBW) recorded 135.93±2.8 mmHg while captopril gave 130.93±1.50 mmHg ($p=0.056$). Nonetheless, both were significantly lower than the control.

For the first 10 minutes, the diastolic blood pressure (DBP) of FR2DBW was not significantly different from that of captopril (91±2.23 vs 91±1.90 mmHg respectively; $p=0.98$), however, captopril continued to be constant while FR2DBW gave a slight increase but was still lower than the control. Thus FR2DBW had an overall reduced diastolic rate, even at the 20 minute interval where there was 109±1.95 mmHg of pressure being exerted due to DMSO and 101.79±2.35 mmHg due to the presence of FR2DBW ($p=0.02$, FIG. 22).

Figure 23:
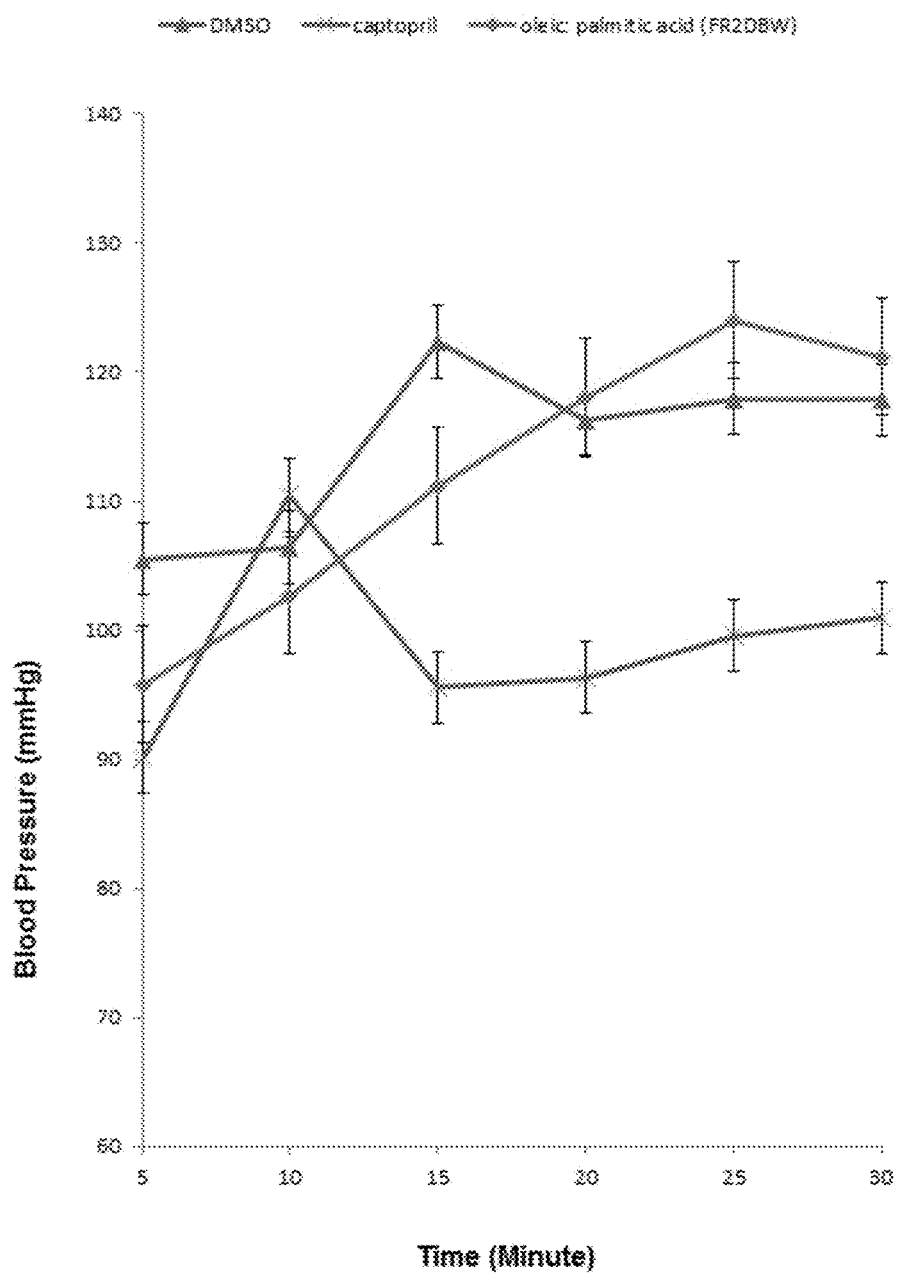
FIG. 23. MAP of oleic:palmitic acid (FR2DBW) and captopril at 30 mg/kg BW vs DMSO.

For the mean arterial pressure (MAP) captopril was significantly lower than both the DMSO and FR2DBW ($p<0.0.05$; FIG. 23). However, at the 10 minute interval, FR2DBW was able to exert less pressure on the walls of the blood vessels (102.70±2.63 vs 110.86±1.71 mmHg for FR2DBW and captopril respectively; $p=0.03$), however, this was not more significant than the control, DMSO ($p=0.4$). Therefore, FR2DBW caused some amount of lowering of the mean arterial pressure, however due to the increase diastolic rate that was experienced, which is two-thirds (one-third systolic) of the mean arterial blood pressure, there was no significant difference after the 15 minute interval had passed.

Figure 24:
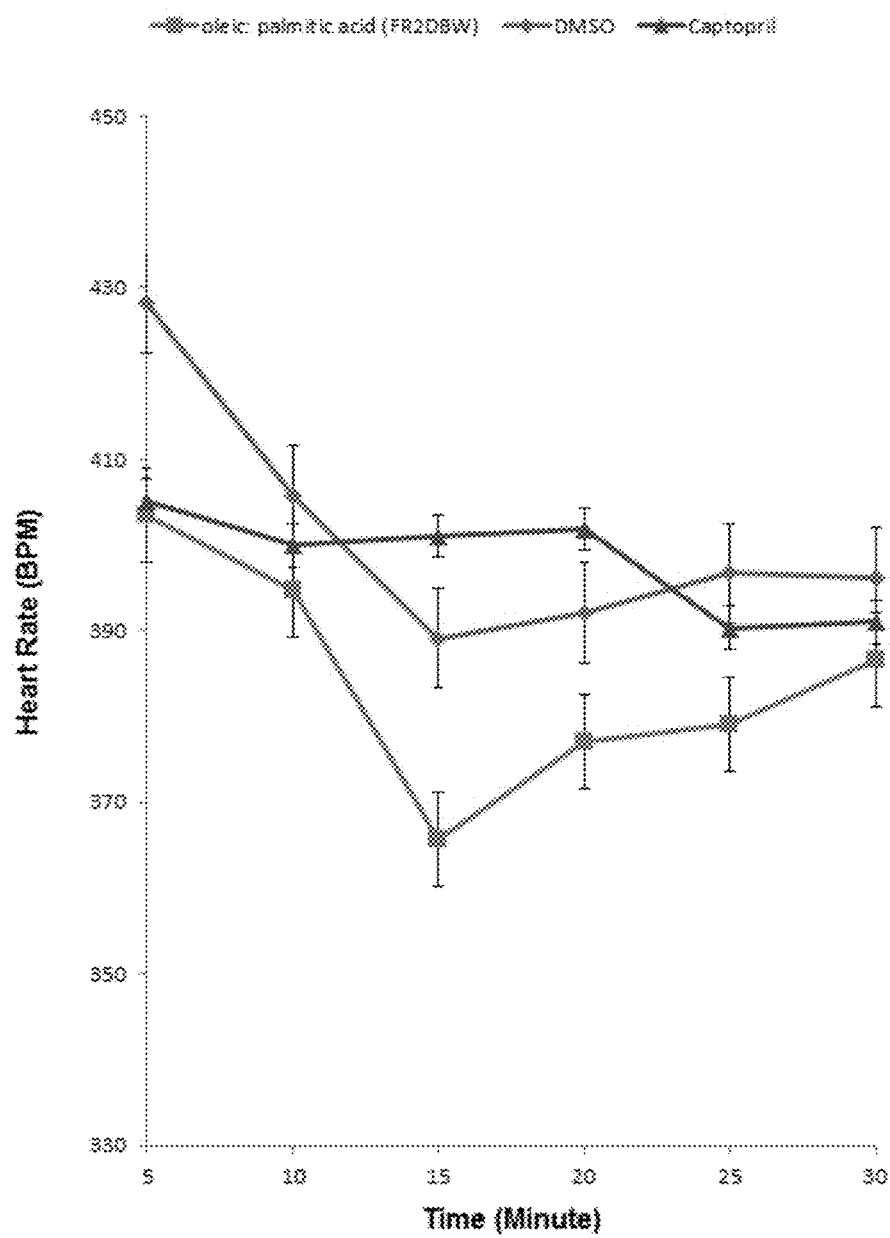
FIG. 24. The effect of oleic:palmitic acid (FR2DBW) and captopril at 30 mg/kg BW vs DMSO on the heart rate.
Figure 25:
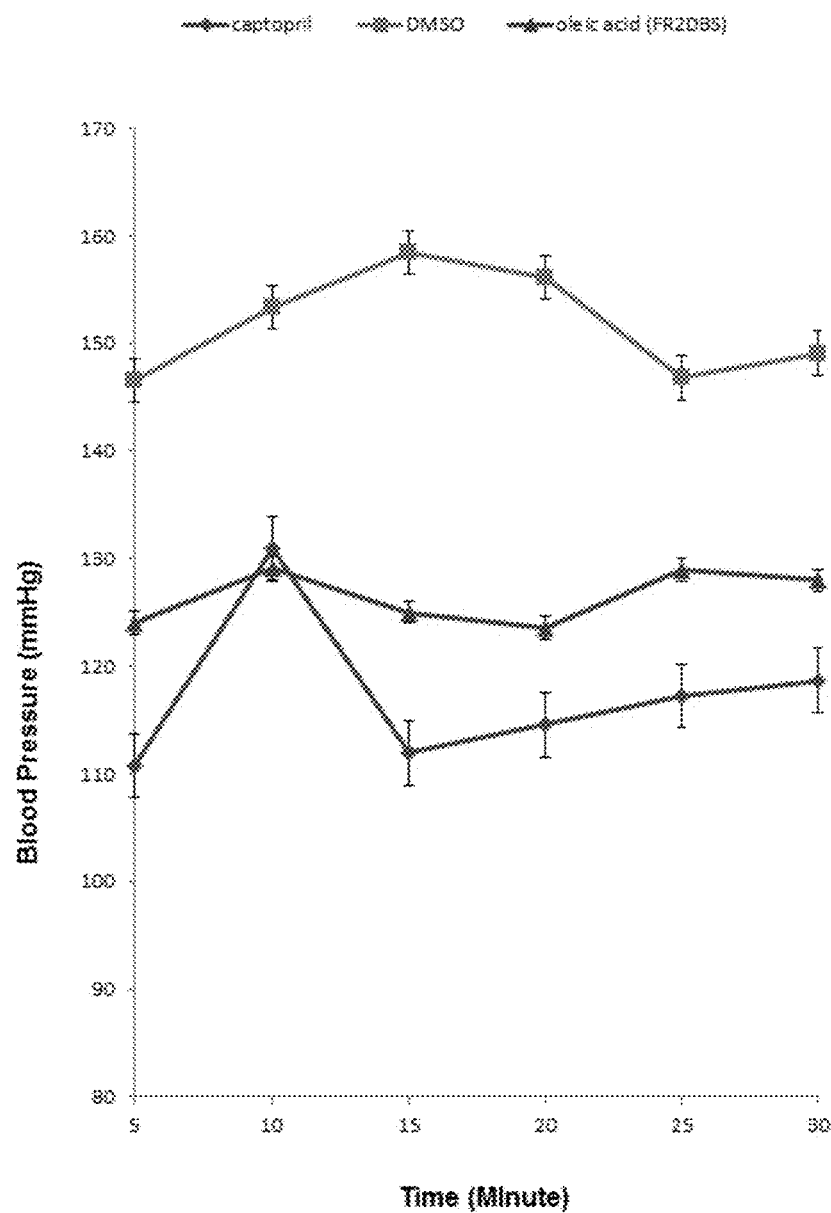
FIG. 25. SBP of oleic acid (FR2DBS) and captopril at 30 mg/kg BW vs DMSO.

In FIG. 24, the heart rates for both controls were relatively constant and showed no significant difference except at the 15 minute interval (389.14±9.81 vs 401.0±6.28 BPM for DMSO and captopril respectively; $p=0.02$). This was also the case for FR2DBW (394.68±6.82 BPM) for the first 10 minutes, that is the heart rate was similar to that of captopril (399.93±6.91 BPM; $p=0.09$) and DMSO was slightly higher than FR2DBW with 405.70±8.95 BPM ($p=0.04$). Subsequent to that this combined product (FR2DBW) caused a significant reduction in the heart rate, being lowest at the 15 minute interval (365.72±6.34 BPM) and was significantly lower than captopril ($p=5.6\times10^{-07}$) but not DMSO ($p=0.07$). FR2DBW (377.04±5.99 BPM) was also not significantly different from the negative control, DMSO (392.09±6.60 BPM) at the 20 minute interval ($p=0.09$). Therefore, overall fr2dbw was able to reduce the heart rate more effectively than captopril, which did not cause a significant lowering. Thus, FR2DBW, the administration of oleic acid:palmitic acid, appears to be a fast-acting vasodilator or any other mechanism that causes the blood vessels to relax in order to reduce the blood pressure. Its action can be similar to that of captopril in altering the Renin-Angiotension Aldosterone System (RAAS) which prevents conversion of angiotensin I to angiotension II. A higher dosage of FR2DBW would possibly show a further lowering of the blood pressure.

The Effect of FR2DBS (Oleic Acid) on Haemodynamic Parameters

Oleic acid (FR2DBS) caused a significant decrease in the pressure being exerted on the blood vessels. The systolic rate produced by FR2DBS (FIG. 25) was very low and comparable to the effect caused by captopril. There was no significant difference between the two samples for the systolic rate, which can be seen at the 10, 15 and 20 minute intervals where $p=0.43$, $p=0.11$ and $p=0.30$ respectively.

Figure 26:
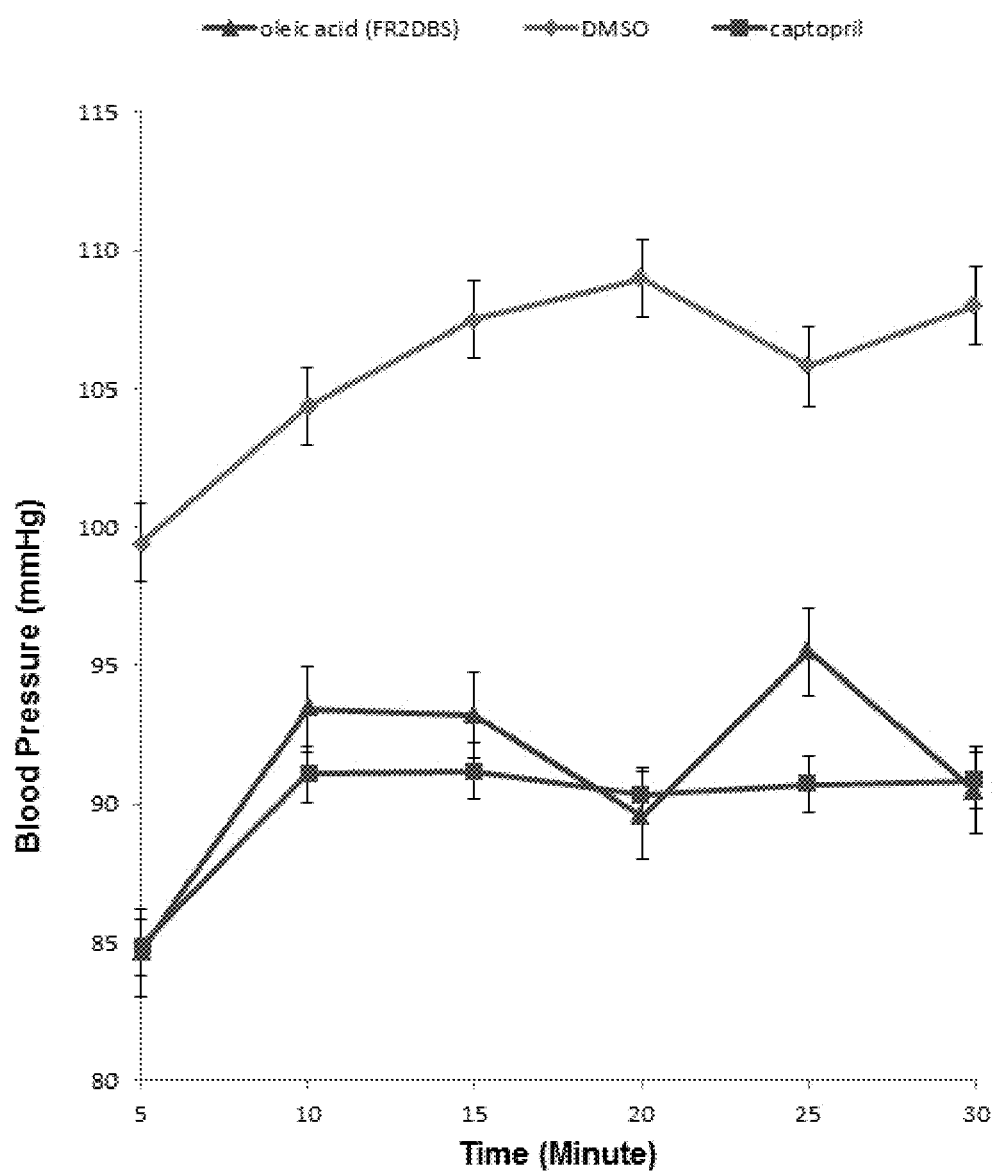
FIG. 26. DBP of oleic acid (FR2DBS) and captopril at 30 mg/kg BW vs DMSO.

The diastolic blood pressure was also significantly reduced throughout the experiment when compared with the DMSO control ($p<0.05$) (FIG. 26). At the 10 minute interval, FR2DBS resulted in a lowered DBP (93.42±1.74 mmHg) compared with 104.36±1.81 mmHg for DMSO ($p=0.0002$) which showed a significant decrease in the diastolic pressure. The comparison with captopril showed the effect to be similar between both compounds in decreasing the diastolic rate ($p>0.05$). There was no significant difference between FR2DBS (93.21±1.33 mmHg) and captopril (91.19±1.37 mmHg) at the 15 minute interval ($p=0.30$). This was a significant reduction in diastolic pressure as the control was 107.50±2.54 mmHg at the same time interval (15 minute).

Figure 27:
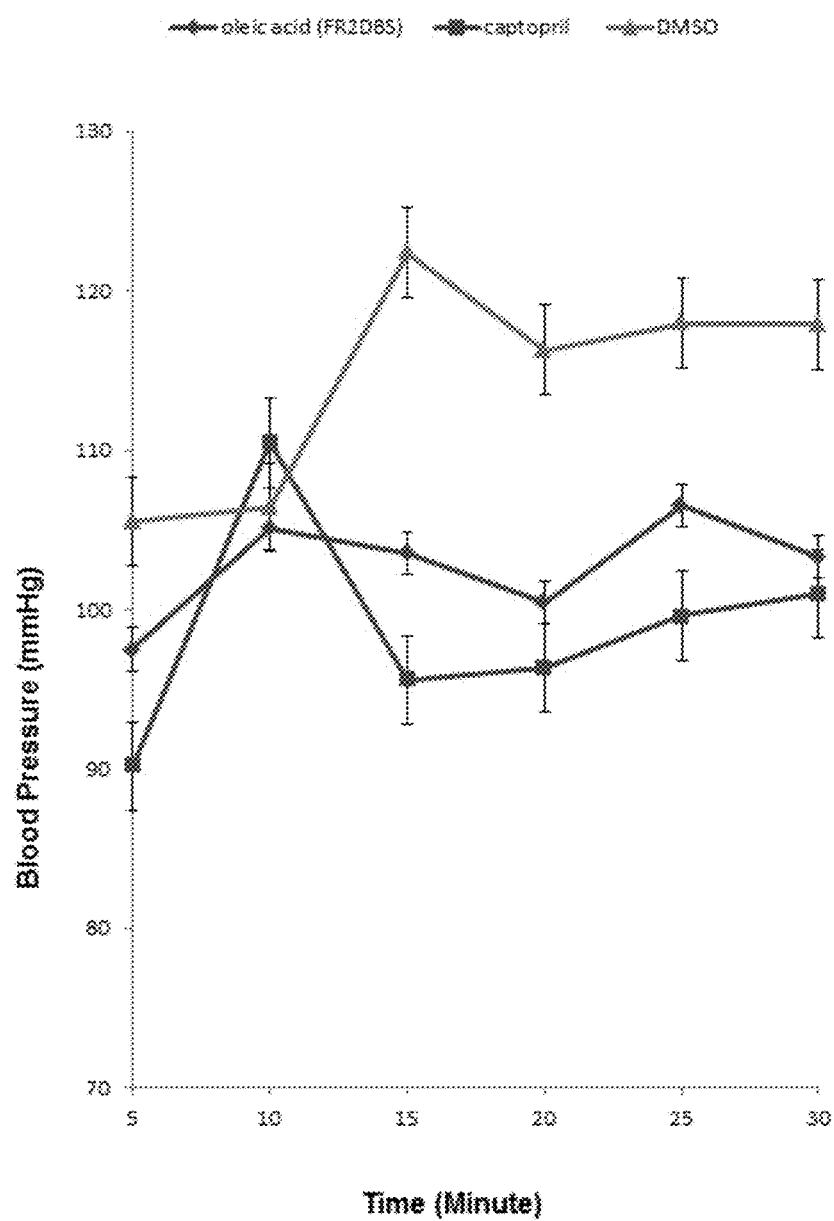
FIG. 27. MAP of oleic acid (FR2DBS) and captopril at 30 mg/kg BW vs DMSO.

This was also seen in FIG. 27 where FR2DBS produced a significant decrease in the mean arterial pressure being exerted when compared with DMSO. At the 10 minute interval, FR2DBS was slightly more effective in reducing the mean blood pressure than captopril (p=0.04), but was not significantly different from the DMSO control (p=0.72). FR2DBS and captopril subsequently brought about a significant decrease in the mean arterial pressure, showing no significant difference between each other. At the 20 minute interval, 100.43±1.39 mmHg of pressure was experienced when FR2DBS was administered compared with 105.07±2.06 mmHg for captopril (p=0.072).

Figure 28:
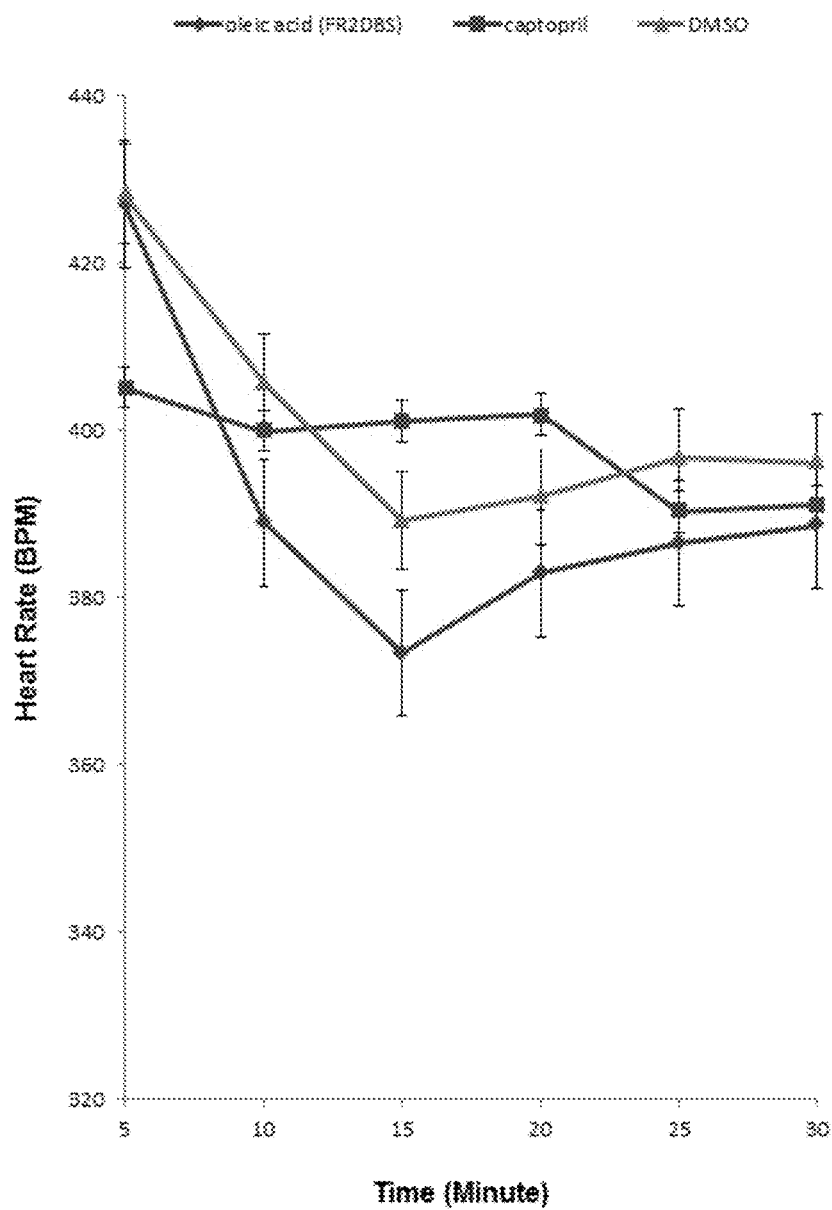
FIG. 28. The effect of oleic acid (FR2DBS) and captopril at 30 mg/kg BW vs DMSO on the heart rate.

In FIG. 28, the effect of oleic acid (FR2DBS) on the heart rate was significantly lower than both captopril and the DMSO controls, especially during the first 15 minutes after administration, after which they reacted similarly. There was a significant decrease at the 10 minute interval, p=0.02, when FR2DBS (388.89±7.27 mmHg) was compared with captopril (412.52±6.91 mmHg). This was also significant at the 15 and 20 minute intervals (p<0.05). In fact, at the 20 minute interval FR2DBS was significantly lower than captopril (p=0.008) but not significantly different from DMSO (p=0.21), hence no significant reduction in the heart rate. Therefore, this fast-acting decrease in the heart rate was able to sustain and cause a decrease in the blood pressure and thereby sustain this decrease throughout, as seen in the previous FIGS. 25-27.

The mechanism therefore can be that a short period of reduced contraction of the heart can in effect cause vasodilation or interference of the hormones within the autonomic nervous system which initiates a decrease in the overall heart rate and blood pressure.

The results above confirm that the synergistic effect of the mixture of oleic acid and palmitic acid is more effective that either of the fatty acid singly, with respect to their hypotensive properties.

Example 9

The Isolation, Purification and Elucidation of the Hypoglycaemic Principles Isolated from *Eucalyptus camaldulensis* In Vivo The objectives of the study were to determine the hypoglycaemic effect of the crude extracts of *Eucalyptus camaldulensis* in normoglycaemic rats, to purify the active extract using various chromatographic techniques and to elucidate the hypoglycemic principle(s) using various spectroscopic techniques.

Introduction
Blood Glucose Concentration

Glucose is the primary source of energy utilized by the cells within the body Normal blood glucose concentration is 3.9-5.5 mmol/L (70-99 mg/dL). A significant decrease in blood glucose concentration, called hypoglycemia, results in <3.9 mmol/L. A significant increase in blood glucose concentration is called hyperglycemia. The latter includes impaired fasting glucose at 5.6-6.9 mmol/L (100-125 mg/dL) and diabetic state at >7.0 mmol/L (>126 mg/dL).

Diabetes Mellitus and Hyperglycemia

Type 1 diabetes mellitus is an autoimmune disease, where the body's immune system destroys the beta cells in the pancreas. Type 1 affects 10-15% of the persons diagnosed with diabetes mellitus.

Type 2 diabetes mellitus is due to insulin resistance or relative insulin deficiency as the pancreas is usually producing enough insulin, but the body is unable to utilize it effectively. Type 2 affects 85-90% of the persons diagnosed with diabetes mellitus.

Gestational diabetes is that which develops in some women late in pregnancy due to the hormones of pregnancy or a shortage of insulin.

The symptoms of diabetes include excessive thirst, blurry vision, weight loss, polyuria and polyphagia. Long term complications include hypertension, cardiovascular symptoms, leg ulcers, amputation, loss of vision, sexual dysfunction, and cerebrovascular disease.

Diabetes mellitus and hyperglycemia are two "lifestyle" diseases that have become a global epidemic. An estimated 170 million persons were affected globally in 2000, with 800,000 new cases annually (World Health Organization and American Diabetes Association). In the Caribbean, these diseases are the leading cause of secondary blindness. In Jamaica, they are two of the leading causes of death, with 150,000 Jamaicans between the ages of 15-74 affected (World Health Organization). Other lifestyle diseases include cardio-vascular diseases, hypertension, some forms of cancer and obesity.

Hypertension is another of the "lifestyle" diseases, which when combined with other such diseases, is even more potent. It can be undetected for years and be a silent killer. Hypertension very adversely affects a number of organs, such as the kidneys, heart and eyes. It can result in increased incidences of cardio-vascular diseases, kidney failure and blindness. The WHO reports in 2012 that up to 40% of the world population older than 25 years of age have a higher than normal blood pressure level. In Jamaica, it has been reported that 30.8% of the population over the age of 15 years has a higher than normal blood pressure level.

Treatments for Diabetes Mellitus

Some oral hypoglycemic drugs that are currently being used include the following:
  Sulfonylureas: stimulate the pancreas to release insulin e.g. Diabinese and Glucotrol.
  Thiazolidinediones: increase tissue sensitivity and inhibit hepatic gluconeogenesis e.g. Avandia.
  Biguanides: inhibit hepatic gluconeogenesis, increase glucose transporters and tissue sensitivity to endogenous insulin e.g. Glucophage.
  Alpha-glucosidase: inhibit the hydrolysis of carbohydrates and reduce glucose absorption e.g. Prandase.

Folklore medicine has also been used to treat diabetes mellitus. Traditionally, plants have been known to contain healing properties, which thus initiates the use as a cure for various ailments. One such traditional plant used is the *eucalyptus*, which was introduced to the West in the nineteenth century.

The *eucalyptus* is a large, fast-growing tree native to Australia. It is part of the Myrtaceae family with over 800 species. This evergreen grows to 126-160 meters (375-480 feet) and is located nearby inland water courses. Species include the blue gum tree, Australian fever tree, Stringy bark tree or the Malee.

The *eucalyptus* tree was introduced in Jamaica because of its numerous medicinal properties, and to build the lumber industry, as the tree grew very fast and was a very successful lumber plant in other countries. Some species found in Jamaica include *E. camaldulensis, E. grandis, E. globulus, E. viminalis, E. citriodora* and *E. robusta*.

*Eucalyptus camaldulensis* is one of several species of *Eucalyptus* introduced into Jamaica in the early 1900's, as sources of lumber and for watershed management. There were several reports of local use as a treatment for Diabetes mellitus, e.g. in Hope Bay, Portland, brewed as a tea. There are many reports of medicinal properties around the world from countries in which these trees have been introduced.

The chemical constituents of the *eucalyptus* tree include phenolic acids, tannins, sesquiterpenes, aldehydes & ketones, flavanoids (eucalyptin, hyperin, quercitin, quercitrin, rutin and hyperoside) and oleanolic acid.

The properties of the plant's distinct volatile oil include antidiabetic, antibacterial, anti-inflammatory, expectorant, diurectic, anaesthetic, antiseptic and decongestant properties.

The ethnomedicinal properties of the plant are found in the 15-30 cm (6-12 inches) blue-green leaves from which tea is made.

Methods and Results

Extraction

Three main extraction fractions, hexane, ethyl acetate, methanol, were extracted from the leaves and stems of the *E. camaldulensis* plant. Bioactivity was tested using normglycaemic Sprague-Dawley rats. Blood glucose concentrations were determined using Oral Glucose Tolerance Test (OGTT).

Hypoglycemic activity was found particularly in the hexane fraction.

Isolation of the Active Constituents

Column Chromatography was used to isolate the active constituents and bioactivity analyses identified the active constituents.

The active constituents were assigned laboratory names: FR1DBY, FR1DBE, FR2DBS and FR2DBW.

Identification of the Active Constituents

Identification of the active constituents was done primarily by spectroscopy, I.R. N.M.R, and GC-MS.

The constituents were identified as two fatty acids, a mixture of them and a hydrocarbon. Further confirmation of their identities as palmitic acid and oleic acid was obtained by direct comparisons with the known compounds. Though the compounds were known, their hypoglycaemic property was not known or fully established, especially for palmitic acid.

Glucose Tolerance Tests

For the Glucose Tolerance Tests, the compounds were administered both intravenously and orally. In the tests, the solvents, DMSO or water, were used as negative controls and the very well known Diabetes medication, Metformin, was used as the positive control. The results showed that the fatty acids were of comparable effectiveness as Metformin.

The results also showed that the mixture of fatty acids gave better results than either of the two used singly. The exact ratio for optimum synergistic effect of the two fatty acids was determined. The oils which contain the two fatty acids, oleic acid and palmitic acid, as their main components also exhibited the hypoglycaemic property.

CONCLUSIONS

New methods for the control of two very important "lifestyle" diseases, hyperglycaemia and hypertension, have been identified using oleic acid and palmitic acid.

The synergistic relationship between the compounds has not been previously reported. Being components of well used oils, the need for toxicology tests can be minimized. No reports of toxicity of the hydrocarbon have been found in the literature. The efficacies of the compounds have been found comparable to well known treatments for hyperglycaemia and hypertension.

With activity being demonstrated in both intravenous and oral administration, a variety of applications, such as functional foods and supplements, are possible. The development pathway using rat models in pre-clinical tests is a common methodology to test clinical effects. Clinical tests in humans can also be conducted.

The invention claimed is:

1. A method of treating hyperglycemia, the method comprising administering to a subject in need thereof a therapeutically effective amount of a composition comprising oleic acid and palmitic acid, thereby treating the hyperglycemia by lowering the subject's blood glucose concentration.

2. The method of claim 1, wherein the oleic acid and palmitic acid are present in a ratio of about 1:1 to about 4:1 oleic acid:palmitic acid.

3. The method of claim 1, wherein the oleic acid and palmitic acid are extracted from the leaves of *Eucalyptus camaldulensis*.

4. The method of claim 1, wherein the oleic acid and the palmitic acid have a synergistic effect on hyperglycemia by lowering the subject's blood glucose concentration.

5. The method of claim 4, wherein the treating comprises lowering the subject's blood glucose concentration by about 10% to about 50%.

6. A method of treating hypertension, the method comprising administering to a subject in need thereof a therapeutically effective amount of a composition comprising oleic acid and palmitic acid, thereby treating the hypertension.

7. The method of claim 6, wherein the oleic acid and palmitic acid are present in a ratio of about 1:1 to about 4:1 oleic acid:palmitic acid.

8. The method of claim 6, wherein the oleic acid and palmitic acid are extracted from the leaves of *Eucalyptus camaldulensis*.

9. The method of claim 6, wherein the oleic acid and the palmitic acid have a synergistic effect on hypertension.

10. The method of claim 9, wherein the treating comprises reducing the subject's systolic blood pressure (SBP) by about 10% to about 55%.

11. The method of claim 9, wherein the treating comprises reducing the subject's diastolic blood pressure (DBP) by about 10% to about 45%.

12. The method of claim 9, wherein the treating or preventing comprises reducing the subject's heart rate by about 5% to about 40%.

13. The method of claim 4, wherein the treating comprises increasing the subject's blood insulin levels by about 30%.

14. The method of claim 9, wherein the treating comprises reducing the subject's mean arterial blood pressure by about 10%.

15. The method of claim 1, wherein the oleic acid is present at a higher ratio than palmitic acid.

16. The method of claim 6, wherein the oleic acid is present at a higher ratio than palmitic acid.

17. The method of claim 3, wherein the extract is present in a therapeutically effective amount of a composition comprising oleic acid and palmitic acid.

18. The method of claim 8, wherein the extract is present in a therapeutically effective amount of a composition comprising oleic acid and palmitic acid.

19. A method of preparing a composition with hypoglycemic properties, the method comprising isolating an extract from the leaves of *Eucalyptus camaldulensis*, wherein the oleic acid is present at a higher ratio than palmitic acid.

20. A method of preparing a composition with hypotensive properties, the method comprising isolating an extract from the leaves of *Eucalyptus camaldulensis*, wherein the oleic acid is present at a higher ratio than palmitic acid.

* * * * *